(12) United States Patent
Sword

(10) Patent No.: US 10,375,966 B2
(45) Date of Patent: Aug. 13, 2019

(54) FUNGAL ENDOPHYTES FOR IMPROVED CROP YIELDS AND PROTECTION FROM PESTS

(71) Applicant: THE TEXAS A&M UNIVERSITY SYSTEM, College Station, TX (US)

(72) Inventor: Gregory A. Sword, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/723,133

(22) Filed: Oct. 2, 2017

(65) Prior Publication Data

US 2018/0092365 A1    Apr. 5, 2018

Related U.S. Application Data

(60) Division of application No. 14/964,429, filed on Dec. 9, 2015, now abandoned, which is a continuation of application No. 14/535,292, filed on Nov. 6, 2014, now Pat. No. 9,277,751.

(60) Provisional application No. 61/900,935, filed on Nov. 6, 2013, provisional application No. 61/900,929, filed on Nov. 6, 2013.

(51) Int. Cl.
*A01N 63/04* (2006.01)
*A01H 5/10* (2018.01)

(52) U.S. Cl.
CPC .............. *A01N 63/04* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 2,200,532 A | 5/1940 | Sherman | |
| 4,940,834 A | 7/1990 | Hurley et al. | |
| 5,041,290 A * | 8/1991 | Gindrat | A01C 1/06 424/93.5 |
| 5,113,619 A | 5/1992 | Leps et al. | |
| 5,229,291 A | 7/1993 | Nielsen et al. | |
| 5,292,507 A | 3/1994 | Charley | |
| 5,415,672 A | 5/1995 | Fahey et al. | |
| 5,730,973 A | 3/1998 | Morales et al. | |
| 5,919,447 A | 7/1999 | Marrone et al. | |
| 5,994,117 A | 11/1999 | Bacon et al. | |
| 6,072,107 A | 6/2000 | Latch et al. | |
| 6,077,505 A | 6/2000 | Parke et al. | |
| 6,337,431 B1 | 1/2002 | Tricoli et al. | |
| 6,495,133 B1 | 12/2002 | Xue | |
| 6,681,186 B1 | 1/2004 | Denisov et al. | |
| 6,689,880 B2 | 2/2004 | Chen et al. | |
| 6,823,623 B2 | 11/2004 | Minato et al. | |
| 7,037,879 B2 | 5/2006 | Imada et al. | |
| 7,084,331 B2 | 8/2006 | Isawa et al. | |
| 7,335,816 B2 | 2/2008 | Kraus et al. | |
| 7,341,868 B2 | 3/2008 | Chopade et al. | |
| 7,485,451 B2 | 2/2009 | VanderGheynst et al. | |
| 7,555,990 B2 | 7/2009 | Beaujot | |
| 7,632,985 B2 | 12/2009 | Malven et al. | |
| 7,763,420 B2 | 7/2010 | Stritzker et al. | |
| 7,906,313 B2 | 3/2011 | Henson et al. | |
| 7,977,550 B2 | 7/2011 | West et al. | |
| 8,143,045 B2 | 3/2012 | Miansnikov et al. | |
| 8,455,198 B2 | 6/2013 | Gao et al. | |
| 8,455,395 B2 | 6/2013 | Miller et al. | |
| 8,465,963 B2 | 6/2013 | Rolston et al. | |
| 8,728,459 B2 | 5/2014 | Isawa et al. | |
| 9,113,636 B2 | 1/2015 | von Maltzahn et al. | |
| 8,975,489 B2 | 3/2015 | Craven | |
| 9,277,751 B2 | 3/2016 | Sword | |
| 9,288,995 B2 | 3/2016 | von Maltzahn et al. | |
| 9,295,263 B2 | 3/2016 | von Maltzahn et al. | |
| 9,364,005 B2 | 6/2016 | Mitter et al. | |
| 9,408,394 B2 | 8/2016 | von Maltzahn et al. | |
| 9,532,572 B2 | 1/2017 | von Maltzahn et al. | |
| 9,532,573 B2 | 1/2017 | von Maltzahn et al. | |
| 9,545,111 B2 | 1/2017 | Sword | |
| 9,622,485 B2 | 4/2017 | von Maltzahn et al. | |
| 9,652,840 B1 | 5/2017 | Shriver et al. | |
| 9,687,001 B2 | 6/2017 | Vujanovic et al. | |
| 9,756,865 B2 | 9/2017 | Sword | |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

PCT International Search Report and Written Opinion for PCT/US2017/064361, dated May 11, 2018, 22 Pages.

(Continued)

*Primary Examiner* — Alton N Pryor
(74) *Attorney, Agent, or Firm* — Fenwick & West LLP

(57) ABSTRACT

The invention provides a synthetic combination of a crop and at least one fungal endophyte, wherein the crop is a host plant of the endophyte. Provided are also methods and compositions for producing such synthetic combinations. The endophyte reproduces and enhances the agronomic characteristics of the crop. Methods for inoculating the host plant with the endophyte, for propagating the host-endophyte combination, and for detecting the presence of the endophyte and of its metabolites within a host plant are also described.

12 Claims, 29 Drawing Sheets

Specification includes a Sequence Listing.

(56) References Cited

U.S. PATENT DOCUMENTS

| | | |
|---|---|---|
| 10,058,101 B2 | 8/2018 | von Maltzahn et al. |
| 10,076,120 B2 | 9/2018 | von Maltzahn et al. |
| 2005/0072047 A1 | 4/2005 | Conkling et al. |
| 2006/0046246 A1 | 3/2006 | Zeng et al. |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2010/0064392 A1 | 3/2010 | Yang et al. |
| 2010/0095396 A1 | 4/2010 | Voeste et al. |
| 2010/0205690 A1 | 8/2010 | Blasing et al. |
| 2010/0227357 A1 | 9/2010 | Redman et al. |
| 2011/0182862 A1 | 7/2011 | Green et al. |
| 2012/0108431 A1 | 5/2012 | Williams et al. |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0230478 A1 | 8/2015 | Vujanovic et al. |
| 2015/0242970 A1 | 8/2015 | Avey et al. |
| 2015/0335029 A1 | 11/2015 | Mitter et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0366892 A1 | 12/2016 | Ambrose et al. |
| 2017/0020138 A1 | 1/2017 | Von Maltzahn et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0092365 A1 | 4/2018 | Sword |
| 2018/0153174 A1 | 6/2018 | Riley et al. |
| 2018/0177196 A1 | 6/2018 | Sword |
| 2018/0213800 A1 | 8/2018 | Djonovic et al. |
| 2018/0249716 A1 | 9/2018 | Raymond |
| 2018/0251776 A1 | 9/2018 | Raymond |

FOREIGN PATENT DOCUMENTS

| | | |
|---|---|---|
| CA | 2562175 | 1/2013 |
| CN | 1604732 | 4/2005 |
| CN | 101311262 A | 11/2008 |
| CN | 101423810 A | 5/2009 |
| CN | 101570738 | 11/2009 |
| CN | 101693881 A | 4/2010 |
| CN | 102168022 A | 8/2011 |
| CN | 102352327 A | 2/2012 |
| CN | 102010835 B | 4/2012 |
| CN | 102533601 B | 10/2013 |
| CN | 103642725 A | 3/2014 |
| CN | 104560742 A | 1/2015 |
| CN | 104388356 A | 3/2015 |
| EP | 0192342 | 8/1986 |
| EP | 0223662 | 5/1987 |
| EP | 0378000 | 7/1990 |
| EP | 0494802 | 7/1992 |
| EP | 0818135 | 1/1998 |
| EP | 1621632 A1 | 2/2006 |
| EP | 1935245 | 6/2008 |
| EP | 2676536 | 12/2013 |
| JP | 2009/072168 | 4/2009 |
| KR | 20100114806 A | 10/2010 |
| KR | 101091151 | 12/2011 |
| KR | 20130023491 | 3/2013 |
| WO | WO 1988/009114 | 1/1988 |
| WO | WO 1994/016076 | 7/1994 |
| WO | WO 2000/029607 | 5/2000 |
| WO | WO 2001/083818 | 11/2001 |
| WO | WO 2002/065836 | 8/2002 |
| WO | WO 2005/003328 | 1/2005 |
| WO | WO 2007/021200 | 2/2007 |
| WO | WO 2007/107000 | 9/2007 |
| WO | WO 2008/103422 | 8/2008 |
| WO | WO 2009/012480 A2 | 1/2009 |
| WO | WO 2009/078710 A1 | 6/2009 |
| WO | WO 2009/126473 A1 | 10/2009 |
| WO | WO 2010/109436 | 9/2010 |
| WO | WO 2010/115156 | 10/2010 |
| WO | WO 2011/001127 | 1/2011 |
| WO | WO 2011/082455 | 7/2011 |
| WO | WO 2011/112781 | 9/2011 |
| WO | WO 2011/117351 | 9/2011 |
| WO | WO 2012/034996 | 3/2012 |
| WO | WO 2013/016361 | 1/2013 |
| WO | WO 2013/029112 | 3/2013 |
| WO | WO 2013/090628 | 6/2013 |
| WO | WO 2013/122473 | 8/2013 |
| WO | WO 2013/177615 | 12/2013 |
| WO | WO 2013/190082 | 12/2013 |
| WO | WO 2014/046553 | 3/2014 |
| WO | WO 2014/082950 | 6/2014 |
| WO | WO 2014/121366 | 8/2014 |
| WO | WO 2014/206953 | 12/2014 |
| WO | WO 2014/210372 | 12/2014 |
| WO | WO 2015/035099 | 3/2015 |
| WO | WO 2015/069938 | 5/2015 |
| WO | WO 2015/100431 | 7/2015 |
| WO | WO 2015/100432 | 7/2015 |
| WO | WO 2015/200852 | 12/2015 |
| WO | WO 2015/200902 | 12/2015 |
| WO | WO 2016/090212 | 6/2016 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |

OTHER PUBLICATIONS

PCT International Search Report and Written Opinion, PCT Application No. PCT/US2017/064292, dated May 11, 2018, 20 Pages.
Canadian Patent Office, Office Action, Canadian Patent Application No. 2,935,218, dated May 8, 2018, 5 Pages.
European Patent Office, Extended European Search Report, European Patent Application No. EP 15876324.3, dated Jun. 12, 2018, 9 Pages.
Intellectual Property Australia, Examination Report No. 1 for Australian Patent Application No. AU 2017210482, dated May 15, 2018, 4 Pages.

(56) References Cited

OTHER PUBLICATIONS

Russian Patent Office, Office Action for Russian Patent Application No. RU 2017141758, dated Apr. 17, 2018, 4 Pages (with Concise Explanation of Relevance).
Russian Patent Office, Office Action for Russian Patent Application No. RU 2017141632, dated Apr. 17, 2018, 4 Pages (with Concise Explanation of Relevance).
Office Action for Israel Patent Application No. IL 245385, dated Apr. 23, 2018, 3 Pages (With Concise Explanation of Relevance).
Aveskamp, M., et al., "DNA phylogeny reveals polyphyly of Phoma section Peyronellaea and multiple taxonomic novelties," Mycologia, 2009, vol. 101, No. 3, pp. 363-382.
Bing, LA, et al., "Suppression of *Ostrinia nubilalis* (Hübner) (Lepidoptera: Pyralidae) by endophytic *Beauveria bassiana* (Balsamo) Vuillemin", Environmental Entomol, Entomological Society of America, College Park, MD, US, vol. 20, Jan. 1, 1991, pp. 1207-1211.
Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession No. AY016368 sequence.
Hubbard, M., et al., 2011. "Agricultural Potential of Fungal Endophytes of Grasses, Cereals and Wheat," In: Wheat: Genetics, Crops and Food Production. Nova Science Publishers Hauppauge, NY, USA. pp. 333-345.
Impullitti, A.E., et al., "Fungal endophyte diversity in soybean", Journal of Applied Microbiolog, vol. 114, No. 5, May 1, 2013, pp. 1500-1506.
Liu, Y., et al., "Phylogenetic relationships among ascomycetes: evidence from an RNA polymerase II subunit," Mol. Biol. Evol. 1999. vol. 16, No. 12, pp. 1799-1808.
Miyoshi-Akiyama, T., et al., "Multilocus Sequence Typing (MLST) for Characterization of Enterobacter cloacae," PLoS One, 2013, vol. 8, No. 6, 10 Pages, e66358.
Nassar, A., et al., "Promotion of plant growth by an auxin-producing isolate of the yeast *Williopsis saturnus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 5, 2012, pp. 69-78.
Riess, K., et al., "High genetic diversity at the regional scale and possible speciation in Sebacina epigaea and S. incrustans," BMC Evolutionary Biology, 2013, vol. 13, No. 102, 17 Pages.
Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.
Vujanovic, V., et al., "A comparative study of endophytic mycobiota in leaves of Acer saccharum in eastern North America," Mycological Progress, May 2002, pp. 147-154, vol. 1, Issue 2.
Vujanovic, V., et al.,"Orchid seed viability testing by fungal bioassays and molecular phylogeny," Floriculture, ornamental and plant biotechnology, 2006, vol. 63, pp. 563-569.
Vujanovic, V., et al., "19th International Conference on *Arabidopsis*. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.

Zhao, J.H., et al., "Bioactive secondary metabolites from *Nigrospora* sp. LLGLM003, an endophytic fungus of the medicinal plant Moringa oleifera Lam." World Journal of Microbiology and Biotechnology, Kluwer Academic Publishers, Feb. 12, 2012, pp. 2107-2112, vol. 28, No. 5.
Zhang, Y., et al., "BcGsl, a glycoprotein from Botrytis cinerea, elicits defence response and improves disease resistance in host plants. Biochemical and biophysical research communications," Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No. JN210900.
Zhu et al., *Helminthosporium velutinum* and *H. aquaticum* sp. nov. from aquatic habitats in Yunnan Province, China. Phytotaxa, 2016, vol. 253, No. 3, pp. 179-190.
Communication pursuant to Article 94(3) EPC for European Patent Application No. EP 14777213.1, dated Jun. 18, 2018, 4 Pages.
First Examination Report for New Zealand Patent Application No. NZ 734085, dated Jun. 27, 2018, 6 Pages.
Abdellatif, L., et al., "Endophytic hyphal compartmentalization is required for successful symbiotic Ascomycota association with root cells," Mycological Research, 2009, pp. 782-791, vol. 113.
Abdou, R., et al., "Botryorhodines A-D, antifungal and cytotoxic depsidones from Botryosphaeria rhodina, an endophyte of the medicinal plant Bidens pilosa," Phytochemistry, 2010, vol. 71, pp. 110-116.
Adhikari, M., et al., "A New Record of Pseudeurotium bakeri from Crop Field Soil in Korea," The Korean Journal of Mycology, 2016, pp. 145-149, vol. 44.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Bensch, K., et al., "Species and ecological diversity within the Cladosporium cladosporioides complex (Davidiellaceae, Capnodiales)," Studies in Mycology, 2010, pp. 1-94, vol. 67.
Canadian Patent Office, Office Action, Canadian Patent Application No. 2,935,218, dated Jun. 13, 2017, 5 Pages.
Canadian Patent Office, Office Action, Canadian Patent Application No. CA 2,929,487, dated Dec. 7, 2017, 4 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,953,466, dated Dec. 11, 2017, 7 Pages.
Canadian Patent Office, Office Action, Canadian Patent Application No. CA 2,953,697, dated Oct. 12, 2017, 6 Pages.
Chagas, F., et al., "A Mixed Culture of Endophytic Fungi Increases Production of Antifungal Polyketides," J. Chem Ecol., Oct. 2013, pp. 1335-1342, vol. 39.
Chinese Patent Office, 2nd Office Action for Chinese Patent Application No. CN 201480072142.7, dated Oct. 30, 2017, 13 Pages, (with English translation).
Chinese Patent Office, Office Action, Chinese Patent Application No. 201480072142.7, dated Apr. 25, 2017, 14 Pages (with English translation).
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Clay, K., "Effects of fungal endophytes on the seed and seedling biology of Lolium perenne and Festuca arundinacea," Oecologia, 1987, pp. 358-362, vol. 73.

(56) References Cited

OTHER PUBLICATIONS

Dbget, "Orthology: K14454," 2005, 2 pages, can be retrieved at <URL:http://www.genome.jp/dbget-bin/www_bget?ko:K14454>.
Desiro, A., et al., "Detection of a novel intracellular microbiome hosted in arbuscular mycorrhizal fungi," ISME Journal, 2014, pp. 257-270, vol. 8.
European Patent Office, Communication Pursuant to Article 94(3) EPC for European Patent Application No. 13874703.5, dated Jan. 5, 2018, 4 Pages.
European Patent Office, Communication Pursuant to Article 94(3) EPC for European Patent Application No. 15810847.2, dated Nov. 17, 2017, 17 Pages.
European Patent Office, Examination Report for European Patent Application No. EP 14777213.1, dated Oct. 20, 2017, 12 Pages.
European Patent Office, Examination Report, European Patent Application No. 14748326.7, dated Jul. 19, 2017, 4 Pages.
European Patent Office, Supplementary European Search Report, European Patent Application No. 14874589.6, dated Jul. 11, 2017, 9 Pages.
European Patent Office, Supplementary European Search Report, European Patent Application No. EP 15809264.3, dated Dec. 4, 2017, 16 Pages.
European Patent Office, Supplementary European Search Report, European Patent Application No. EP 15812324.0, dated Nov. 2, 2017, 19 Pages.
European Patent Office, Supplementary Partial European Search Report, European Patent Application No. 13874703.5, dated Jun. 21, 2016, 3 Pages.
Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
Gen Bank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 Pages, can be retrieved at <URL:https://www.ncbi.nlm.nih.gov/nuccore/AF034210>.
GenBank: JN210900.1, "*Enterobacter* sp. W505 16S ribosomal RNA gene, partial sequence," NCBI, Sep. 24, 2012, 1 Page, can be retrieved at <URL:https://www.ncbi.nlm.nih.gov/nuccore/jn210900>.
GenBank: NP_001237541.1, "Aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001237541.1>.
GenEmbl database, GenEmbl Record No. EU 977189, Jan. 21, 2009, 4 pages, Smith, S.A., et al., "Bioactive endophytes warrant intensified exploration and conservation," PloS One 3(8):E3052, 2008.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Humann, J., et al., "Complete genome of the onion pathogen Enterobacter cloacae EcWSU1," Standard in Genomic Sciences, Dec. 31, 2011, vol. 5, No. 3, pp. 279-286.
Intellectual Property Australia, Examination Report for Australian Patent Application No. 2014315191, dated Jul. 15, 2017, 6 Pages.
Intellectual Property Australia, Examination Report for Australian Patent Application No. 2015278238, dated Jul. 24, 2017, 3 Pages.
Intellectual Property Australia, Examination Report for Australian Patent Application No. 2015279600, dated Jul. 21, 2017, 7 Pages.
Intellectual Property Australia, Examination Report for Australian Patent Application No. 2016202480, dated Apr. 28, 2016, 2 Pages.
Intellectual Property Australia, Examination Report No. 1 for Australian Patent Application No. AU 2017254880, dated Nov. 15, 2017, 2 Pages.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.
Kuklinsky-Sobral, J., et al., "Isolation and characterization of soybean-associated bacteria and their potential for plant growth promotion," Environmental Microbiology, 2004, pp. 1244-1251, vol. 6, No. 12.
Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Labeda, D.P., et al., "Phylogenetic study of the species within the family Streptomycetaceae," Antonie van Leeuwenhoek, 2012, vol. 101, pp. 73-104, Springer.
Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Misk, A., et al., "Biocontrol of chickpea root rot using endophytic actinobacteria", Biocontrol, vol. 56, No. 5, Mar. 12, 2011, pp. 811-822.
Naik, B. S., et al., "Study on the diversity of endophytic communities from rice (*Oryza sativa* L.) and their antagonistic activities in vitro," Microbiological Research, 2009, pp. 290-296, vol. 164.
New Zealand Intellectual Property Office, First Examination Report for New Zealand Patent Application No. NZ 728483, dated Dec. 8, 2017, 2 Pages.

(56) References Cited

OTHER PUBLICATIONS

New Zealand Intellectual Property Office, First Examination Report, New Zealand Patent Application No. 715728, dated May 10, 2016, 4 Pages.
New Zealand Intellectual Property Office, First Examination Report, New Zealand Patent Application No. 726116, dated Jun. 29, 2017, 2 Pages.
New Zealand Intellectual Property Office, First Examination Report, New Zealand Patent Application No. 726116, dated Sep. 26, 2017, 5 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 728495, dated Jul. 12, 2017, 5 Pages.
Nimnoi, P., et al., "Co-Inoculation of Soybean (*Glycin max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Orole, O. O., et al., "Bacterial and fungal endophytes associated with grains and roots of maize," Journal of Ecology and the Natural Enviornment, 2011, pp. 298-303, vol. 3, No. 9.
PCT International Preliminary Report on Patentability, PCT Application No. PCT/US2016/030292, Aug. 2, 2017, 23 Pages.
PCT International Search Report and Written Opinion, Application No. PCT/AU2014/000360, dated Aug. 5, 2015, 12 Pages.
PCT International Search Report and Written Opinion, PCT Application No. PCT/US2015/068206, dated Jun. 27, 2016, 20 Pages.
PCT Invitation to Pay Additional Fees, PCT Application No. PCT/US2015/068206, dated Apr. 12, 2016, 5 Pages.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Ren, Y., et al., "Complete Genome Sequence of *Enterobacter cloacae* subsp. cloacae Type Strain ATCC 13047," J. Bacteriol. May 2010, vol. 192, No. 9, pp. 2463-2464.
Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.
Russian Patent Office, Office Action for Russian Patent Application No. RU 2015137613, dated Jun. 7, 2017, 14 Pages (with English translation).
Russian Patent Office, Office Action for Russian Patent Application No. RU 2017127214, dated Nov. 22, 2017, 4 Pages, (with English translation).
Senthilkumar, M., et al., "Biocontrol Potential of Soybean Bacterial Endophytes Against Charcoal Rot Fungus, Rhizoctonia bataticola," Current Microbiology, 2009, vol. 58, pp. 288-293.
Shankar, M., et al.,"Root colonization of a rice growth promoting strain of Enterobacter cloacae," Journal of Basic Microbiology, 2011, pp. 523-530, vol. 51.
Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.
Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.
Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Tamura, K., et al., "Estimation of the number of nucleotide substitutions in the control region of mitochondrial DNA in humans and chimpanzees," Molecular Biology and Evolution, 1993, vol. 10, No. 3, pp. 512-526.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in *Spodoptera litura* (Lepidoptera: Noctuidae) Larvae by Endophytic Fungi Nigrospora oryzae and Cladosporium uredinicola,", Annals of the Entomological Society of America, May 1, 2014, pp. 674-679, vol. 107, No. 3.
Ukraine Patent Office, Office Action for Ukrainian Patent Application No. a201508515, dated May 19, 2017, 14 Pages (with English translation).
Verkley, G., et al., "*Paraconiothyrium*, a new genus to accommodate the mycoparasite Coniothyrium minitans, anamorphs of Paraphaeosphaeria, and four new species," Studies in Mycology, 2004, pp. 323-335, vol. 50.
Visagie, C.M., et al., "Identification and nomenclature of the genus *Penicillium*," Studies in Mycology, Jun. 2014, pp. 343-371, vol. 78.
Weindling, R., "Relation of dosage to control of cotton seedling diseases by seed treatment," Plant Disease Reporter, 1943, 27, pp. 68-70.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.
PCT Invitation to Pay Additional Fees, PCT App. No. PCT/US2017/064351, dated Feb. 9, 2018, 18 Pages.
PCT International Search Report and Written Opinion, PCT App. No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT Invitation to Pay Additional Fees, PCT App. No. PCT/ US2017/064292, dated Mar. 5, 2018, 15 Pages.
PCT International Search Report and Written Opinion, PCT Application No. PCT/USS2017/068255, dated Mar. 19, 2018, 14 Pages.
European Patent Office, Communication Pursuant to Article 94(3) EPC for European Patent Application No. EP 14748326.7, dated Feb. 15, 2018, 7 Pages.
European Patent Office, Supplementary European Search Report for European Patent Application No. EP 15810847.2, dated Feb. 28, 2018, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
Intellectual Property Australia, Examination Report No. 1 for Australian Patent Application No. AU 2017201009, dated Apr. 4, 2018, 3 Pages.
New Zealand Intellectual Property Office, Further Examination Report, New Zealand Patent Application No. 726116, dated Feb. 27, 2018, 6 Pages.

(56) References Cited

OTHER PUBLICATIONS

Ukraine Patent Office, Office Action for Ukrainian Patent Application No. a201508515, dated Feb. 20, 2018, 9 Pages.
Office Action for Israel Patent Application No. IL 255682, dated Mar. 15, 2018, 2 Pages (Translation).
Office Action for Israel Patent Application No. IL 255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).
Abdellatif, L., et al., "Characterization of virulence and PCR-DGGE profiles of Fusarium avenaceum from western Canadian Prairie Ecozone of Saskatchewan,"Canadian Journal of Plant Pathology, 2010, pp. 468-480.
Abou-Shanab, R.A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Amatuzzi, R.F., et al., "Universldade Federal Do Parana," Jan. 1, 2014, 52 Pages. (With English Abstract).
Amatuzzi, R.F., et al., "Potential of endophytic fungi as biocontrol agents of Duponchelia fovealis (Zeller) (Lepidoptera:Crambidae," Brazilian Journal of Biology, Nov. 9, 2017, 7 Pages.
Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.
NCBI GenBank: CP000653.1 "Enterobacter sp. 638, complete genome" Jan. 28, 2014, 5 Pages, Can be retrieved at <URL:https://www.ncbi.nlm.nih.gov/nuccore/CP000653.1>.
NCBI GenBank: CP000653.1 "Enterobacter sp. 638, complete genome" ASM1632v1, Apr. 18, 2007, 2 Pages, Can be retrieved at <URL:https://www.ncbi.nlm.nih.gov/assembly/GCA_000016325.1>.
NCBI GenBank: EU340965.1 "Enterobacter sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:JQ759988, "Dothideomycetes sp. genotype 226 isolate FL0175 internal transcribed spacer 1, partial sequence; 5.85 ribosomal RNA gene and internal transcribed spacer 2, complete sequence; and 28S ribosomal RNA gene, partial sequence," May 17, 2012, 1 Page.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 1 Page.
Database Geneseq Database accession No. BAP97938 "Pantoea dispersa strain KACC91642P 16S rDNA sequence, SEQ ID 1." Aug. 15, 2013, 1 Page.
Klaubauf, S., et al., "Molecular diversity of fungal communities in agricultural soils from Lower Austria," Fungal Diversity, Aug. 13, 2010, pp. 65-75, vol. 44, No. 1.
Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.
Kumar, A., et al., "Bio-control potential of Cladosporium sp. (MCPL-461), against a noxious weed Parthenium hysterophorus L.," J. Environ Biol., Mar. 2009, pp. 307-312, vol. 30, Iss. 2.
Kusari, S., et al. "Chemical ecology of endophytic fungi: origins of secondary metabolites," Cell Press, Chem & Biol, vol. 19, pp. 792-798, 2012.
Mandyam, K., et al., "Mutualism-parasitism paradigm synthesized from results of root-endophyte models", Frontiers in Microbiology, vol. 5, Jan. 12, 2015, pp. 1-14.
Hamayun, M., et al., "Cladosporium sphaerospermum as a new plant growth-promoting endophyte from the roots of Glycine max (L.) Merr," World Journal of Microbiology and Biotechnology, Kluwer Academic Publishers, DO, vol. 25, No. 4, Feb. 15, 2009, pp. 627-632.
Rae, R., et al., "A subset of naturally isolated Bacillus strains show extreme virulence to the free-living nematodes Caenorhabditis elegans and Pristionchus pacificus", Environmental Microbiology, vol. 12, No. 11, 2010, pp. 3007-3021.
Samways, M.J., et al., "Assessment of the Fungus Cladosporium Oxyspoum (Berk. and Curt.) As a Potential BioControl Agent Against Certain Homoptera," Elsevier Science Publishers B.V., Jan. 1, 1986, pp. 231-239.
Saunders, M., et al., "Host-Synthesized Secondary Compounds Influence the in Vitro Interactions between Fungal Endophytes of Maize", Applied and Environmental Microbiology, vol. 74, No. 1, Nov. 9, 2007, pp. 136-142.
Shiraishi, A., et al., "Nodulation in black locust by the ammaproteobacteria Pseudomonas sp. and the Betaproteobacteria Burkholderia sp", Systematic and Applied Microbiology, 2010, vol. 33, pp. 269-274.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.
Taghavi, S., et al., "Genome Sequence of the Plant Growth promoting Endophytic Bacterium Enterobacter sp. 638", PLoS Genet., May 2010, vol. 6, Issue 5, e1000943, pp. 1-15.
U'Ren, J.M., et al., "Host and geographic structure of endophytic and endolichenic fungi at the continental scale," American Journal of Botany, May 1, 2012, pp. 898-914, vol. 99, No. 5.
Valencia, E., et al., "Mini-review: Brazilian fungi diversity for biomass degradation," Fungal Genetics and Biology, 2013, pp. 9-18, vol. 60.
Vujanovic, V., et al., "Viability Testing of Orchid Seed and the Promotion of Colouration and Germination," Annals of Botany, Mar. 17, 2000, vol. 86, pp. 79-86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "Mycovitality—a new concept of plant biotechnology," Canadian Journal Plant Pathol, 2007, vol. 29, p. 451.
Vujanovic, V., et al., "Seed endosymbiosis: a vital relationship in providing prenatal care to plants," Can. J. Plant Sci., NRC Research Press, Feb. 6, 2017, pp. 972-981, vol. 97.
Youssef, Y.A., et al., "Production of Plant Growth Substances by Rhizosphere Myoflora of Broad Bean and Cotton," Biologia Plantarum, 1975, pp. 175-181, vol. 17, No. 3.
Abarenkov, K., et al., "PlutoF-A Web Based Workbench for Ecological and Taxonomic Research, with an Online Implementation for Fungal ITS Sequences," Evol Bioinform Online, 2010, pp. 189-196, vol. 6.
Abarenkov, K., et al., "The UNITE Database for Molecular Identification of Fungi—Recent Updates and Future Perspectives," New Phytol., 2010, pp. 281-285, vol. 186.
Ahmad, F., et al., "Screening of Free-Living Rhizospheric Bacteria for Their Multiple Plant Growth Promoting Activities," Microbiol Res., 2008, pp. 173-181, vol. 163.
Amann, R., et al., "The Identification of Microorganisms by Fluorescence in Situ Hybridisation," Curr Opin Biotechnol., 2001, pp. 231-236, vol. 12.
Apel, K., et al., "Reactive Oxygen Species: Metabolism, Oxidative Stress, and Signal Transduction," Annu Rev Plant Biol., 2004, pp. 373-399, vol. 55.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Bacon, C. W., et al., "Isolation, in Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev Phytopathol., 1966, pp. 311-334,vol. 4.

(56) References Cited

OTHER PUBLICATIONS

Baltruschat, H., et al., "Salt tolerance of barley induced by the root endophyte Piriformospora indica is associated with a strong increase in antioxidants," New Phytologist., 2008, pp. 501-510, vol. 180.
Block, C. C., et al., "Seed Transmission of Pantoea stewartii in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005.
Bulgarelli, D., et al., "Structure and Functions of the Bacterial Microbiota of Plants," Annu Rev Plant Biol., 2013, pp. 807-838, vol. 64.
Buttner, D., et al., "Regulation and secretion of Xanthomonas virulence factors," FEMS Microbiology Reviews, 2010, pp. 107-133, vol. 34, No. 2.
Canadian Patent Office, Office Action, Canadian Patent Application No. 2,916,678, dated Feb. 8, 2017, 8 Pages.
Caporaso, J.G., et al., "Ultra-High-Throughput Microbial Community Analysis on the Illumina HiSeq and MiSeq Platforms," ISME J., 2012, pp. 1621-1624, vol. 6.
Castillo, D., et al., "Fungal Endophytes: Plant Protective Agents Against Herbivores," Power Point Presentation dated Aug. 4, 2013.
Castillo, D., et al., "Fungal Entomopathogenic Endophytes: Negative Effects on Cotton Aphid Reproduction in Greenhouse and Field Conditions," Power Point Presentation dated Mar. 23, 2013.
Cavalier-Smith, T., "A Revised Six-Kingdom System of Life," Biol Rev Camb Philos Soc., 1998, pp. 203-266, vol. 73.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.
Clark, E. M., et al., "Improved Histochemical Techniques for the Detection of Acremonium coenophilum in Tall Fescue and Methods of in vitro Culture of the Fungus," J. Microbiol Methods, 1983, pp. 149-155, vol. 1.
Clough, S. J., et al., "Floral Dip: A Simplified Method for Agrobacterium-mediated Transformation of *Arabidopsis thaliana*," Plant J., 1998, pp. 735-743, vol. 16, No. 6.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.
Coombs, J. T., et al., "Isolation and Identification of Actinobacteria from Surface-Sterilized Wheat Roots," Applied and Environmental Microbiology, 2003, pp. 5603-5608, vol. 69, No. 9.
Cottyn, B., et al., "Phenotypic and genetic diversity of rice seed-associated bacteria and their role in pathogenicity and biological control," Journal of Applied Microbiology, 2009, pp. 885-897, vol. 107.
Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.
Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.
Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Environmental Microbiology, 2008, pp. 2669-2678, vol. 74, No. 9.
De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.
De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.
De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.
De Souza, J. J., et al., "Terpenoids from Endophytic Fungi," Molecules, 2011, pp. 10604-10618, vol. 16, No. 12.
Dennis, C., et al., "Antagonistic Properties of Species Groups of *Trichoderma*," Trans Brit Mycol Soc, 1971, pp. 25-39, vol. 57, No. 1.
Djordjevic, D., et al., "Microtiter Plate Assay for Assessment of Listeria monocytogenes Biofilm Formation," Annl Environ Microbiol., 2002, pp. 2950-2958, vol. 68, No. 6.
Don, R. H., et al., "Properties of Six Pesticide Degradation Plasmids Isolated From Alcaligenes Paradoxus and Alcaligenes eutrophus," J Bacteriol., 1981, pp. 681-686, vol. 145, No. 2.
Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012.
Eberhard, A., et al., "Structural Identification of Autoinducer of Photobacterium fischeri Luciferase," Biochem., 1981, pp. 2444-2449, vol. 20.
Edgar, R. C., "Search and Clustering Orders of Magnitude Faster than BLAST," Bioinformatics, 2010, pp. 2460-2461, vol. 26, No. 19.
Edgar, R. C., "UPARSE: Highly Accurate OTU Sequences From Microbial Amplicon Reads," Nat Methods, 2013, pp. 996-998, vol. 10, No. 10.
Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012.
Ek-Ramos, M. J., et al., "Spatial and Temporal Variation in Fungal Endophyte Communities Isolated from Cultivated Cotton (*Gossypium hirsutum*)," PLoS One, 2013, vol. 8, No. 6, 13 Pages.
Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.
El-Shanshoury, A. R., "Growth Promotion of Wheat Seedlings by Streptomyces atroolivaceus," Journal of Agronomy and Crop Science, 1989, pp. 109-114, vol. 163.
Emerson, D., et al., Identifying and Characterizing Bacteria in an Era of Genomics and Proteomics, BioScience, 2008, pp. 925-936, vol. 58, No. 10.
Endre, G., et al., "A Receptor Kinase Gene Regulating Symbiotic Nodule Development," Nature, 2002, pp. 962-966, vol. 417.
European Patent Office, Supplementary European Search Report, European Patent Application No. 13874703.5, dated Oct. 21, 2016, 16 Pages.
European Patent Office, Supplementary European Search Report, European Patent Application No. 14860187.5, dated May 24, 2017, 9 Pages.
Faria, D. C., et al., "Endophytic Bacteria Isolated from Orchid and Their Potential to Promote Plant Growth," World J Microbiol Biotechnol., 2013, pp. 217-221, vol. 29.

(56) References Cited

OTHER PUBLICATIONS

Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.
Fiehn, O., et al., "Metabolite Profiling for Plant Functional Genomics," Nature Biotechnol., 2000, pp. 1157-1161, vol. 8.
Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.
Fincher, G. B., "Molecular and Cellular Biology Associated with Endosperm Mobilization in Germinating Cereal Grains," Annu Rev Plant Phvsiol Plant Mol Biol., 1989, pp. 305-346, vol. 40.
Fisher, P. J., et al., "Fungal saprobes and pathogens as endophytes of rice (*Oryza sativa* L.)," New Phytol., 1992, pp. 137-143, vol. 120.
Fisher, P. R., et al., "Isolation and Characterization of the Pesticide-Degrading Plasmid pJP1 from Alcaligenes paradoxus," J Bacteriol., 1978, pp. 798-804, vol. 135, No. 3.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Giraldo, A., et al., "Phylogeny of Sarocladium (*Hypocreales*)," Persoonia, 2015, pp. 10-24, vol. 34.
Gitaitis, R., et al., "The Epidemiology and Management of Seedborne Bacterial Diseases," Annu Rev Phytopathol., 2007, pp. 371-397, vol. 45.
Grondona, I., et al., "TUSAL®, a commercial biocontrol formulation based on Trichoderma," Bulletin OILB/SROP, 2004, pp. 285-288, vol. 27, No. 8.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hallman, J., et al., "Bacterial Endophytes in Agricultural Crops," Canadian J Microbiol., 1997, pp. 895-914, vol. 43.
Hanson, L.E., "Reduction of Verticillium Wilt Symptoms in Cotton Following Seed Treatment with Trichoderma virens," Proceedings Beltwide Cotton Conferences, 2000, vol. 1. (Abstract).
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P. R., et al., "Dynamics of Seed-Borne Rice Endophytes on Early Plant Growth Stages," PLoS One, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hiatt, E. E., et al., "Tall Fescue Endophyte Detection: Commerical Immunoblot Test Kit Compared with Microscopic Analysis," Crop Science, 1999, pp. 796-799, vol. 39.
Hibbett, D. S., et al., "A Higher-Level Phylogenetic Classification of the Fungi," Mycol Res., 2007, pp. 509-547, vol. 111.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hill, N. S., et al., "Endophyte Survival during Seed Storage: Endophyte-Host Interactions and Heritability," Crop Sci., 2009, pp. 1425-1430, vol. 49.
Hinton, D. M., et al., "Enterobacter cloacae is an endophytic symbiont of corn," Mycopathologia, 1995, pp. 117-125, vol. 129.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., et al., "Fungal Endophytes Improve Wheat Seed Germination Under Heat and Drought Stress," Botany, 2012, pp. 137-149, vol. 90.
Hung, P.Q., et al., "Isolation and Characterization of Endophytic Bacteria in Soybean (*Glycine* Sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of the Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Intellectual Property Australia, Examination Report for Australian Patent Application No. 2014346664, dated Nov. 24, 2016, 3 Pages.
Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.
Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Johnston-Monje, D., "Microbial Ecology of Endophytic Bacteria in Zea Species as Influenced by Plant Genotype, Seed Origin, and Soil Environment," Thesis, University of Guelph, 2011, 230 Pages.
Johnston-Monje, D., et al., "Conservation and Diversity of Seed Associated Endophytes in Zea Across Boundaries of Evolution, Ethnography and Ecology," PLoS One, 2011, vol. 6, No. 6, 22 Pages.
Johnston-Monje, D., et al., "Plant and Endophyte Relationships: Nutrient Management," Comprehensive Biotechnol., 2011, pp. 713-727, vol. 4.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013.

(56) References Cited

OTHER PUBLICATIONS

Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.
Kasana, R. C., et al., "A Rapid and Easy Method for the Detection of Microbial Cellulases on Agar Plates Using Gram's Iodine," Curr Microbiol., 2008, pp. 503-507, vol. 57.
Khan, A.L., et al., "Salinity Stress Resistance Offered by Endophytic Fungal Interaction Between Penicillium miniolutem LHL09 and *Glycine max*. L," J. Microbiol. Biotechnol., 2011, pp. 893-902, vol. 21, No. 9.
Kruger, M., et al., "DNA-Based Species Level Detection of Glomeromycota: One PCR Primer Set for All Arbuscular Mycorrhizal Fungi," New Phvtol., 2009, pp. 212-223, vol. 183.
Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.
Lanver, D., et al., "Sho1 and Msb2-Related Proteins Regulate Appressorium Development in the Smut Fungus Ustilago aydis," Plant Cell, 2010, pp. 2085-2101, vol. 22.
Laus, M. C., et al., "Role of Cellulose Fibrils and Exopolysaccharides of Rhizobium leguminosarum in Attachment to and Infection of Vicia sativa Root Hairs," Mol Plant Microbe Interact., 2005, pp. 533-538, vol. 18, No. 6.
Lehman, S.G., "Treat Cotton Seed," Research and Farming III, Progr. Rept., 1945, 3, 5, 16 pages.
Lehman, S.G., "Treat Cotton Seed," Review of Applied Mycology, 1945, 24, 369, 16 pages.
Leonard, C. A., et al., "Random Mutagenesis of the Aspergillus oryzae Genome Results in Fungal Antibacterial Activity," Int J Microbiol., 2013, vol. 2013, Article ID 901697, 6 Pages.
Li, H. M., et al., "Expression of a Novel Chitinase by the Fungal Endophyte in Poa annpla," Mycologia, 2004, pp. 526-536, vol. 96, No. 3.
Li, H., et al., "Endophytes and their role in phytoremediation," Fungal Diversity, 2012, pp. 11-18, vol. 54.
Li, Q., "Agrobacterium tumefaciens Strain TA-AT-10 16S Ribosomal RNA Gene, Partial Sequence: Gen Bank: KF673157.1," Submitted Sep. 17, 2013.
Liu, D., et al., "Osmotin Overexpression in Potato Delays Development of Disease Symptoms," Proc Natl Acad Sci USA, 1994, pp. 1888-1892, vol. 91.
Liu, M., et al., "A Novel Screening Method for Isolating Exopolysaccharide-Deficient Mutants," Appl Environ Microbiol., 1998, pp. 4600-4602, vol. 64, No. 11.
Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.
Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 63.
Lundberg, D. S., et al., "Defining the Core *Arabidopsis thaliana* Root Microbiome," Nature, 2012, pp. 86-90, vol. 488, No. 7409.
Lundberg, D. S., et al., "Practical Innovations for High-Throughput Amplicon Sequencing," Nat Methods, 2013, pp. 999-1002, vol. 10, No. 10.

Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.
Marasco, R., et al., "A Drought Resistance-Promoting Microbiome is Selected by Root System Under Desert Farming," PLoS ONE, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mateos, P. F., et al., "Cell-Associated Pectinolytic and Cellulolytic Enzymes in Rhizobium leguminosarum biovar trifolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Michel, B. E., et al., "The Osmotic Potential of Polyethylene Glycol 6000," Plant Physiol., 1973, pp. 914-916, vol. 51.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato," Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
New Zealand Intellectual Property Office, First Examination Report, New Zealand Patent Application No. 715728, dated Dec. 5, 2016, 3 Pages.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.

(56) References Cited

OTHER PUBLICATIONS

Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Partida-Martinez, L.P., et al., "The Microbe-Free Plant: Fact or Artifact?" Front Plant Sci., 2011, vol. 2, No. 100, 16 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report and Written Opinion, Application No. PCT/US2014/054160, dated Dec. 9, 2014, 21 Pages.
PCT International Search Report and Written Opinion, Application No. PCT/US2014/072400, dated Jul. 8, 2015, 38 Pages.
PCT International Search Report and Written Opinion, International Application No. PCT/US2014/064411, dated Mar. 27, 2015, 15 Pages.
PCT International Search Report and Written Opinion, International Application No. PCT/US2014/072399, dated Jun. 26, 2015, 22 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT International Search Report and Written Opinion, PCT Application No. PCT/US2016/030292, dated Aug. 12, 2016, 20 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT International Search Report, Application No. PCT/US2014/044427, dated Dec. 3, 2014, 9 Pages.
PCT Invitation to Pay Additional Fees, PCT Application No. PCT/CA2013/000091, dated Mar. 27, 2013, 2 Pages.
PCT Invitation to Pay Additional Fees, PCT Application No. PCT/US2014/064411, dated Feb. 5, 2015, 2 Pages.
PCT Invitation to Pay Additional Fees, PCT Application No. PCT/US2014/072399, dated Apr. 14, 2015, 2 Pages.
PCT Invitation to Pay Additional Fees, PCT Application No. PCT/US2014/072400, dated Apr. 16, 2015, 6 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
Pearson, W.R., et al., "Rapid and Sensitive Sequence Comparison With FASTP and FASTA," Methods Enzymol., 2011, pp. 63-98, vol. 183.
Pedraza, R. O., et al., "Azospirillunn inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Fernandez, M. A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, [online][Retrieved Aug. 11, 2016] Retrieved from the Internet <URL:http://www.philrice.gov.ph/2012-rd-highlights/>.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval Helicoverpa zea (*Lepidoptera: Noctuidae*), " J. Entomol. Sci., 2009, pp. 391-396, vol. 44, No. 4.
Production Research Conf., 1989, Memphis, Tennessee, USA, pp. 15-20. (Abstract).
Quadt-Hallmann, A., et al., "Bacterial Endophytes in Cotton: Mechanisms of Entering the Plant," Can J Microbiol., 1997, pp. 577-582, vol. 43.
R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Redman, R. S., et al., "Thermotolerance Generated by Plant/Fungal Symbiosis," Science, Nov. 2002, vol. 298, 1 Page (with 4 pages of supplemental material).
Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001,pp. 11-29, vol. 13.
Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.
Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Sardi, P., et al., "Isolation of Endophytic Streptomyces Strains from Surface Sterilized Roots," Applied and Environmental Microbiology, 1992, pp. 2691-2693, vol. 58, No. 8.

(56) References Cited

OTHER PUBLICATIONS

Sarwar, M., et al., "Tryptophan Dependent Biosynthesis of Auxins in Soil," Plant Soil, 1992, pp. 207-215, vol. 147.
Schmieder, R., et al., "Quality Control and Preprocessing of Metagenomic Datasets," Bioinformatics, 2011, pp. 863-864, vol. 27, No. 6.
Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B. et al., "Universal Chemical Assay for the Detection and Determination of Siderophores," Analytical Biochemistry, 1987, pp. 47-56, vol. 160.
Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.
Soares, M. M. C. N., et al., "Screening of Bacterial Strains for Pectinolytic Activity: Characterization of the Polygalacturonase Produced by *Bacillus* SP," Revista de Microbiolgia, 1999, pp. 299-303, vol. 30.
Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.
Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.
Staudt, A. K., et al., "Variations in Exopolysaccharide Production by Rhizobium tropici," Arch Microbiol., 2012, pp. 197-206, vol. 194.
Strobel, G. A., "Endophytes as Sources of Bioactive Products," Microbes and Infection, 2003, pp. 535-544, vol. 5.
Sturz, A. V., et al., "Weeds as a Source of Plant Growth Promoting Rhizobacteria in Agricultural Soils," Can J Microbiol., 2001, pp. 1013-1024, vol. 47, No. 11.
Surette, M. A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Fungal Endophytes to Protect Cotton from Insects and Nematodes," Power Point Presentation dated Dec. 7, 2012.
Sword, G., "Manipulating Fungal Endophytes to Protect Plants from Insects and Nematodes," Power Point Presentation dated Aug. 7, 2013.
Sword, G., "Natural Enemies—The Forgotten Basis of IPM?," Power Point Presentation dated Sep. 6, 2013.
Sword, G., et al., "Field Trials of Potentially Beneficial Fungal Endophytes in Cotton," Power Point Presentation dated Jan. 7, 2013.
Sword, G., et al., "Manipulating Fungal Endophytes for the Protection of Cotton in the Field," Power Point Presentation dated Jan. 7, 2013.
Taylor, A. G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Theis, K. R., et al., "Uncultured Bacterium Clone GM2GI8201A64RC 16S Ribosomal RNA Gene, Partial Sequence," NCBI GenBank Accession No. JX051943, Submitted May 14, 2012.

Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving Streptomyces Lydicus WYEC108 and the Pea Plant (*Pisum Sativum*)," Applied and Environmental Microbiology, May 2002, pp. 2161-2171, vol. 68, No. 5.
Trichoderma definition, 2016, [online] [Retrieved on Sep. 16, 2016,] Retrieved from the Internet <URL:https://en.wikipedia.org/wiki/Trichoderma>.
Trotel-Aziz, P., et al., "Characterization of New Bacterial Biocontrol Agents *Acinetobacter, Bacillus, Pantoea* and *Pseudomonas* spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
Usadel, B., et al., "The Plant Transcriptome—From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013.
Van Der Lelie, D., et al., "Poplar and its Bacterial Endophytes: Coexistence and Harmony," Critical Rev Plant Sci., 2009, pp. 346-358, vol. 28.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "Pseudomonas thiveralensis Strain IEHa 16S Ribosomal RNA Fene, Partial Sequence," NCBI GenBank Accession No. GQ169380.1, Submitted May 15, 2009.
Waller, F., et al., "The Endophytic Fungus Piriformospora indica Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weaver, P.F., et al., "Characterization of Rhodopseudomonas capsulate," Arch Microbiol., 1975, pp. 207-216, vol. 105.
Weindling, R., "Relation of dosage to control of cotton seedling diseases by seed treatment," Plant Disease Reporter, 1943, 27, 68-70.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings," World J Microbiol Biotechnol., 2014, pp. 835-845, vol. 30.

(56) References Cited

OTHER PUBLICATIONS

Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.

Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.

Yezerski, A., et al., "The Effects of the Presence of Stored Product Pests on the Microfauna of a Flour Community," Journal of Applied Microbiology, 2005, pp. 507-515, vol. 98.

You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).

Zhou, W., et al., "Effects of the Fungal Endophyte Paecilomyces sp. in Cotton on the Roo-Knot Nematode Meloidogyne incognita," poster dated Jan. 7, 2013.

Zimmerman, N. B., et al., "Fungal Endophyte Communities Reflect Environmental Structuring Across a Hawaiian Landscape," Proc Natl Acad Sci USA, 2012, pp. 13022-13027, vol. 109, No. 32.

Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.

Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.

Abello, J., et al., "Agrobacterium-mediated transformation of the endophytic fungus Acremonium implicatum associated with Brachiaria grasses", Mycological Research, pp. 407-413, vol. 112, Pt 3.

Antony-Badu, S., et al., "Multiple Streptomyces species with distinct secondary metabolomes have identical 16S rRNA gene sequences." Scientific Reports 7.1, Sep. 2017, No. 7, 11089, pp. 1-8.

Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.

Azcon, R., et al., "Selective interactions between different species of mycorrhizal fungi and Rhizobium meliloti strains, and their effects on growth, N2-fixation (15N) and nutrition of Medicago sativa L.," New PhytoL., 1991, vol. 117, pp. 399-404.

Bandara, W.M.M.S., et al., "Interactions among endophytic bacteria and fungi: effects and potentials", Journal of Biosciences, Dec. 2006, vol. 31, No. 5, pp. 645-650.

Bragantia, et al: "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).

De Medeiros, L., et al., "Evaluation of Herbicidal Potential of Depsides from Cladosporium uredinicola an Endophytic Fungus found in Guava Fruit," J. Braz. Chem. Soc., 2012, vol. 23, No. 8, pp. 1551-1557.

Fox, G., et al., "How close is close: 16S rRNA sequence identity may not be sufficient to guarantee species identity." International Journal of Systematic and Evolutionary Microbiology 42.1, 1992, pp. 166-170.

Goudjal, Y., et al., "Biocontrol ofRhizoctonia solanidamping-off and promotion of tomato plant growth by endophytic actinomycetes isolated from native plants of Algerian Sahara", Microbiological Research, 2014, vol. 169, No. 1 , pp. 59-65.

Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.

Hain, T., et al., "Chitinolytic transgenes from Streptomyces albidoflavus as phytochemicals defences against herbivorous insects, use in transgenic plants and effect in plant development", International Journal of Systematic Bacteriology, Jan. 1997, vol. 47, No. 1, pp. 202-206.

Hanshew, A., et al., "Characterization of Actinobacteria Associated with Three Ant-Plant Mutualisms", Microbial Ecology, Aug. 6, 2017, vol. 69, No. 1, pp. 192-203.

Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.

Kanbar, A., et al., "Relationship between Root and Yield Morphological Characters in Rainfed Low Land Rice (Oryza sativa L.)," Cereal Research Communications, 2009, vol. 37, No. 2, pp. 261-268.

Li, M., et al., "ATP Modulates the Growth of Specific Microbial Strains", Current Microbiology, May 30, 2010, vol. 62, No. 1, pp. 84-89.

NCBI GenBank: Accession No. JX880250.1, "Enterobacteriaceae bacterium Clerol 16S ribosomal RNA gene, partial sequence," NIH, Jun. 24, 2015, 2 Pages, can be retreived at <URL:https://www.ncbi.nlm.nih.gov/nucleotide/JX880250.1?report=genbank&log$=nuclalign&blast_rank=80 &RID=KWUPBV08015>.

NCBI, GenBank Accession No. XP_002568042, Aug. 14, 2009, 4 Pages, Berg, V.D., et al., "Genome sequencing and analysis of the filamentous fungus," Nat. Biotechnol. 26 (10), 1161-1168 (2008).

NCBI, GenBank Accession No. KX641980.1, Jul. 29, 2017, Scott, M., et al., "Dothideomycetes sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at <URL:https://www.ncbi.nlm.nih.gov/nuccore/KX641980>.

Ogbo, F., et al., "Some Characteristics of a Plant Growth Promoting iEnterobacter/isp. Isolated from the Roots of Maize", Advances in Microbiology, Jan. 1, 2012, vol. 02, No. 03, pp. 368-374.

Partida-Martinez, L.P., et al., "Endosymbiont-Dependent Host Reproduction Maintains Bacterial-Fungal Mutualism", Current Biology, May 1, 2007, vol. 17, No. 9, pp. 773-777.

Sarkar, S., et al., "New report of additional enterobacterial species causing wilt in West Bengal, India," Canadian Journal of Microbiology, 2015, vol. 61, No. 7, pp. 477-486.

Sharma, et al: "Detection and identification of bacteria intimately associated with fungi of the order Sebacinales", Cellular Microbiology, Aug. 5, 2008, pp. 2235-2246, vol. 10, No. 11.

United States Patent Office, Final Office Action, U.S. Appl. No. 14/964,429, dated May 31, 2017, 9 Pages.

United States Patent Office, Final Office Action, U.S. Appl. No. 15/034,862, dated Jan. 12, 2018, 14 Pages.

United States Patent Office, Non-Final Office Action, U.S. Appl. No. 14/964,429, dated Aug. 9, 2016, 6 Pages.

United States Patent Office, Non-Final Office Action, U.S. Appl. No. 15/212,038, dated Sep. 21, 2016, 10 Pages.

United States Patent Office, Non-Final Office Action, U.S. Appl. No. 15/034,862, dated May 19, 2017, 8 Pages.

Sword, G., "Declaration by Dr. Gregory A. Sword Under 37 C.F.R. §1.132 for U.S. Appl. No. 15/723,133," Dec. 19, 2018, four pages.

Allard, G. et al., "Spingo: a rapid species-classifier for microbial amplicon sequences," BMC Bioinformatics, 2015, vol. 16, No. 324, 8 pages.

Anders, S. et al., "Differential expression analysis for sequence count data," Genome Biology, 2010, vol. 11, No. 11, pp. R106.

Ardakani, M.R. et al., "Absorption of N, P, K through triple inoculation of wheat (Triticum aestivum L.) by *Azospirillum brasilense*, *Streptomyces* sp., Glomus intraradices and manure application," Physiol Mol Biol Plants, 2011, vol. 17, No. 2, pp. 181-192.

Bevivino, A. et al., "Characterization of a free-living maize-rhizosphere population of *Burkholderia cepacia*: effect of seed treatment on disease suppression and growth promotion of maize," FEMS Microbiology Ecology, 1998, vol. 27, pp. 225-237.

Chen, F. et al., "Assessing Performance of Orthology Detection Strategies Applied to Eukaryotic Genomes," PLoS One, Apr. 2007, No. 4, pp. e383.

Ciccillo. F. et al., "Effects of two different application methods of *Burkholderia ambifaria* MCI 7 on plant growth and rhizospheric bacterial diversity," Environmental Microbiology, 2002, vol. 4, No. 4, pp. 238-245.

(56) References Cited

OTHER PUBLICATIONS

Cole, J.R. et al., "Ribosomal Database Project: data and tools for high throughput rRNA analysis," Nucleic Acids Research, 2014, vol. 42, pp. D633-D642.
De Santi, M. et al., "A combined morphologic and molecular approach for characterizing fungal microflora from a traditional Italian cheese (Fossa cheese)," Inter. Dairy J., 2010, vol. 10, No. 7, pp. 465-471.
Deshpande, V. et al., "Fungal identification using a Bayesian classifier and the Warcup training set of internal transcribed spacer sequences," Mycologia, 2016, vol. 108, No. 1, pp. 1-5.
Edgar, R.C., "UNOISE2: Improved Error-Correction for Illumina 16S and Its Amplicon Sequncing," BioRxiv, 2016, No. 081257, 21 pages.
Enright, A.J. et al., "An efficient algorithm for large-scale detection of protein families," Nucleic Acids Research, 2002, vol. 30, No. 7, pp. 1575-1584.
Enright, A.J. et al., "Protein families and Tribes in genome sequence space," Nucleic Acids Research, 2003, vol. 31, No. 15, pp. 4632-4638.
Estrada, P. et al., "A N2-fixing endophytic *Burkholderia* sp. Associated with maize plants cultivated in Mexico," Canadian Journal of Microbiology, 2002, vol. 48, No. 4, pp. 285-294.
Friedman, J. et al., "Regularization Path for Generalized Linear Models via Coordinate Descent," Journal of Statistical Software, 2010, vol. 33, No. 1, pp. 1-22.
Koljalg. U. et al., "Towards a unified paradigm for sequence-based identification of fungi," Molecular Ecology, 2013, vol. 22, pp. 5271-5277.
Kozich, J.J. et al., "Development of a Dual-Index Sequencing Strategy and Curation Pipeline for Analyzing Amplicon Sequence Data on the MiSeq Illumina Sequencing Platform," Applied and Environmental Microbiology, Sep. 2013, vol. 79, No. 17, pp. 5112-5120.
Langille, M.G.I. et al., "Predictive functional profiling of microbial communities using 16S rRNA marker gene sequences," Nature Biotechnology, 2013, vol. 31, No. 9, pp. 814-821.
Li, W. et al., "Ultrafast clustering algorithms for metagenomic sequence analysis," Briefings in Bioinformatics, Nov. 1, 2012, vol. 13, No. 6., pp. 656-668.
McMurdie, P.J. et al., "Waste Not, Want Not: Why Rarefying Microbiome Data Is Inadmissible," PLOS Computational Biology, 2014, vol. 10, No. 4, pp. e1003531.
Needleman, S.B. et al., "A General Method Applicable to the Search for Similarities in the Amino Acid Sequence of Two Proteins," Journal of Molecular Biology, 1970, vol. 28, No. 3, pp. 443-453.
Quast, C. et al., "The Silva ribosomal RNA gene database project: improved data processing and web-based tools," Nucleic Acids Research, 2013, vol. 41, pp. D590-D596.
Rideout, J.R. et al., "Subsampled open-reference clustering creates consistent, comprehensive OTU definitions and scales to billions of sequences," PeerJ, 2014, 2:e545.
Roth, A.C.J. et al., "Algorithm of OMA for large-scale orthology inference," BMC Bioinformatics, 2008, vol. 9, pp. 518.
"Sequence Alignment of JQ047949 with Instant Seq Id No: 2," Search conducted on Jan. 2, 2019. 2 pages.
Sharma, V.K. et al., "Enhancement of verticillium wilt resistance in tomato transplants by in vitro co-culture of seedlings with a plant growth promoting rhizobacterium (*Pseudomonas* sp. Strain PsJN)," Canadian Journal of Microbiology, Jun. 1998, vol. 44, No. 6, pp. 528-536.
Shenoy, B.D. et al., "Impact of DNA sequence-data on the taxonomy of anamorphic fungi," Fungal Diversity, 2007, vol. 26, No. 10, pp. 1-54.
Smith, T.F. et al., "Identification of Common Molecular Subsequences," Journal of Molecular Biology, 1981, vol. 147, pp. 195-197.
Yashiro et al., "Effect of Streptomycin Treatment on Bacterial Community Structure in the Apple Phyllosphere," Plos One, May 21, 2012, vol. 7, No. 5, 10 pages.

\* cited by examiner

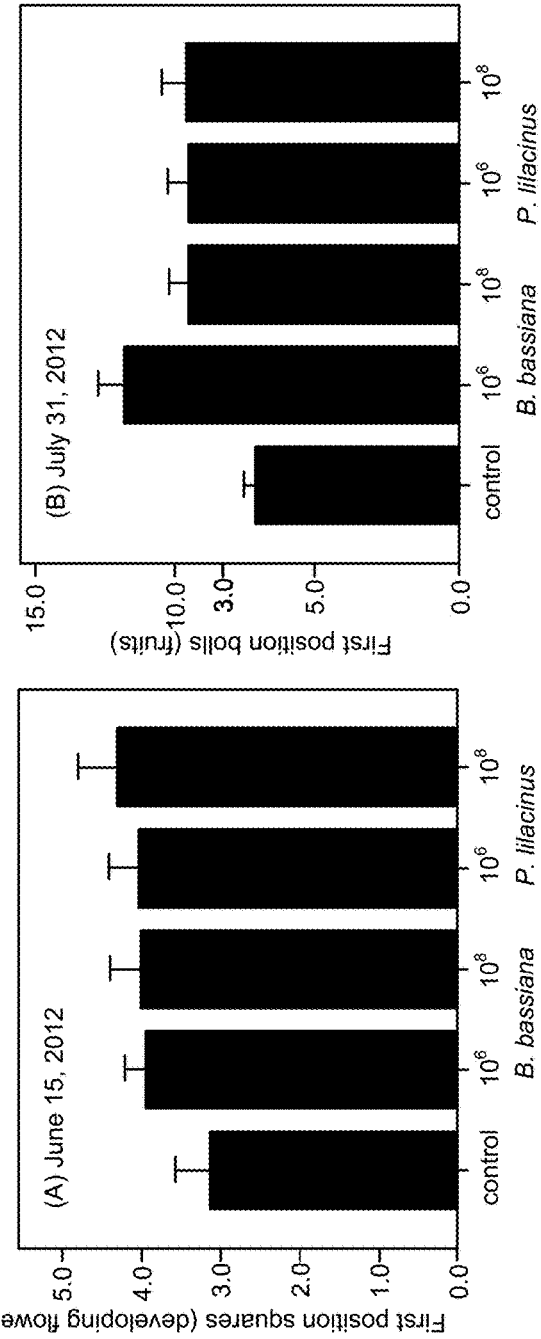
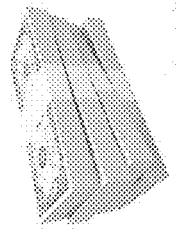
Yields?
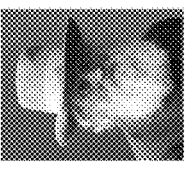
Fitness?
Repeated measures ANOVA (Time, P < 0.001; Time*Endophyte, P=0.045, Endophyte, P=0.003)
Positive effects of endophytes on plant reproductive traits
FIG. 10A
FIG. 10B

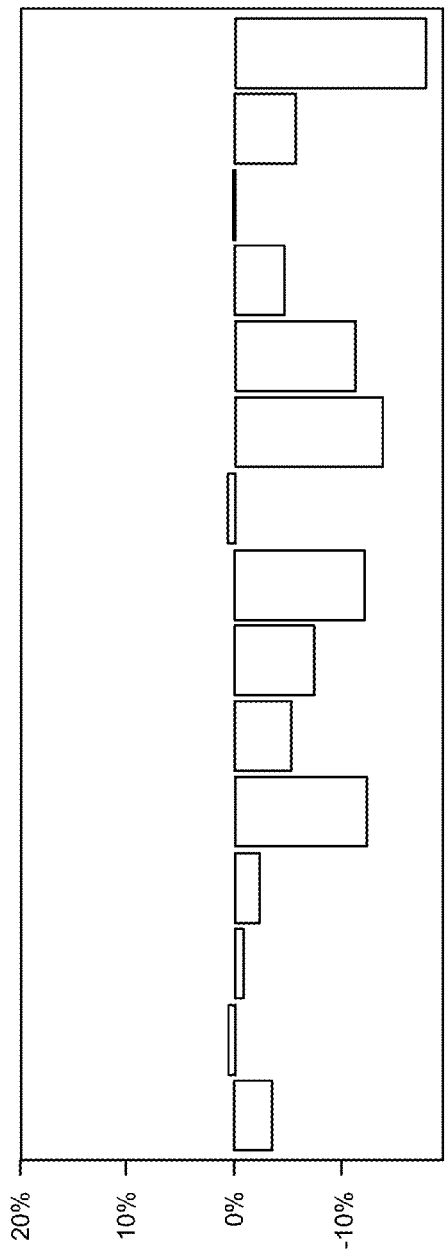
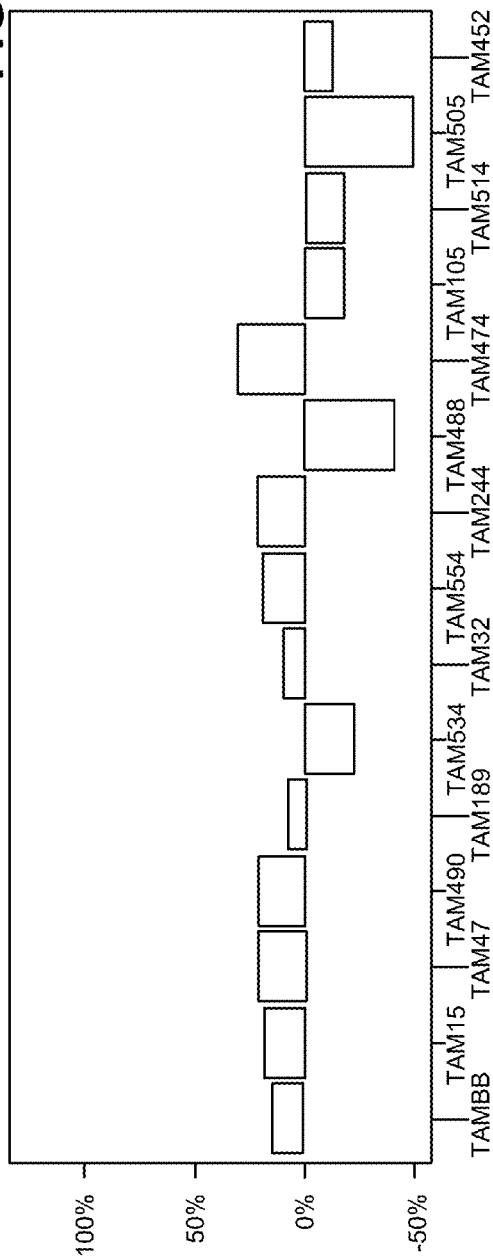
FIG. 16A
FIG. 16B

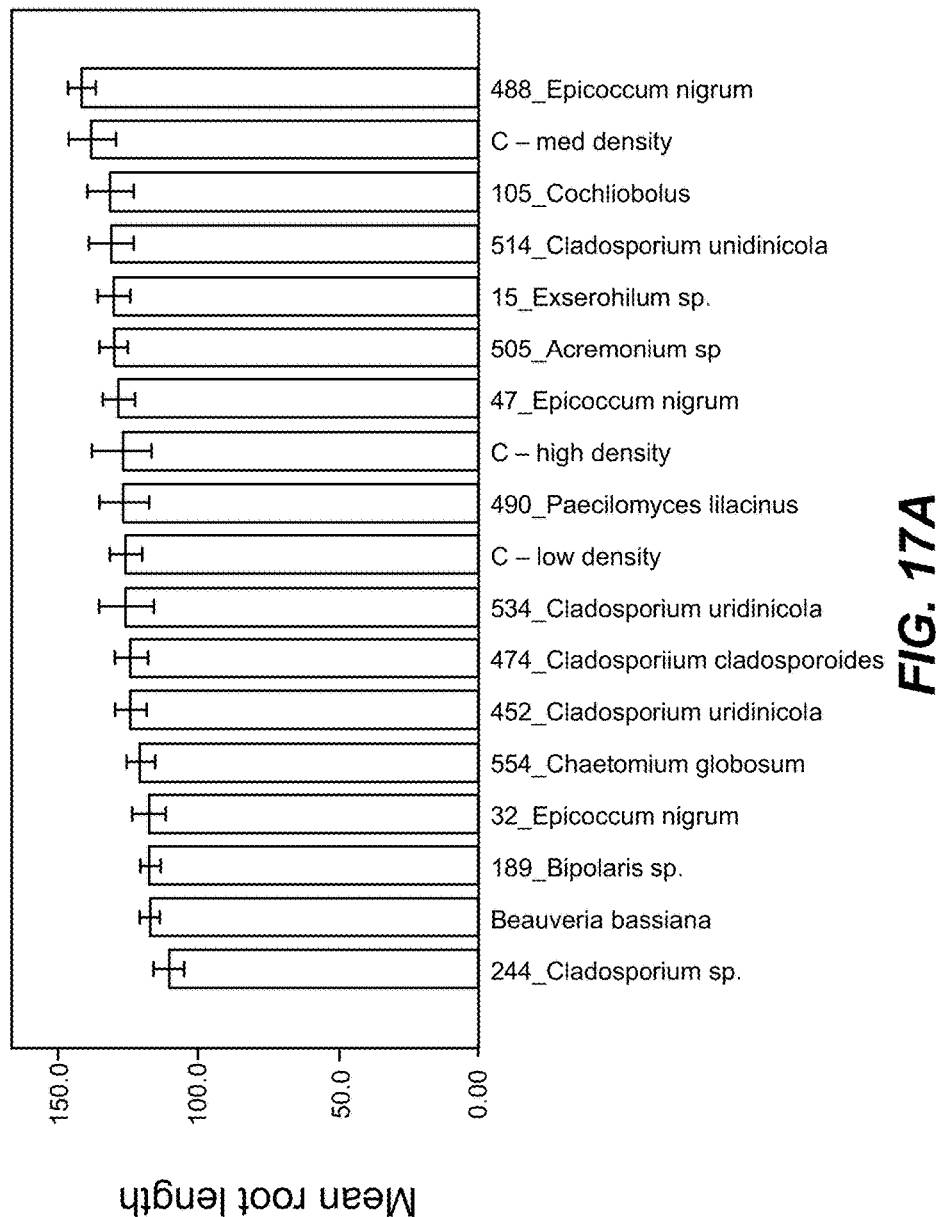

| Genotype | Treatments | Estimate | Std. Error |
|---|---|---|---|
| DTP | 194/Epic | 15.000 | .323 |
|  | 249/Clad | 15.778 | .173 |
|  | 355/Chae | 16.500 | .345 |
|  | 46/Epico | 17.125 | .364 |
|  | 463/Clad | 16.571 | .291 |
|  | 534/Clad | 15.722 | .289 |
|  | 554/Chae | 15.571 | .272 |
|  | 58/Epico | 15.438 | .433 |
|  | control | 16.000 | .296 |
|  | Overall | 15.952 | .116 |
| PHY | 194/Epic | 15.706 | .329 |
|  | 249/Clad | 15.000 | .331 |
|  | 355/Chae | 14.471 | .194 |
|  | 46/Epico | 18.000 | .257 |
|  | 463/Clad | 15.438 | .288 |
|  | 534/Clad | 14.333 | .347 |
|  | 554/Chae | 16.294 | .254 |
|  | 58/Epico | 14.824 | .376 |
|  | control | 16.722 | .289 |
|  | Overall | 15.682 | .135 |
| Overall | Overall | 15.816 | .089 |

*FIG. 24*

| Genotype | Treatments | Estimate | Std. Error |
|---|---|---|---|
| DTP | 194 | 18.899 | .332 |
|  | 249 | 19.000 | .370 |
|  | 355 | 19.389 | .244 |
|  | 46 | 20.188 | .248 |
|  | 463 | 19.357 | .289 |
|  | 534 | 19.444 | .258 |
|  | 554 | 19.429 | .374 |
|  | 58 | 19.563 | .343 |
|  | control | 20.286 | .294 |
|  | Overall | 19.479 | .107 |
| PHY | 194 | 19.176 | .246 |
|  | 249 | 18.357 | .341 |
|  | 355 | 17.647 | .363 |
|  | 46 | 20.353 | .171 |
|  | 463 | 19.125 | .340 |
|  | 534 | 18.200 | .279 |
|  | 554 | 19.529 | .244 |
|  | 58 | 19.706 | .319 |
|  | control | 19.667 | .354 |
|  | Overall | 19.115 | .118 |
| Overall | Overall | 19.296 | .080 |

*FIG. 25*

SEQUENCE LISTING

<160> NUMBER OF SEQ ID NOS: 77

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
cggcggactc gccccagccc g                                         21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
ccgcgtcggg gttccggtgc g                                         21

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ctcagttgcc tcggcgggaa                                           20

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
gtgcaactca gagaagaaat tccg                                      24

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 5
tccgtaggtg aacctgcg                                             18

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gctgcgttct tcatcgatgc                                           20

<210> SEQ ID NO 7
<211> LENGTH: 225
<212> TYPE: DNA
<213> ORGANISM: Acremonium alternatum

<400> SEQUENCE: 7
gggtacataa actcccaaac cattgtgaac ttaccactgt tgcttcggcg gcctcgcccc    60
gggcgcgttc gcgcggcccg gacccaggcg tccgcggag gctccaaact cttgtctttt    120
agtgtatttc tgagtggcat aagcaaataa atcaaaactt tcagcaacgg atctcttggt   180
tctggcatcg atgaagaacg cagcaggact aacgtgtgtc gacgg              225

<210> SEQ ID NO 8
<211> LENGTH: 225
<212> TYPE: DNA
<213> ORGANISM: Alternaria alternata

<400> SEQUENCE: 8
gccaatgaac acctgcggag ggatcattac acaaatatga aggcgggctg gacctctcgg    60
ggttacagcc ttgctgaata atccccttg tcttttgcgt acttcttgtt tccttggtgg    120
gttcgcccac cactaggaca aacataaacc ttttgtaatt gcaatcagcg tcagtaacaa    180
attaataatt acaactttca acaacggatc tcttggttct ggcat                    225

<210> SEQ ID NO 9
<211> LENGTH: 240
<212> TYPE: DNA
<213> ORGANISM: Alternaria brassicae

<400> SEQUENCE: 9
gactttcata gtaggaggag cgggctggaa tcaccctctc gggggtaca gccttgctga    60 attatttcac cctgtctttt tgcgtacttc ttgtttcctt ggtgggttcg cccaccacta    120
ggacaaacat aaaccttttg taattgcaat cagcgtcagt aacaaattaa taattacaac    180
tttcaacaac ggatctcttg gttctggcat cgatgaagaa cgcacagtca gtgtgaaatc    240

<210> SEQ ID NO 10
<211> LENGTH: 224
<212> TYPE: DNA
<213> ORGANISM: Alternaria compacta

<400> SEQUENCE: 10
tgcgtatgtc cgacatatca ggcgggctgg acctctcggg gttacagcct tgctgaatta    60
ttcacccctt gtcttttgcg tacttcttgt tccttggtg ggttcgccca ccactaggac    120
aaacataaac cttttgtaat tgcaatcagc gtcagtaaca aattaataat tacaactttc    180
aacaacggat ctcttggttc tggcatcgat gaaaaacgca tcaa                     224

<210> SEQ ID NO 11
<211> LENGTH: 297
<212> TYPE: DNA
<213> ORGANISM: Alternaria dianthi

<400> SEQUENCE: 11
cctccggact ggctcgagga ggttggcaac gaccacctca agccggaaag ttggtcaaac    60
tcggtcattt agaggaagta aaagtcgtaa caatttctcc gtaggtgaac ctgcggaggg    120
atcattacac aggtatgaag gcgggctgga atctctcggg gttacagcct tgctgaatta    180
ttcacccgtg tcttttgcgt acttcttgtt tcctgggtgg gttcgcccac caccaggacc    240
aaccataaac cttttgtaat tgcaatcagc gtcagtaaca aaataataat tacaact       297

<210> SEQ ID NO 12
<211> LENGTH: 249
<212> TYPE: DNA
<213> ORGANISM: Alternaria longipes

<400> SEQUENCE: 12
tggtaattac aaaatgaagc gggctggacc tctcggggtt acagcctgct gaattattca    60
cccttgtctt ttgcgtactt cttgtttcct tggtgggttc gcccaccact aggacaaaca    120

```
taaacctttt gtaattgcaa tcagcgtcag taacaaatta ataattacaa ctttcaacaa      180
cggatctctt ggttctggca tcgatgaaga acgcagcaaa ttaatgccgg ctggaacgcc      240
tctgggata                                                             249

<210> SEQ ID NO 13
<211> LENGTH: 227
<212> TYPE: DNA
<213> ORGANISM: Alternaria mali

<400> SEQUENCE: 13
atcgtggagg tcaggactat tacacatatg aaggcgggct ggaacctctc ggggttacag       60
ccttgctgaa ttattcaccc ttgtcttttg cgtacttctt gtttccttgg tgggttcgcc      120
caccactagg acaaacataa accttttgta attgcaatca gcgtcagtaa caaattaata      180
attacaactt ccacaacgg gatctcttgg gttctggcat cgctagc                    227

<210> SEQ ID NO 14
<211> LENGTH: 210
<212> TYPE: DNA
<213> ORGANISM: Alternaria sesami

<400> SEQUENCE: 14
aggcgggctg gcacctctcg ggtggccag ccttgctgaa ttattccacc cgtgtctttt       60
gcgtacttct tgtttccttg gtgggctcgc ccaccacaag gaccaaccca taaacctttt      120
tgtaatggca atcagcgtca gtaacaatgt aataattaca actttcaaca acggatctct      180
tggttctggc atcgatgaag aacgcagcaa                                      210

<210> SEQ ID NO 15
<211> LENGTH: 256
<212> TYPE: DNA
<213> ORGANISM: Alternaria solani

<400> SEQUENCE: 15
atgtgtcatg gtatgaggcg ggctggacct ctcggggtta cagccttgct gaattattca       60
cccttgtctt ttgcgtactt cttgtttcct tggtgggttc gcccaccact aggacaaaca      120
taaacctttt gtaattgcaa tcagcgtcag taacaaatta ataattacaa ctttcaacaa      180
cggatctctt ggttctggca tcgatgaaga acgcagcgaa atgcgataag tagtgtgaat      240
tgcagaattc agtaat                                                     256

<210> SEQ ID NO 16
<211> LENGTH: 263
<212> TYPE: DNA
<213> ORGANISM: Alternaria sp.

<400> SEQUENCE: 16
aggcgggctg gacctctcgg ggttacagcc ttgctgaatt attcacccTT gtcttttgcg       60
tacttcttgt ttccttggtg ggttcgccca ccactaggac aaacataaac cttttgtaat      120
tgcaatcagc gtcagtaaca aattaataat tacaactttc aacaacggat ctcttggttc      180
tggcatcgat gaagaacgca gctaaataca tatgaaggcg ggctggaacg tcccgcggtt      240
gcagacttgc tgacttattc acc                                             263

<210> SEQ ID NO 17
<211> LENGTH: 204
<212> TYPE: DNA
```

<213> ORGANISM: Alternaria tenuissima

<400> SEQUENCE: 17

| tgaggcgggc tggacctctc ggggttacag ccttgctgaa ttattcaccc ttgtcttttg | 60 |
| cgtacttctt gtttccttgg tgggttcgcc caccactagg acaaacataa acctttgta | 120 |
| attgcaatca gcgtcagtaa caaattaata attacaactt tcaacaacgg atctcttggt | 180 |
| tctggcatcg atgaagaacg cagc | 204 |

<210> SEQ ID NO 18
<211> LENGTH: 244
<212> TYPE: DNA
<213> ORGANISM: Bipolaris spicifera

<400> SEQUENCE: 18

| acgaaggccg ttcgcggctg gactatttat taccccttgtc ttttgcgcac ttgttgtttc | 60 |
| ctgggcgggt tcgctcgcca ccaggaccac aatataaacc ttttttatgc agttgcaatc | 120 |
| agcgtcagta taacaaatgt aaatcattta caactttcaa caacggatct cttggttctg | 180 |
| gcatcgatga agaacgcagc aatacacact caataaaaaa cgaaggccgt tcgcggacgg | 240 |
| acta | 244 |

<210> SEQ ID NO 19
<211> LENGTH: 246
<212> TYPE: DNA
<213> ORGANISM: Cercospora canescens

<400> SEQUENCE: 19

| cttcggtgcg cttcccctttt ggggggactttt gggagggatc attactgagt gagggccttc | 60 |
| gggctcgacc tccaacccctt tgtgaacaca acttgttgct tcggggggcga ccctgccgtt | 120 |
| tcgacggcga gcgcccccgg aggccttcaa acactgcatc tttgcgtcgg agtttaagta | 180 |
| aattaaacaa aactttcaac aacggatctc ttggttctgg catcgatgaa gaacgcagcg | 240 |
| aaatgc | 246 |

<210> SEQ ID NO 20
<211> LENGTH: 280
<212> TYPE: DNA
<213> ORGANISM: Cercospora capsici

<400> SEQUENCE: 20

| gactagctac ataggcttcg ggctcgacct ccaccctttg tgaacacaac ttgttgcttc | 60 |
| gggggcgacc ctgccgtttc gacggcgagc gcccccggag gccttcaaac actgcatctt | 120 |
| tgcgtcggag tttaagtaaa ttaaacaaaa ctttcaacaa cggatctctt ggttctggca | 180 |
| tcgatgaaga acgcagcaga aatgcgataa gtaatgtgaa ttgcagaatt cagtgaatca | 240 |
| tcgaatcttt gaacgcacat tgcgcccctt ggtattccga | 280 |

<210> SEQ ID NO 21
<211> LENGTH: 220
<212> TYPE: DNA
<213> ORGANISM: Cercospora kikuchii

<400> SEQUENCE: 21

| cgtagggtga acctgcggag ggatcattac tgagtgaggg ccttcgggct cgacctccaa | 60 |
| ccctttgtga acacaacttg ttgcttcggg ggcgaccctg ccgttcgac ggcgagcgcc | 120 |
| cccggaggcc ttcaaacact gcatctttgc gtcggagttt aagtaaatta acaaaaactt | 180 |

```
tcaacaacgg atctcttggt tctggcatcg atgaagaacg                          220
```

<210> SEQ ID NO 22
<211> LENGTH: 243
<212> TYPE: DNA
<213> ORGANISM: Cercospora zinnia

<400> SEQUENCE: 22

```
tcgattgaat ggctcagtga ggccttcgga ctggcccagg gaggtcggca acgaccaccc    60
agggccggaa agttggtcaa actcggtcat ttagaggaag taaaagtcgt aacaaggtct   120
ccgtaggtga acctgcggag ggatcattac tgagtgaggg ccttcgggct cgacctccaa   180
cccttgtga acacaacttg ttgcttcggg ggcgaccctg ccgtttcgac ggcgatcact    240
tgt                                                                 243
```

<210> SEQ ID NO 23
<211> LENGTH: 291
<212> TYPE: DNA
<213> ORGANISM: Chaetomium globosum

<400> SEQUENCE: 23

```
aaactcccta accattgtga acgttaccta taccgttgct tcggcgggcg ccccggggt    60
ttacccccg ggcgcccctg ggccccaccg cgggcgcccg ccggaggtca ccaaactctt   120
gataatttat ggcctctctg agtcttctgt actgaataag tcaaaacttt caacaacgga   180
tctcttggtt ctggcatcga tgaagaacgc agccatcatt agagagttgc aaactcccta   240
aaccccttgtg aacgtaacct ataccgttgc gttcggcggg cggccccccgg g          291
```

<210> SEQ ID NO 24
<211> LENGTH: 263
<212> TYPE: DNA
<213> ORGANISM: Chaetomium piluliferum

<400> SEQUENCE: 24

```
cattacagag ttgcaaaact ccctaaacca ttgtgaacgt taccttcaaa ccgttgcttc    60
ggcgggcggc cccgctccgc ccggtgcccc ctggcccccct agcggggcgc cgccggagg    120
aaaacccaac tcttgattat aatggcctct ctgtctcttc tgtactgaat aagtcaaaac   180
tttcaacaac ggatctcttg gttctggcat cgatgaagaa cgcagcgaaa tgcgataagt   240
aatgtgaatt gcagaattca gtg                                           263
```

<210> SEQ ID NO 25
<211> LENGTH: 210
<212> TYPE: DNA
<213> ORGANISM: Chaetomium sp.

<400> SEQUENCE: 25

```
ctccctaacc attgtgaacg ttacctaaac cgttgcttcg gcgggcggcc ccggggttta    60
ccccccgggc gccctgggc cccaccgcgg gcgcccgccg gaggtcacca aactcttgat   120
aatttatggc ctctctgagt cttctgtact gaataagtca aaactttcaa caacggatct   180
cttggttctg gcatcgatga aaacgcagc                                     210
```

<210> SEQ ID NO 26
<211> LENGTH: 255
<212> TYPE: DNA
<213> ORGANISM: Cladosporium cladosporioides

```
<400> SEQUENCE: 26
tctaccaccg ggatgttcat aacccttttgt tgtccgactc tgttgcctcc ggggcgaccc    60
tgccttcggg cggggctcc gggtggacac ttcaaactct tgcgtaactt tgcagtctga    120
gtaaatttaa ttaataaatt aaaacttttta acaacggatc tcttggttct ggcatcgatg   180
aagaacgcag ccaaaccagc aaacccggtc taacccccgg gatgttcatg acccttttgtt   240 gtccgactct gaggc                                                    255

<210> SEQ ID NO 27
<211> LENGTH: 240
<212> TYPE: DNA
<213> ORGANISM: Cladosporium sp.

<400> SEQUENCE: 27
actgcttcat tacaacaacg cccgggcttc ggcctggtta ttcaaaaccc tttgttgtcc    60
gactctgttg cctccgcggc gaccctgcct tcgggcgggg gctccgggtg gacacttcaa   120
actcttgcgt aactttgcag tctgagtaaa cttaattaat aaattaaaac ttttaacaac   180
ggatctcttg gttctggcat cgatgaagaa cggagcgaaa tgcgataagt aatgaattgc   240

<210> SEQ ID NO 28
<211> LENGTH: 226
<212> TYPE: DNA
<213> ORGANISM: Cladosporium uredinicola

<400> SEQUENCE: 28
ggtctaccac cgggatgttc ataccccttt gttgtccgac tctgttgcct ccggggcgac    60
cctgccttcg gcggggggct ccgggtggac acttcaaact cttgcgtaac tttgcagtct   120
gagtaaactt aattaataaa ttaaaacttt taacaacgga tctcttggtt ctggcatcga   180
tgaagaacgc agcgaaaatc aagtgggtct gcccccgcga tgggat                  226

<210> SEQ ID NO 29
<211> LENGTH: 250
<212> TYPE: DNA
<213> ORGANISM: Cochliobolus sp

<400> SEQUENCE: 29
gctaattaac caataaccta tgaaggctgt acgccgctgc gccccggcc agttggctga     60 ggctggatta tttattaccc cttgtctttt gcgcacttgt tgtttcctgg gcgggttcgc   120
ccgcctccag gaccacacca taaaccttttt ttatgcagtt gcaatcagcg tcagtacaac   180
aaatgtaaat catttacaac tttcaacaac ggatctcttg gttctggcat cgatgaagaa   240
ccgcaacagc                                                          250

<210> SEQ ID NO 30
<211> LENGTH: 249
<212> TYPE: DNA
<213> ORGANISM: Phanerochaete crassa

<400> SEQUENCE: 30
ggttgtagct ggcctcatac tgggcatgtg cacacctggc tcatccactc cttaacctct    60
gtgcactttt tgtaggctct ggttgaaagg cgttgcttca cttcggtgtg gtaatcgctg   120
gaagacctgg tctatgtttt attacaaacg cttcagttat acaatgtttta tctgcgtata   180 acgcatttat atacaacttt cagcaacgga tctcttggct ctcgcatcga tgaagaacgc   240
agctcgagt                                                           249
```

<210> SEQ ID NO 31
<211> LENGTH: 267
<212> TYPE: DNA
<213> ORGANISM: Phoma americana

<400> SEQUENCE: 31

```
cgtacgctac atggaagtaa aagtagtaac aaggtttccg taggtgaacc tgcggaagga      60
tcattaccta gagttgtagg ctttgcctgc tatctcttac ccatgtcttt tgagtacctt     120
cgtttcctcg gcgggtccgc cgccgattg acaatttaa accatttgca gttgcaatca      180
gcgtctgaaa aaacttaata gttacaactt tcaacaacgg atctcttggt tctggcatca     240
atgaaaaacg cagcaacaca aaattac                                          267
```

<210> SEQ ID NO 32
<211> LENGTH: 205
<212> TYPE: DNA
<213> ORGANISM: Phoma subherbarum

<400> SEQUENCE: 32

```
tacgtgcagc gctttgcctg ctatctctta cccatgtctt ttgagtacct tcgtttcctc      60
ggcgggtccg cccgccgatt ggacaattta aaccatttgc agttgcaatc agcgtctgaa     120
aaaaacttaa tagttacaac tttcaacaac ggatctcttg gttctggcat cgatgaagaa     180
cgcagcttac ctagagaatg cgtgt                                            205
```

<210> SEQ ID NO 33
<211> LENGTH: 264
<212> TYPE: DNA
<213> ORGANISM: Phomopsis liquidambari

<400> SEQUENCE: 33

```
aggcgcaccc agaaaccctt tgtgaactta taccttactg ttgcctcggc gcatgctggc      60
ccctcggggt tccctggag acaggagca ggcacgccgg cggccaagtt aactcttgtt      120
tttacactga aactctgaga aaaaaacaca aatgaatcaa actttcaac aacggatctc     180 ttggttctgg catcgatgaa gaacgcacaa gtggagggcc ccaggcgccc cccaaaacc     240 tttttttgagt tattacttac tgtt                                            264
```

<210> SEQ ID NO 34
<211> LENGTH: 222
<212> TYPE: DNA
<213> ORGANISM: Phomopsis sp.

<400> SEQUENCE: 34

```
ccggcgcacc cagaaaccct tgtgaactt atacctactg ttgcctcggc gcaggccggc      60
cttttgtcaa aaaaggcccc ctggagacag ggagcagccc gccggcggcc aaccaaactc     120
ttgtttctac agtgaatctc tgaggaaaaa acataaatga atcaaaactt tcaacaacgg     180
atctcttggt tctggcatcg atgaagaacg cagcatgctg gc                         222
```

<210> SEQ ID NO 35
<211> LENGTH: 255
<212> TYPE: DNA
<213> ORGANISM: Pleospora sp.

<400> SEQUENCE: 35

```
cgggttggga cctcacctcg gtgagggctc cagcttgtct gaattattca cccatgtctt      60
```

```
ttgcgcactt cttgtttcct gggcgggttc gcccgccacc aggaccaaac cataaacctt      120
tttgtaattg caatcagcgt cagtaaacaa tgtaattatt acaactttca acaacggatc      180
tcttggttct ggcatcgatg aagaacgcag cgaaatgcga tacgtagtgt gaattgcaga      240
attcagtgat tttgc                                                      255

<210> SEQ ID NO 36
<211> LENGTH: 349
<212> TYPE: DNA
<213> ORGANISM: Pleosporaceae sp.

<400> SEQUENCE: 36
ggatcattac acaatatgaa ggcgggctgg aacctctcgg ggttacagcc ttgctgaatt      60 attcacccctt gtcttttgcg tacttcttgt ttccttggtg ggttcgccca ccactaggac    120
aaacataaac cttttgtaat tgcaatcagc gtcagtaaca aattaataat taccactttc    180
aacaacggga tctcttggtt ctgggcatcg agcagaaaaa cgcagaattg aaggcgggct    240
gggaacctct tcgggggggt ccagggcttt ggtgaattat tcaccccttg cctttgcgta    300
cgttgtttgt tttccttggg gggggtaggc acacaaaaaa agaaaacgg                 349

<210> SEQ ID NO 37
<211> LENGTH: 222
<212> TYPE: DNA
<213> ORGANISM: Preussia africana

<400> SEQUENCE: 37
aagtaccatt atcgtagggc ttcggccctg tcgagataga acccttgcct ttttgagtac      60
cttttcgttt cctcggcagg ctcgcctgcc aatggggacc ccaacaaaca ctttgcagta    120
cctgtaaaca gtctgaacaa acttttaaaa attaaaactt tcaacaacgg atctcttggt    180
tctggcatcg atgaagaacg cagcgaaatg cgataaaacg tg                        222

<210> SEQ ID NO 38
<211> LENGTH: 218
<212> TYPE: DNA
<213> ORGANISM: Preussia sp.

<400> SEQUENCE: 38
ttcgagatac acccttgcct ttttgagtac cttttcgttt cctcggcagg ctcgcctgcc      60
aacggggacc cttcaaaacg ctttgtaata cctgtaactg tctgatataa caagcaaaaa    120
tcaaaacttt caacaacgga tctcttggtt ctggcatcga tgaagaacgc agcaatcgtt    180
gggcttcggc ccattagaga taacacccctt gcctttttt                           218

<210> SEQ ID NO 39
<211> LENGTH: 254
<212> TYPE: DNA
<213> ORGANISM: Pseudozyma sp.

<400> SEQUENCE: 39
acatctcgcg gttcagcctt gttgagtatt caccccttgtt ttttgcggag aaatgtttgg     60
gtggagggag caccagcacc aagacaaatc taaaccttt gcaattgcaa tacgggcgac     120
atttacctta ataattgttg atttcataag attatatctt ggttgaaact ccactggtaa    180
tgccatcgtc taaaatctaa aaacaacttt tggcaacgga tctcttggtt ctcgcatcga    240
tgaagaacgc agcc                                                       254
```

<210> SEQ ID NO 40
<211> LENGTH: 277
<212> TYPE: DNA
<213> ORGANISM: Pyrenophora teres

<400> SEQUENCE: 40
aggcagattg ggtagtcccc gcttttgggg tttgcccatt ctggcgccat attcacccat 60
gtcttttgcg tactacttgt ttccttggcg ggttcgcccg ccaattggac tttattcaac 120
cctttttttt ttattgcaat cagcgtcagc aaaacaatgt aatcaattta caactttcaa 180
caacggatct cttggttctg gcatcgatga aaaacgcagc cacaatatga tggccgatgg 240
ggcaggcctc ttttggggtt gccccctctg gcgccct 277

<210> SEQ ID NO 41
<211> LENGTH: 289
<212> TYPE: DNA
<213> ORGANISM: Colletotrichum capsici

<400> SEQUENCE: 41
gctcatcacc ctttgtgaca taccttaact gttgcttcgg cgggtaggcg tcccctgaaa 60
aggacgtctc ccggccctct cccgtccgcg ggtggggcgc ccgccggagg ataaccaaac 120
tctgatttaa cgacgtttct tctgagtgac acaagcaaat aatcaaaact tttaacaacg 180
gatctcttgg ttctggcatc gatgaagaac gcagcaatta ttggggtgtt gctcatcatc 240
ctttgtggtg aaccttaact gttgctgcgg cggggggcgg cgtcccctg 289

<210> SEQ ID NO 42
<211> LENGTH: 216
<212> TYPE: DNA
<213> ORGANISM: Coniolariella gamsii

<400> SEQUENCE: 42
tgacactccc aaaacccctg tgaacatacc gtacgttgcc tcggcggggg ggcgctcccc 60
ccccgccggc ggcccacgaa actctgtttt gccctgaatc tctgaaacga caaactaaat 120
cagttaaaac tttcaacaac ggatctcttg gttctggcat cgatgaagaa cgcagcgaaa 180
tatagaagtg acccaactcc taaccactgt gaacaa 216

<210> SEQ ID NO 43
<211> LENGTH: 268
<212> TYPE: DNA
<213> ORGANISM: Coniothyrium aleuritis

<400> SEQUENCE: 43
tagacttcac taaagcttgt agacttcggt ctgctacctc ttacccatgt cttttgagta 60
ccttcgtttc ctcggcgggt ccgcccgccg attggacaac attcaaaccc tttgcagttg 120
caatcagcgt ctgaaaaaac ataatagtta caactttcaa caacggatct cttggttctg 180
gcatcgatga agaacgcagc gaaatgcgat aagtagtgtg aattgcagaa ttcagtgaat 240
catcgaatct ttgaacgcac attgcgcc 268

<210> SEQ ID NO 44
<211> LENGTH: 210
<212> TYPE: DNA
<213> ORGANISM: Coniothyrium sp.

<400> SEQUENCE: 44
gggctggatc tctcggggtt acagccttgc tgaattattc acccttgtct tttgcgtact 60

```
tcttgtttcc ttggtgggtt cgcccaccac taggacaaac ataaacctttt tgtaattgca      120 atcagcgtca gtaacaaatt aataattaca actttcaaca acggatctct tggttctggc      180
atcgatgaag aacgcagcaa cactaatatg                                       210
```

<210> SEQ ID NO 45
<211> LENGTH: 218
<212> TYPE: DNA
<213> ORGANISM: Corynespora cassiicola

<400> SEQUENCE: 45

```
cgccccttcg agatagcacc ctttgtttat gagcacctct cgtttcctcg gcaggctcgc      60
ctgccaacgg ggacccacca caaacccatt gtagtacaag aagtacacgt ctgaacaaaa     120
caaaacaaac tatttacaac tttcaacaac ggatctcttg gttctggcat cgatgaagaa     180
cgcagcggat atcgtagggg ccgcgccccc ttccagat                             218
```

<210> SEQ ID NO 46
<211> LENGTH: 204
<212> TYPE: DNA
<213> ORGANISM: Diaporthe sp.

<400> SEQUENCE: 46

```
acccttttgtg aacttatacc taccgttgcc tcggcgcagg ccggcccccc tcaccggggg     60
ccccccggag acggggagca gcccgccggc ggccaaccaa actcttgttt cttagtgaat    120
ctctgagtaa aaatcataaa tgaatcaaaa cttcaacaa cggatctctt ggttctggca    180
tcgatgaaga acgcagcaag ttgc                                            204
```

<210> SEQ ID NO 47
<211> LENGTH: 281
<212> TYPE: DNA
<213> ORGANISM: Diatrype sp.

<400> SEQUENCE: 47

```
ccatgtgaac ttacctttgt tgcctcggcg ggagagccta cccggtacct accctgtagt      60
tacccgggag cgagctaccc tgtagcccgc tgctggccga cccgccggtg gacagtaaaa    120 ctcttgttttt ttagtgatta tctgagtgtt tatacttaat aagttaaaac tttcaacaac    180
ggatctcttg gttctggcat cgatgaagaa cgcagccaat acagagttat cttctcccag    240
cccatgtgaa cttaccttttg ttgccccggc gggagagcct a                        281
```

<210> SEQ ID NO 48
<211> LENGTH: 338
<212> TYPE: DNA
<213> ORGANISM: Drechslerella dactyloides

<400> SEQUENCE: 48

```
ggttagaaac tgttgtttcg gcgggatctc tgccccgggg gcgtcgcagc cccggaccaa      60 ggggggccgcc ggaggaccaa ccaaaactct ttttgtatac cccctcgcgg gttttttttta  120 taatctgagc cttctcggcg cctctcgtag gcgtttcgaa aatgaatcaa aacttttaaa    180
aacggatctc ttggttctgg catcggatga agaacgcaga gaaatgcgat aagtaatgtg    240
aattgcagaa ttcactgaat catctaatct ttgaacggac attgcgcccg ccagttttct    300
ggcgggcatg cctgtccgag cgtcatttca accctcga                             338
```

<210> SEQ ID NO 49
<211> LENGTH: 247

```
<212> TYPE: DNA
<213> ORGANISM: Embellisia indefessa

<400> SEQUENCE: 49
gcatcgatac ctgatccgag gtcaaaagtt gaaaaaaggc tttgtggatg ctgaccttgg      60
ctggaagaga gcgcgacttg tgctgcgctc cgaaaccagt aggccggctg caatgacttt     120
aaggcgagtc tccagcgaac tggagacaag acgcccaaca ccaagcaaag cttgagggta     180
caaatgacgc tcgaacaggc atgccctttg gaataccaaa gggcgcaatg tgcgttcaaa     240
aaaagca                                                               247

<210> SEQ ID NO 50
<211> LENGTH: 207
<212> TYPE: DNA
<213> ORGANISM: Epicoccum nigrum

<400> SEQUENCE: 50
ttgtagactt cggtctgcta cctcttaccc atgtcttttg agtaccttcg tttcctcggc      60
gggtccgccc gccgattgga caacattcaa acccttttgca gttgcaatca gcgtctgaaa   120
aaacataata gttacaactt tcaacaacgg atctcttggt tctggcatcg atgaaaaacg     180
catcacctag agtttgtaga cttcggt                                         207

<210> SEQ ID NO 51
<211> LENGTH: 234
<212> TYPE: DNA
<213> ORGANISM: Epicoccum sp.

<400> SEQUENCE: 51 gtacttaccct acgatttgtg gagttcggtc tgctacctct tacccatgtc tttttaagta    60
ccttcgtttc ctcggcgggt ccgccgccg gttggacaac attcaaaccc tttgcagttg     120
caatcagcgt ctgaaaaaac ttaatagtta caactttcaa caacggatct cttggttctg     180
gcatcgaaca caaacgcagc agcttttagg gacctaccgt ctcctcctct tacc           234

<210> SEQ ID NO 52
<211> LENGTH: 237
<212> TYPE: DNA
<213> ORGANISM: Exserohilum rostratum

<400> SEQUENCE: 52
gctaatttcc ccaccaaact tgtagggtgt ggtttgctgg caacagcgaa ccgccccaag      60 tattttttcac ccatgtcttt tgcgcacttt ttgtttcctg ggccagttcg ctcgccacca   120
ggacccaacc ataaaccttt ttttatgcag ttgcaatcag cgtcagtata ataattcaat     180
ttattaaaac tttcaacaac ggatctcttg gttctggcat cgatgaagaa cgcacaa        237

<210> SEQ ID NO 53
<211> LENGTH: 223
<212> TYPE: DNA
<213> ORGANISM: Fusarium chlamydosporum

<400> SEQUENCE: 53 tcccaaccccc tgtgacatac ctatacgttg cctcggcgga tcagcccgcg ccccgtaaaa    60
cgggacggcc cgcccgagga ccctaaaact ctgtttttag tggaacttct gagtaaaaca    120
aacaaataaa tcaaaacttt caacaacgga tctcttggtt ctggcatcga tgaagaacgc    180
agctcgatga agaacgcagc cccctcccca cgggtgggaa cat                       223
```

<210> SEQ ID NO 54
<211> LENGTH: 258
<212> TYPE: DNA
<213> ORGANISM: Fusarium sp.

<400> SEQUENCE: 54

```
cactcccaac ccatgtgaac ttatctctttt gttgcctcgg cgcaagctac ccgggacctc    60
gcgccccggg cggcccgccg gcggacaaac caaactctgt tatcttagtt gattatctga   120
gtgtcttatt taataagtca aaactttcaa caacggatct cttggttctg gcatcgatga   180
agaacgcagc aaatcattac agaattatcc aactcccaaa cccatgtgaa cttttctttt   240
tgttgcctcg gcgcaagc                                                 258
```

<210> SEQ ID NO 55
<211> LENGTH: 236
<212> TYPE: DNA
<213> ORGANISM: Gibellulopsis nigrescens

<400> SEQUENCE: 55

```
atactcataa ccctttgtga ccttcatacc tgttgcttcg gcggcgcgcc tctcggggcg    60
tgcccgccgg cattatcaga atctctgttc gaacccgacg atacttctga gtgttctaag   120
cgaactgtta aaactttcaa caacggatct cttggctcca gcatcgatga agaacgcagc   180
aaatgagggg tactactctc acccccctttt ggcctcttcc cacttgttgc ttcggc      236
```

<210> SEQ ID NO 56
<211> LENGTH: 243
<212> TYPE: DNA
<213> ORGANISM: Gnomoniopsis sp.

<400> SEQUENCE: 56

```
cgggtgctac ccagaaaccc tttgtgaatt attctcattg ttgcctcggc attgactggc    60
ctcttctgga ggtccctttt ccttcgggga aaggagcagg tcggccggtg cccctataaa   120
ctctttgttt ttacagtgta tcttctgagt aaacaactat aaatgaatca aaacttttaa   180
caacggatct cttggttctg gcatcgatga agaacgcagc aatggaacaa acgccctccg   240
ggg                                                                 243
```

<210> SEQ ID NO 57
<211> LENGTH: 251
<212> TYPE: DNA
<213> ORGANISM: Lewia infectoria

<400> SEQUENCE: 57

```
gcgggctgga cacccccagc cgggcactgc ttcacggcgt gcgcggctgg gccggccctg    60
ctgaattatt cacccgtgtc ttttgcgtac ttcttgtttc ctgggtgggc tcgcccgcca   120
tcaggaccaa ccacaaacct tttgcaatag caatacggt cagtaacaac gtaattaatt    180
acaactttca acaacggatc tcttggttct ggcatcgatg aagaacgtag cgaaatgcga   240
tacgtagtgt g                                                        251
```

<210> SEQ ID NO 58
<211> LENGTH: 210
<212> TYPE: DNA
<213> ORGANISM: Mycosphaerella coffeicola

<400> SEQUENCE: 58

```
aagtcgtact ggcttcgggc tcgacctcca cccctttgtga acacaacttg ttgcttcggg    60
```

```
ggcgaccctg ccgtttcgac ggcgagcgcc cccggaggcc ttcaaacact gcatctttgc    120
gtcggagttt aagtaaatta acaaaaactt tcaacaacgg atctcttggt tctggcatcg    180
atgaagaacg cagcggtctg cacacatcag                                     210
```

<210> SEQ ID NO 59
<211> LENGTH: 213
<212> TYPE: DNA
<213> ORGANISM: Mycosphaerellaceae sp.

<400> SEQUENCE: 59

```
gaccacggcc ggccgcgcca gcgataatcc tttgtgcccc gacattgttg cctgcctttt     60
gaccctgcct tggggcgggg gctccgggtg gacacttaaa ctcttgcgta actttgcagt    120
ctgagtaaac ttaattaata aattaaaact tttaacaccg gatctcttgg ttctggcatc    180
gatgacaaaa cgcaacaaac gcagcagtta acc                                 213
```

<210> SEQ ID NO 60
<211> LENGTH: 227
<212> TYPE: DNA
<213> ORGANISM: Nigrospora oryzae

<400> SEQUENCE: 60

```
ctcccaaccc atgtgaactt atctctttgt tgcctcggcg caagctaccc gggacctcgc     60
gccccgggcg gcccgccggc ggacaaacca aactctgtta tcttcgttga ttatctgagt    120
gtcttattta ataagtcaaa actttcaaca acggatctct tggttctggc atcgatgaag    180
aacgcagcaa aaacgcagc attatcccac tcccaaaccc gtgggaa                   227
```

<210> SEQ ID NO 61
<211> LENGTH: 216
<212> TYPE: DNA
<213> ORGANISM: Nigrospora sp.

<400> SEQUENCE: 61

```
cccatgtgaa catatctctt tgttgcctcg gcgcaagcta cccgggacct cgcgccccgg     60
gcggcccgcc ggcggacaaa ccaaactctg ttatcttcgt tgattatctg agtgtcttat    120
ttaataagtc aaaactttca acaacggatc tcttggttct ggcatcgatg aagaacgcag    180
cagaaacgct cagccaactc ccagacccgt gtgaag                              216
```

<210> SEQ ID NO 62
<211> LENGTH: 249
<212> TYPE: DNA
<213> ORGANISM: Nigrospora sphaerica

<400> SEQUENCE: 62

```
actcccaaac ccatgtgaac atatctcttt gttgcctcgg cgcaagctac ccgggacctc     60
gcgccccggg cggcccgccg gcggacaaac caaactctgt tatcttcgtt gattatctga    120
gtgtcttatt taataagtca aaactttcaa caacggatct cttggttctg gcatcgatga    180
agaacgcagc aaaaaaaaaa atattccact ccccaagccg gggggaaaa ttttttttt     240 ttttttggg                                                             249
```

<210> SEQ ID NO 63
<211> LENGTH: 223
<212> TYPE: DNA
<213> ORGANISM: Paecilomyces sp.

```
<400> SEQUENCE: 63
aatgcggact cccaaaccac tgtgaacata cccgtaccgt tgcctcggcg ggcggcccca      60
gggcggggcc gcagcctccc cagcggaggc gcccgccgca ggtcgcaaaa ctataactat     120
atttagtggc atctctgagt aacttccaaa caatcaaaac tttcaacaac ggatctcttg    180
gttctggcat cgatgaagaa cgcagccaat acagaacttc gcg                      223

<210> SEQ ID NO 64
<211> LENGTH: 205
<212> TYPE: DNA
<213> ORGANISM: Penicillium citrinum

<400> SEQUENCE: 64
aagtacgtga acgggcaaa cctcccaccc gtgttgcccg aacctatgtt gcctcggcgg      60
gccccgcgcc cgccgacggc ccccctgaac gctgtctgaa gttgcagtct gagacctata    120
acgaaattag ttaaaacttt caacaacgga tctcttggtt ccggcatcga tgaagaacgc    180
agcatctggc atcggctgca attcg                                          205

<210> SEQ ID NO 65
<211> LENGTH: 213
<212> TYPE: DNA
<213> ORGANISM: Retroconis sp.

<400> SEQUENCE: 65
gctatcccaa ccattgtgaa cctacctaca accgttgctt cggcgggcgg ccccgggtct     60 cccccgggcgc ccctccggcc cctcgcgggg gcccgccgga ggtacgcaac cctctgtatt    120
tgcatggcct ctctgagtct ctgtactgaa taagtcaaaa ctttcaacaa cggatctctt   180
ggttctggca tcgatgaaga acgcagcagc tac                                 213

<210> SEQ ID NO 66
<211> LENGTH: 253
<212> TYPE: DNA
<213> ORGANISM: Rhizopycnis sp.

<400> SEQUENCE: 66
gaaatattgg gggtaagttt acgcttaacc aaaccgttcc gtaggtgaac ctgcggaagg     60
atcattatcg atttcggttt acaccgtttt ctacctttgt ctatgcgtac cacacgttcc   120 ctcgggggc ttggcccca ctaggaccaa acataaacct ttggtaatgg caatcggggt    180
ctgaaataat ttaattatta caactttaaa caacggatct ctgggttctg gcatcggtaa   240
aaaaacacag gaa                                                       253

<210> SEQ ID NO 67
<211> LENGTH: 210
<212> TYPE: DNA
<213> ORGANISM: Schizothecium inaequale

<400> SEQUENCE: 67
tgcaactccc aaccattgtg aacctacctc accgttgcct cggcgggtgg ccccacccg      60 ggccgcgccg gccccaccgg gccggcaacc cgtcagagga ccgcaactct tagtcatcat   120
tggcctctct gagtaactta tacaataagt caaaactttc aacaacggat ctcttggttc   180
tggcatcgat gaagaacgca gcaagtctaa                                     210

<210> SEQ ID NO 68
<211> LENGTH: 237
```

<212> TYPE: DNA
<213> ORGANISM: Stagonospora sp.

<400> SEQUENCE: 68

```
ctagctactg gcatggggac tgttagtctg catggtatca ctaccgatga gcagcaggtc      60
ccctgtctat acccttgttt tttgcgtacc tattgtttcc tcggcgggct tgctcgccgg     120
ctggacaaaa tctataacct ttttttaatc ttcaatcagc gtctgaaatt atacataata     180
attacaactt tcaacaacgg atctcttggt tctggcatcg atgaaaaacg cagccaa       237
```

<210> SEQ ID NO 69
<211> LENGTH: 223
<212> TYPE: DNA
<213> ORGANISM: Stemphylium lancipes

<400> SEQUENCE: 69

```
aaatgtggcg cccttttggta ttccaaaggg catgcctgtt cgagcgtcat ttgtaccctc     60
aagctttgct tggtgttggg cgtctttgtc tctcacgaga ctcgccttaa aatgattggc    120
agccgaccta ctggtttcgg agcgcagcac aattcttgca ctttgaatca gccttggttg    180
agcatccatc aagaccacat ttttttaact ttttaccgta cta                      223
```

<210> SEQ ID NO 70
<211> LENGTH: 209
<212> TYPE: DNA
<213> ORGANISM: Thielavia hyrcaniae

<400> SEQUENCE: 70

```
ctaaaccatt gtgaacctac cttctaccgt tgcttcggcg ggcgggcccc agcgcccccc      60
ccggcccccc gcgggcgccc gccggaggat acccaaactc ttgacattag tggcctctct    120
gagtattctt tactgaataa gtcaaaactt tcaacaacgg atctcttggt tctggcatcg    180
atgaagaacg cagcaattta cagagttgc                                      209
```

<210> SEQ ID NO 71
<211> LENGTH: 252
<212> TYPE: DNA
<213> ORGANISM: Thielavia sp.

<400> SEQUENCE: 71

```
aaccattgtg acgttaccct caaaccgttg cttcggcggg cggcccgggt ccgcccggtg      60
ccccctggcc ccctcgcggg gcgcccgccg gaggaaaccc aactcttgat acattatggc    120
ctctctgagt cttctgtact gaataagtca aaactttcaa caacggatct cttggttctg    180
gcatcgatga agaacgcagc gaaatgcgat aagtaatgtg aattgcagaa ttcagtgaat    240
catcgaatct tt                                                        252
```

<210> SEQ ID NO 72
<211> LENGTH: 217
<212> TYPE: DNA
<213> ORGANISM: Ulocladium chartarum

<400> SEQUENCE: 72

```
tgaagcgggc tggcatcctt cggggttaca gccttgctga attattcacc cgtgtctttt      60
gcgtacttct tgtttccttg gtgggttcgc ccaccatagg acaaaccata aacctttgt     120
aattgcaatc agcgtcagta aaaaaattaa taattacaac ttttaacaac ggatctcttg    180
gttctggcat cgatgaagaa cgcagccact tacaaaa                             217
```

<210> SEQ ID NO 73
<211> LENGTH: 219
<212> TYPE: DNA
<213> ORGANISM: Verticillium sp.

<400> SEQUENCE: 73

```
gtacacgata ctcataaccc tttgtgaacc ttcatacctg ttgcttcggc ggcgcgcctc        60
tcggggcgtg cccgccggca ttatcagaat ctctgttcga acccgacgat acttctgagt       120
gttctaagcg aactgttaaa actttcaaca acggatctct tggctccagc atcgatgaag       180
aacgcagcaa ggatcaatga atttctcacc acccaagta                              219
```

<210> SEQ ID NO 74
<211> LENGTH: 477
<212> TYPE: DNA
<213> ORGANISM: Beauveria bassiana

<400> SEQUENCE: 74

```
ccgagttttc aactcccaaa cccttatgtg aactcaccta tcgttgcttc ggcggactcg        60
ccccagccgg acgggactgg accagcggcc cgccggggac ctcaaactct tgtattccag       120
catcttctga atacgccgca aggcaaaaca tatgaatcaa actttcaac aacggatctc        180
ttggctctgg catcgatgaa gaacgcagcg aaatgcgata gtaatgtga attgcagaat        240
ccagtgaatc atcgaatctt tgaacgcaca ttgcgcccgc cagcattctg gcgggcatgc       300
cctttcgagc gtcatttcaa ccctcgaccc ccccttgggg aggtcggcgt tggggacggc       360
agcacaccgc cggccctgaa atggagtggc ggcccgtccg cggcgacctc tgcgtagtaa       420
tacagctcgc accgtaaccc gacgcggcct caccgtaaaa cgacccaact tctgaac          477
```

<210> SEQ ID NO 75
<211> LENGTH: 506
<212> TYPE: DNA
<213> ORGANISM: Aspergillus parasiticus

<400> SEQUENCE: 75

```
ccgagtgtag ggttcctagc gagcccaacc tcccacccgt gtttactgta ccttagttgc        60
ttcggcgggc ccgccattca tggccgccgg gggttctcag ccccgggccc gcgcccgccg       120
gagacaccac gaactctgcc tcatctaatg aagtctgagt tgattgtatc gcaatcactt       180
taaactttca acaatggatc tcttggttcc gggatcaatg agcaacccaa caaaatgcga       240
taactagtgt gaattgcaga attccgtgaa tcatcgagtc tttgaacgca cattgcgccc       300
cctggtattc ctgcggggat gcatgtccga gctgaattgc tgcccatcaa gtacgacttg       360
tgtgttgggt cgtcgtcccc tctccggggg ggacgggccc caaacgcagc tgaggcaccg       420
cggccgatcc tagagggtat gggcgctttg tcacctgatc tataggccag gccggcgcta       480
gcctaaccca aatcaatctt ttacag                                           506
```

<210> SEQ ID NO 76
<211> LENGTH: 451
<212> TYPE: DNA
<213> ORGANISM: Lecanicillium lecanii
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t

```
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t

<400> SEQUENCE: 76
ccggcgtccg gacggcctcg cgccgcccgc ggcccggacc caggcggccg ccggagacct      60
ctaaactctg tattatcagc attttctgaa tccgccgcaa ggcaaaacaa atgaatcaaa     120
actttcaaca acggaacctc ttgggtttcg ggcatcgatg aagaacgcag cgaaatgcga     180
taagtaatgt gaattgcaga attcagtgaa tcatcgaatc tttgaacgca cattgcgccc     240
gccagcattc tggcgggcat gcctgttcga gcgtcatttc aaccctcgac ttcccttttgg    300 ggaaatccgc gttggggaaa cggcagcata cccgccnggc cccgaaatgg gagtggcggc     360
ccggtcccgc ngcgaccctt ctgcgtaagt aatccaactc ggcaccggaa cccnacgtg     420 gccaccccng taaaacaccc aacttccgaa c                                    451

<210> SEQ ID NO 77
<211> LENGTH: 549
<212> TYPE: DNA
<213> ORGANISM: Paecilomyces lilacinus

<400> SEQUENCE: 77
ggagggatca ttaccgagtt tacaactccc aaaccccctg tgaacttata ccattactgt      60
tgcttcggcg ggttattgcc ccggggaagg atagggtgcc gcgaggtgcc ctgcccgccc    120
ccccggaaac aggcgcccgc cggaggactc aaactctgta tttttcttg ttttagtgta     180 tactatctga gtaaaaaaca atataatgaa tcaaaacttt caacaacgga tctcttggtt     240
ctggcatcga tgaagaacgc agcgaaatgc gataagtaat gtgaattgca gaattcagtg     300
aatcatcgaa tctttgaacg cacattgcgc ccgccagtat tctgcgggc atgcctgttc     360 gagcgtcatt tcaaccctca agccccttttg gacttggtgt tggggaccgg cgatggacaa     420
actgtccttt cgccgccccc taaatgactt ggcggcctcg tcgcgccct cctctgcgta     480 gtagcacaca cctcgcaaca ggagcccggc gaatggccac tgccgtaaaa ccccccaact     540
tttttcaga                                                             549
```

FUNGAL ENDOPHYTES FOR IMPROVED CROP YIELDS AND PROTECTION FROM PESTS

CROSS REFERENCE TO RELATED APPLICATIONS

This application is a divisional of U.S. application Ser. No. 14/964,429, filed Dec. 9, 2015, pending, which is a continuation of U.S. application Ser. No. 14/535,292 filed Nov. 6, 2014, now U.S. Pat. No. 9,277,751, which claims priority to U.S. Provisional Patent Application Nos. 61/900,929 and 61/900,935, both filed Nov. 6, 2013, which are herein incorporated by reference in their entirety.

INCORPORATION OF SEQUENCE LISTING

The sequence listing that is contained in the file named 38749_US_Sequence_Listing.txt, includes 77 sequences and is 33 kilobytes as measured in Microsoft Windows operating system and was created on Oct. 2, 2017, is filed electronically herewith and incorporated herein by reference.

FIELD OF THE INVENTION

The present invention relates to fungal endophytes of agricultural crops for improving yield and/or for protection from pests.

DESCRIPTION OF RELATED ART

Fungal endophytes are fungi that internally colonize plant tissues without causing evident damage or disease. Particular fungal endophytes, such as mycorrhiza, survive within various host plant tissues, often colonizing the intercellular spaces of host leaves, stems, flowers or roots. The symbiotic endophyte-host relationships can provide several fitness benefits to the host plant, such as enhancement of nutrition, and/or increased drought tolerance. Root-colonizing mycorrhizae survive on photosynthetic carbohydrates from the plant, and in return, aid in the solubilization and uptake of water and minerals to the host, which can lead to the promotion of seed germination and plant growth. Additionally, the association of a fungal endophyte with a host plant can provide tolerance to a variety of biotic and abiotic stresses. Host growth, fitness promotion and protection are thought to be achieved through multiple beneficial properties of the endophyte-host association. For instance, the endophytic organisms may produce growth-regulating substances to induce biomass production and alkaloids or other metabolites. Additionally, fungal endophytes may directly suppress or compete with disease-causing microbes, protecting the plant from potential pathogens.

SUMMARY OF THE INVENTION

In one aspect, the invention provides methods for improving a trait in an agricultural plant comprising contacting an agricultural seed of said plant with a formulation comprising a purified facultative fungal endophytes of at least one species, wherein the endophytes are capable of producing substances that are beneficial to plants or detrimental to pests or both, and wherein the endophytes are present in the formulation in an amount effective to modulate the colonization frequencies of the endophytes that are native to the agricultural plant grown from the seed compared to a reference seed that is planted in an agricultural environment, and to provide a benefit to the seeds or the agricultural plants grown from the seeds.

In another aspect, the invention provides methods for providing a benefit to an agricultural plant comprising treating said plant, the seed of said plant, or the rhizosphere of said plant or seed with a composition comprising purified facultative fungal endophytes and an agriculturally-acceptable carrier, wherein the endophyte is capable of at least one of: reducing pest reproduction, killing pests, and deterring pests, and wherein the endophyte is present in the composition in an amount effective to provide a benefit to the seeds or the agricultural plants derived from the seeds.

In yet another aspect, the invention provides methods for providing a benefit to an agricultural plant, comprising obtaining a synthetic combination of an agricultural plant seed and a purified facultative fungal endophyte, wherein the endophyte is capable of at least one of: reducing pest reproduction, killing pests, and deterring pests, and wherein the endophyte is present in the synthetic combination in an amount effective to provide a benefit to the seeds or the agricultural plants derived from the seeds.

In another embodiments, methods of producing a plant with a non-naturally occurring ratio of endophytes is provided, where the methods comprise contacting an agricultural seed of the plant with a formulation comprising facultative fungal endophytes of at least one species, wherein endophytes are present in the formulation in an amount effective to modulate the colonization frequencies of the endophytes that are native to the agricultural plant grown from the seed compared to a reference seed that is planted in an agricultural environment, wherein the plant with the non-naturally occurring ratio of endophytes has an improved trait as compared to a plant with a naturally-occurring ratio. In a further aspect, the facultative fungal endophytes are capable of producing substances that are beneficial to plants or detrimental to pests or both.

In another aspect, the invention provides methods for altering the systemic defensive pathway in a plant comprising contacting an agricultural seed of said plant with a formulation comprising a purified facultative fungal endophytes of at least one species, wherein the endophytes are capable of producing substances that are beneficial to plants or detrimental to pests or both, and wherein the endophyte is present in the synthetic combination in an amount effective to modulate the level of at least one phytohormone within an agricultural plant grown from the plant seed, and to provide a benefit to the seeds or the agricultural plants grown from the seeds. In a further aspect, the facultative fungal endophytes are capable of producing substances that are beneficial to plants or detrimental to pests or both.

In other embodiments, the invention provides methods of modulating the colonization frequencies of endophytes that are native to the agricultural plant grown from the seed compared to a reference seed that is planted in an agricultural environment, comprising contacting the seed of the agricultural plant with a formulation comprising facultative fungal endophytes of at least one species, and wherein endophytes are present in the formulation in an amount effective to modulate the colonization frequencies of native endophytes and to provide a benefit to the seeds or the agricultural plants grown from the seeds. In certain aspects, the native endophytes are of genus *Alternaria*. In a further aspect, the facultative fungal endophytes are capable of producing substances that are beneficial to plants or detrimental to pests or both.

In another aspect, the invention provides methods for altering the systemic defensive pathway in a plant comprising contacting an agricultural seed of said plant with a formulation comprising a purified facultative fungal endophytes of at least one species, and wherein the endophyte is present in the synthetic combination in an amount effective to modulate the level of at least one phytohormone within an agricultural plant grown from the plant seed, and to provide a benefit to the seeds or the agricultural plants grown from the seeds. In a further aspect, the facultative fungal endophytes are capable of producing substances that are beneficial to plants or detrimental to pests or both.

In yet another aspect, the invention provides methods of producing a plant with a network of fungal endophytes that comprises endophytes of the genus *Alternaria*, comprising (a) contacting the seed of an agricultural plant with a formulation comprising facultative fungal endophytes of at least one non-*Alternaria* species, wherein endophytes are present in the formulation in an amount effective to provide a benefit to the seeds or the agricultural plants grown from the seeds, and wherein the plant grown from the seed comprises endophytes of the genus *Alternaria*. In a further aspect, the facultative fungal endophytes are capable of producing substances that are beneficial to plants or detrimental to pests or both.

Also provided herein are synthetic combinations of an agricultural plant seed and a composition comprising purified entomopathogenic fungal endophytes of at least one species, wherein the endophytes are capable of (1) colonizing the agricultural plant grown from the plant seed (2) and at least one of: reducing pest reproduction, killing pests, and deterring pests, from within the agricultural plant; wherein the endophytes are not of species *Beauveria bassiana*, and wherein the endophyte is present in the synthetic combination in an amount effective to provide a benefit other than enhanced resistance to biotic stress to the seeds or the agricultural plants derived from the seeds when the seeds or plants are grown in an agricultural setting.

In yet another aspect, the invention provides synthetic combinations of an agricultural plant seed and a composition comprising purified facultative fungal endophytes of at least one species, wherein the endophyte is present in the synthetic combination in an amount effective to modulate the level of at least one phytohormone within an agricultural plant grown from the plant seed, and to provide a benefit to the seeds or the agricultural plants grown from the seeds. In a further aspect, the facultative fungal endophytes are capable of producing substances that are beneficial to plants or detrimental to pests or both.

In another embodiment, the invention provides synthetic combinations of an agricultural plant seed and a composition comprising purified facultative fungal endophytes of at least one species, wherein the facultative fungal endophytes are present in the synthetic combination in an amount effective to modulate the colonization frequencies of endophytes that are native to the agricultural plant grown from the seed compared to a reference seed that is planted in an agricultural environment, and to provide a benefit to the seeds or the agricultural plants grown from the seeds. In a further aspect, the facultative fungal endophytes are capable of producing substances that are beneficial to plants or detrimental to pests or both. In certain aspects, the facultative fungal endophytes are present in the synthetic combination in an amount effective to modulate the colonization frequencies of endophytes of genus *Alternaria* that are native to the agricultural plant grown from the seed compared to a reference seed that is planted in an agricultural environment.

In a further aspect for certain of these methods and synthetic combinations, the composition comprising purified facultative fungal endophytes also comprises an agriculturally acceptable carrier.

In a further aspect for certain of these methods and synthetic combinations, the facultative fungal endophyte may be a filamentous fungal endophyte. In other embodiments, the facultative endophyte may be spore-forming. In yet other embodiments, the facultative fungal endophyte may be a septate fungal endophyte. In yet other embodiments, the facultative fungal endophyte may be a dark septate fungal endophyte. In some embodiments, the facultative endophyte may be an entomopathogen. In some embodiments, the facultative fungal endophyte may belong to the phylum Ascomycota or Basidiomycota. In a further aspect, the facultative fungal endophyte may belong to subphylum Pezizomycotina, Agaricomycotina, or Ustilaginomycotina. In yet another aspect, facultative fungal endophyte may belong to class Sordariomycetes, Dothideomycetes, Agaricomycetes, Ustilaginomycetes, Orbiliomycetes, or Eurotiomycetes. In yet another aspect, the facultative fungal endophyte may belong to order Hypocreales, Pleosporales, Capnodiales, Sordariales, Polyporales, Diaporthales, Ustilaginales, Xylariales, Orbiliales, Trichosphaeriales, or Eurotiales.

In a further aspect, the facultative fungal endophyte may be a species from Table 1, namely *Acremonium alternatum, Alternaria alternata, Alternaria brassicae, Alternaria compacta, Alternaria dianthi, Alternaria longipes, Alternaria mali, Alternaria sesami, Alternaria solani, Alternaria* sp., *Alternaria tenuissima, Ascomycota* sp., *Bipolaris spicifera, Cercospora canescens, Cercospora capsici, Cercospora kikuchii, Cercospora zinnia, Chaetomium globosum, Chaetomium piluliferum, Chaetomium* sp., *Cladosporium cladosporioides, Cladosporium* sp., *Cladosporium uredinicola, Cochliobolus* sp, *Phanerochaete crassa, Phoma americana, Phoma subherbarum, Phomopsis liquidambari, Phomopsis* sp., *Pleospora* sp., *Pleosporaceae* sp., *Polyporales* sp., *Preussia africana, Preussia* sp., *Pseudozyma* sp., *Pyrenophora teres, Colletotrichumcapsici, Coniolariella gamsii, Coniothyrium aleuritis, Coniothyrium* sp., *Corynespora cassiicola, Diaporthe* sp., *Diatrype* sp., *Drechslerella dactyloides, Embellisia indefessa, Epicoccum nigrum, Epicoccum* sp., *Exserohilum rostratum, Fusarium chlamydosporum, Fusarium* sp., *Gibellulopsis nigrescens, Gnomoniopsis* sp., *Lewia infectoria, Mycosphaerella coffeicola, Mycosphaerellaceae* sp., *Nigrospora oryzae, Nigrospora* sp., *Nigrospora sphaerica, Paecilomyces* sp., *Penicillium citrinum, Retroconis* sp., *Rhizopycnis* sp., *Schizothecium inaequale, Stagonospora* sp., *Stemphylium lancipes, Thielavia hyrcaniae, Thielavia* sp., *Ulocladium chartarum, Verticillium* sp., *Beauveria bassiana, Aspergillus parasiticus, Lecanicillium lecanii*, and *Paecilomyces lilacinus*.

In a further aspect, the facultative fungal endophyte comprises a nucleic acid that is at least 97% identical, for example, at least 98% identical, at least 99% identical, at least 99.5% identical, or 100% identical to the nucleic acids provided in any of SEQ ID NO:7 through SEQ ID NO:77, for example those listed in Example 16.

In another aspect for certain of these methods is an additional step of packaging the contacted seeds in a container may be included. In certain aspects, the packaging material may be selected from a bag, box, bin, envelope, carton, or container, and may comprise a dessicant.

In a further aspect for certain of these methods and synthetic combinations, the benefit to the treated seed or plant grown from the treated seed is measured at the level of the population, as compared to a reference population of plants. In certain aspects, the facultative fungal endophyte may be providing a benefit to a crop comprising a plurality of agricultural plants produced from the seeds treated with the endophyte. In certain aspects, the present invention discloses a substantially uniform population of plants produced by growing the population of seeds described above. In one embodiment, at least 75%, at least 80%, at least 90%, at least 95% or more of the plants comprise in one or more tissues an effective amount of the endophyte or endophytes. In another embodiment, at least 10%, 20%, 30%, 40%, 50%, 60%, 70%, 75%, at least 80%, at least 90%, at least 95% or more of the plants comprise a microbe population that is substantially similar.

In a further aspect for certain of these methods and synthetic combinations, the plant is grown in an agricultural setting or environment, including a greenhouse. In one embodiment, the agricultural setting or environment comprises at least 100 plants. In another embodiment, the population occupies at least about 100 square feet of space, wherein at least about 10%, 20%, 30%, 40%, 50%, 60%, 70%, 80%, 90% or more than 90% of the population comprises an effective amount of the microbe. In another embodiment, the population occupies at least about 100 square feet of space, wherein at least about 10%, 20%, 30%, 40%, 50%, 60%, 70%, 80%, 90% or more than 90% of the population comprises the microbe in reproductive tissue. In still another embodiment, the population occupies at least about 100 square feet of space, wherein at least about 10%, 20%, 30%, 40%, 50%, 60%, 70%, 80%, 90% or more than 90% of the population comprises at least 10 CFUs, 100 CFUs, 1,000 CFUs, 10,000 CFUs or more of the facultative fungal endophyte of the invention. In yet another embodiment, the population occupies at least about 100 square feet of space, wherein at least about 10%, 20%, 30%, 40%, 50%, 60%, 70%, 80%, 90% or more than 90% of the population comprises the facultative fungal endophyte of the invention.

In one embodiment, at least 10%, at least 20%, at least 30%, at least 40%, at least 50%, at least 60%, at least 70%, at least 75%, at least 80%, at least 90%, at least 95% or more of the seeds in the population, contains a viable endophyte or endophytes disposed on the surface of the seeds. In a particular embodiment, at least 10%, at least 20%, at least 30%, at least 40%, at least 50%, at least 60%, at least 70%, at least 75%, at least 80%, at least 90%, at least 95% or more of the seeds in the population contains at least 10 CFU, for example, at least 30 CFU, at least 100 CFU, at least 300 CFU, at least 1,000 CFU, at least 3,000 CFU, at least 10,000 CFU or more, of the endophyte or endophytes coated onto the surface of the seed.

In a further aspect for certain of these methods and synthetic combinations, the endophytes that are native to the agricultural plant and whose colonization frequencies or ratios are altered may belong to phylum Ascomycota or Basidiomycota. In yet another aspect, the endophytes that are native to the agricultural plant may be of class Leotiomycetes, Dothideomycetes, Eurotiomycetes, Saccharomycetes, Sordariomycetes, Agaricomycetes, Microbotryomycetes, Tremellomycetes. In yet another aspect, the native endophytes may belong to order Capnodiales, Pleosporales, Chaetothyriales, Eurotiales, Saccharomycetales, Diaporthales, Hypocreales, Ophiostomatales, Sordariales, Trichosphaeriales, Xylariales, Cantharellales, Corticiales, Polyporales, Russulales, Sporidioboiales, or Tremellales. In a further aspect, the native endophytes may belong to genus Davidiellaceae, Mycosphaerellaceae, Pleosporaceae, Didymellaceae, Sporormiaceae, Chaetothyriaceae, Trichocomaceae, Saecharomycetaceae, Gnomoniaceae, Cordycipitaceae, Nectriaceae, Hypocreaceae, Plectosphaerellaceae, Ophiostomataceae, Chaetomiaceae, Lasiosphaeriaceae, Trichosphaeriaceae, Ceratobasidiaceae, Corticiaceae, Coriolaceae, Peniophoraceae, Sporidiobolaceae, or Tremellaceae. In a further aspect, the endophytes that are native to the agricultural plant may be a species from Table 2, namely *Cladosporium* sp., *Cladosporium cladosporioides*, *Davidiella* sp., *Cercospora* sp., *Cercospora beticola*, *Alternaria* sp., *Alternaria alternata*, *Alternaria citri*, *Alternaria tenuissima*, *Cochliobolus* sp., *Curvularia* sp., *Exserohilum* sp., *Lewia* sp., *Lewia infectoria*, *Pyrenophora* sp., *Pyrenophora triticirepentis*, *Pleospora* sp., *Phoma americana*, *Preussia africana*, *Penicillium* sp., *Thermomyces* sp., *Therinomyces lanuginosus*, *Candida* sp., *Candida quercitrusa*, *Candida tropicalis*, *Cyberlindnera* sp., *Cyberlindnera jadinii*, *Kluyveromyces* sp., *Kluyveromyces marxianus*, *Gnomoniopsis* sp., *Beauveria bassiana*, *Cordyceps* sp., *Cordyceps bassiana*, *Fusarium* sp., *Gibellulopsis nigrescens*, *Hypocrea* sp., *Hypocrea lixii*, *Hypocrea vixens*, *Trichoderma* sp., *Trichoderma tomentosum*, *Verticillium* sp., *Ophiostoma* sp., *Ophiostoma dendifundum*, *Chaetomium* sp., *Chaetomium globosum*, *Thielavia hyrcaniae*, *Taifanglania* sp., *Taifanglania inflata*, *Schizathecium inaequale*, *Nigrospora* sp., *Rhizoctonia* sp., *Phanerochaete* sp, *Trametes* sp., *Trametes hirsuta*, *Trametes villosa*, *Rhodotorula* sp., *Rhodotorula mucilaginosa*, *Cryptococcus* sp, *Cryptococcus skinneri*, or *Tremella* sp.

In a further aspect for certain of these methods and synthetic combinations, the benefit provided by the facultative fungal endophyte to the agricultural plant is an improved agronomic property selected from the group consisting of increased biomass, increased tillering, increased root mass, increased flowering, increased yield, increased water use efficiency, reduction of yield loss, altered plant height, decreased time to emergence, increased seedling height, increased root length, increased chlorophyll levels, retention of developing flowers, retention of developing fruits, altered phytohormone levels, and enhanced resistance to environmental stress relative to a reference plant. In some aspects, the benefit provided is the alteration of levels of at least two phytohormones. In some aspects, the environmental stress is selected from the group consisting of drought stress, cold stress, heat stress, nutrient deficiency, salt toxicity, aluminum toxicity, grazing by herbivores, insect infestation, nematode infection, and fungal infection, bacterial infection and viral infection. In some aspects, the benefit to agricultural plants derived from the seed is increased yield in a population of said plants by about 5%, 10%, 15%, 20%, 30%, 40%, or 45% relative to a reference population of plants. In other aspects, the benefit to agricultural plants derived from the seed is a reduction of yield loss in a population of said plants by more than 40%, 30%, 20%, 10%, 5%, or 1% relative to a reference population of plants. In some aspects, treatment of seeds with facultative fungal endophytes may decrease thrip damage, decrease fleahopper damage, increase canopy temperature, increase drought tolerance, increase above ground biomass, and increase below ground biomass in the plants grown from the treated seeds.

In a further aspect for certain of these methods and synthetic combinations, the facultative fungal endophyte is present in the synthetic combination in an amount effective to obtain at least 50% colonization of the leaves, stems or roots of an agricultural plant grown from the seed.

In a further aspect for certain of these methods and synthetic combinations, the facultative fungal endophytes are capable of producing substances that are detrimental to pests. In certain aspects, the pest may be a nematode and/or an insect, for example, a root knot nematode, a aphid, a *lygus* bug, a stink bug, or combinations thereof.

In a further aspect for certain of these methods and synthetic combinations, the synthetic combination may comprise at least 1, 2, 3, 4, 5, 6, 7, 8, 9, 10, 11, 12, 13, 14, 15, 16, 17, 18, 19, or 20 facultative fungal endophytes. In one aspect, the invention provides a synthetic combination of a cotton plant or seed and a fungal endophyte comprising at least 1, 2, 3, 4, 5, 6, 7, 8, 9, 10, 11, 12, 13, 14, 15, 16, 17, 18, 19, or 20 endophytes selected from those in Table 1, wherein the cotton or seed is a host of the endophyte.

In another aspect, a seed coating is provided comprising a fungal endophyte comprising at least 1, 2, 3, 4, 5, 6, 7, 8, 9, 10, 11, 12, 13, 14, 15, 16, 17, 18, 19, or 20 endophytes from Table 1; and at least one sticker, wherein the fungal endophyte is in contact with the sticker. In certain aspects, the sticker may comprise, for example, alginic acid, carrageenan, dextrin, dextran, pelgel, polyethelene glycol, polyvinyl pyrrolidone, methyl cellulose, polyvinyl alcohol, gelatin, or combinations thereof. In certain aspects, the sticker may have a weight ratio between fungal endophyte and sticker of 1:1-10, 1:10-50, 1:50-100, 1:100-500, 1:500-1000, or 1:1000-5000. The seed coating may be a solid or fluid. In certain aspects, the seed coating is a powder. In certain aspects, the fungal endophyte may comprise fungal spores. In various aspects, the seed coating may comprise about 1, 2, 5, 10, 50, $10^2$, $10^3$, $10^4$, $10^5$, $10^6$, $10^7$, $10^8$, or $10^9$ or more colony forming units per gram or spores per gram.

In certain embodiments, compositions for foliar or soil application may comprise a fungal endophyte comprising at least 1, 2, 3, 4, 5, 6, 7, 8, 9, 10, 11, 12, 13, 14, 15, 16, 17, 18, 19, or 20 endophytes from Table 1, and at least one carrier, surfactant or diluent. In certain aspects, the compositions may comprise may comprise about 1, 2, 5, 10, 50, $10^2$, $10^3$, $10^4$, $10^5$, $10^6$, $10^7$, $10^8$, or $10^9$ or more colony forming units per gram or spores per gram. In various aspects, the composition may comprise water, a detergent, Triton X, insecticides, fungicides, or combinations thereof, for example. In further embodiments, seed compositions comprise a plant seed and the above-described seed coating. In certain aspects, the plant seed comprises a cotton seed, a seed of an agronomically elite plant, a dicot plant seed, and/or a monocot plant seed. In certain aspects, the seed composition may be resistant to a pest comprising an insect and/or a nematode.

In yet another aspect, the invention provides methods for preventing pest infestation or increasing yield, which may comprise treating a plant, plant seed, or the rhizosphere of said plant or seed with the endophyte containing compositions described herein. In certain aspects, the method may also comprise identifying a plant or seed as in need of endophyte treatment. The pest may comprise, for example, a nematode and/or insect. In certain aspects, the pest may comprise a root knot nematode, a aphid, a *lygus* bug, a stink bug, or combinations thereof.

In still yet another aspect, methods for preventing pest infestation are provided comprising obtaining a seed described herein and planting the seed. The method may further comprise identifying a need of preventing pest infestation. In certain aspects, the pest may comprise a nematode and/or a insect; and/or the pest may comprise a root knot nematode, a aphid, a *lygus* bug, a stink bug, or combinations thereof.

In a further embodiment, a method for treating a pest infestation comprises identifying a plant suspected of being infected with a pest, applying an above-described composition to the plant, whereby an endophyte-treated plant is generated. In certain aspects, the pest may comprise a nematode and/or an insect; and/or the pest may comprise a root knot nematode, a aphid, a *lygus* bug, a stink bug, or combinations thereof.

In still yet another aspect, a method of manufacturing pest-resistant seeds is provided comprising providing a fungal endophyte composition comprising at least 1, 2, 3, 4, 5, 6, 7, 8, 9, 10, 11, 12, 13, 14, 15, 16, 17, 18, 19, or 20 endophytes from Table 1, providing seeds; and combining the seeds with the endophyte composition, whereby pest-resistant seeds are generated. In certain aspects, the method increases the percentage of colonization with the endophyte of the plant developing from the seed.

In still yet another aspect, methods of increasing a yield of a crop or a reduction of loss are disclosed comprising providing a fungal endophyte composition comprising at least 1, 2, 3, 4, 5, 6, 7, 8, 9, 10, 11, 12, 13, 14, 15, 16, 17, 18, 19, or 20 endophytes from Table 1; and applying the endophyte composition to a seed, plant or part thereof, whereby the yield of the crop increases. In certain aspects, the crop may be cotton, and the increase of yield may be at least about 2%, 3% 5%, 15%, 20%, or 25% relative to a crop to which no endophyte composition has been applied. In certain aspects, the increase of yield is about 2%-5%, 3%-5%, 5%-10%, 10%-15%, or greater than about 20%, 30%, or more relative to a crop to which no endophyte composition has been applied. In certain aspects, the crop is cotton and the increase of yield comprises reduced boll damage. In certain aspects, the reduction of loss comprises reduction of loss due to insect infestation or drought, and the loss is less than 50%, 40%, 30%, 20%, 10%, 5%, or 5% relative to a crop to which no endophyte composition has been applied.

Also described herein are commodity plant products comprising a plant or part of a plant (including a seed) and further comprising the facultative fungal endophyte described above that is present in a detectable level, for example, as detected by the presence of its nucleic acid by PCR. In another aspect, disclosed is a method of producing a commodity plant product, comprising obtaining a plant or plant tissue from the synthetic combination described above, and producing the commodity plant product therefrom. The commodity plant product can be produced from the seed, or the plant (or a part of the plant) grown from the seed. The commodity plant product can also be produced from the progeny of such plant or plant part. The commodity plant product can be is selected from the group consisting of grain, flour, starch, seed oil, syrup, meal, flour, oil, film, packaging, nutraceutical product, an animal feed, a fish fodder, a cereal product, a processed human-food product, a sugar or an alcohol and protein.

Figure 3:
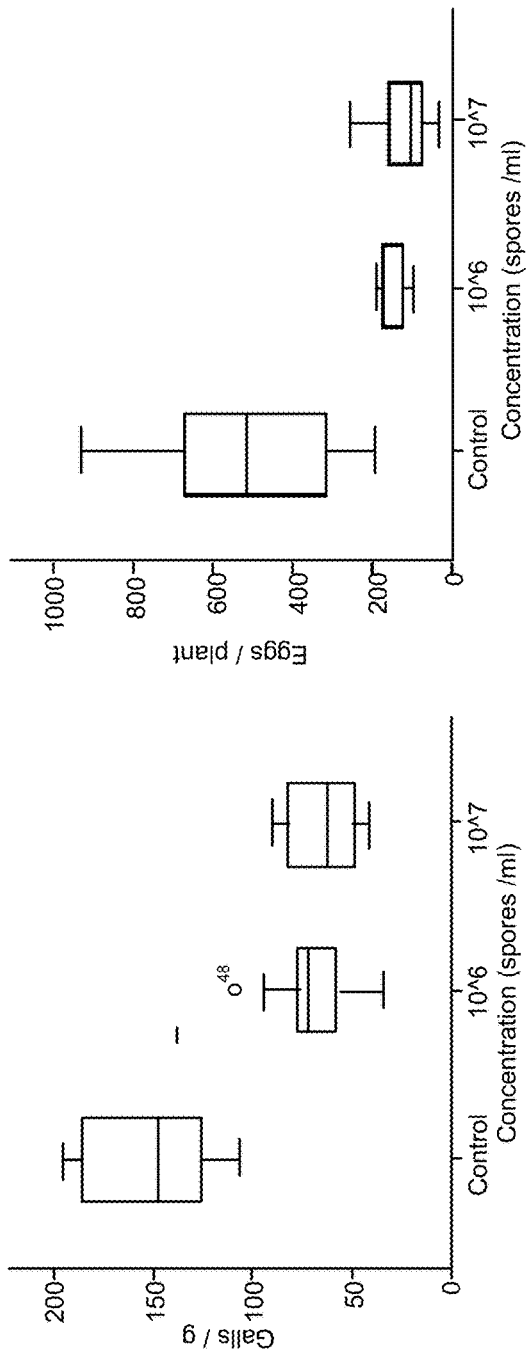

FIG. 3: Endophytic *Chaetomium globosum* negatively affects root-knot nematode reproduction. Negative effects of endophytic *Chaetomium globosum* on root-knot nematode gall formation and egg production following cotton seed soaking treatments in solutions of 0 (untreated controls), $10^6$ and $10^8$ spores/ml. Seedlings were inoculated with 1000 nematode eggs and grown in the greenhouse. Egg production by hatching nematodes that successfully infected the seedlings was quantified 60 days later.

Figure 4A:
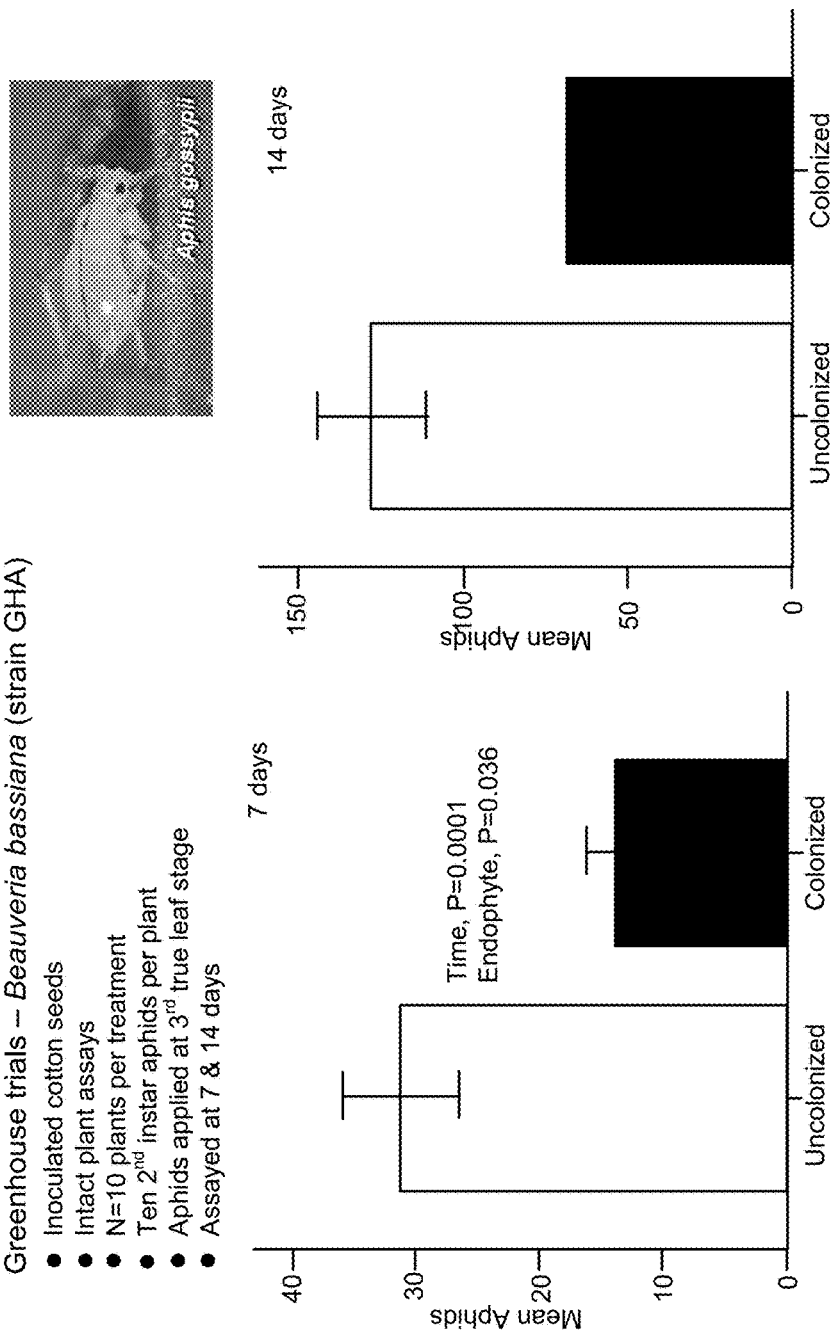
Figure 4B:
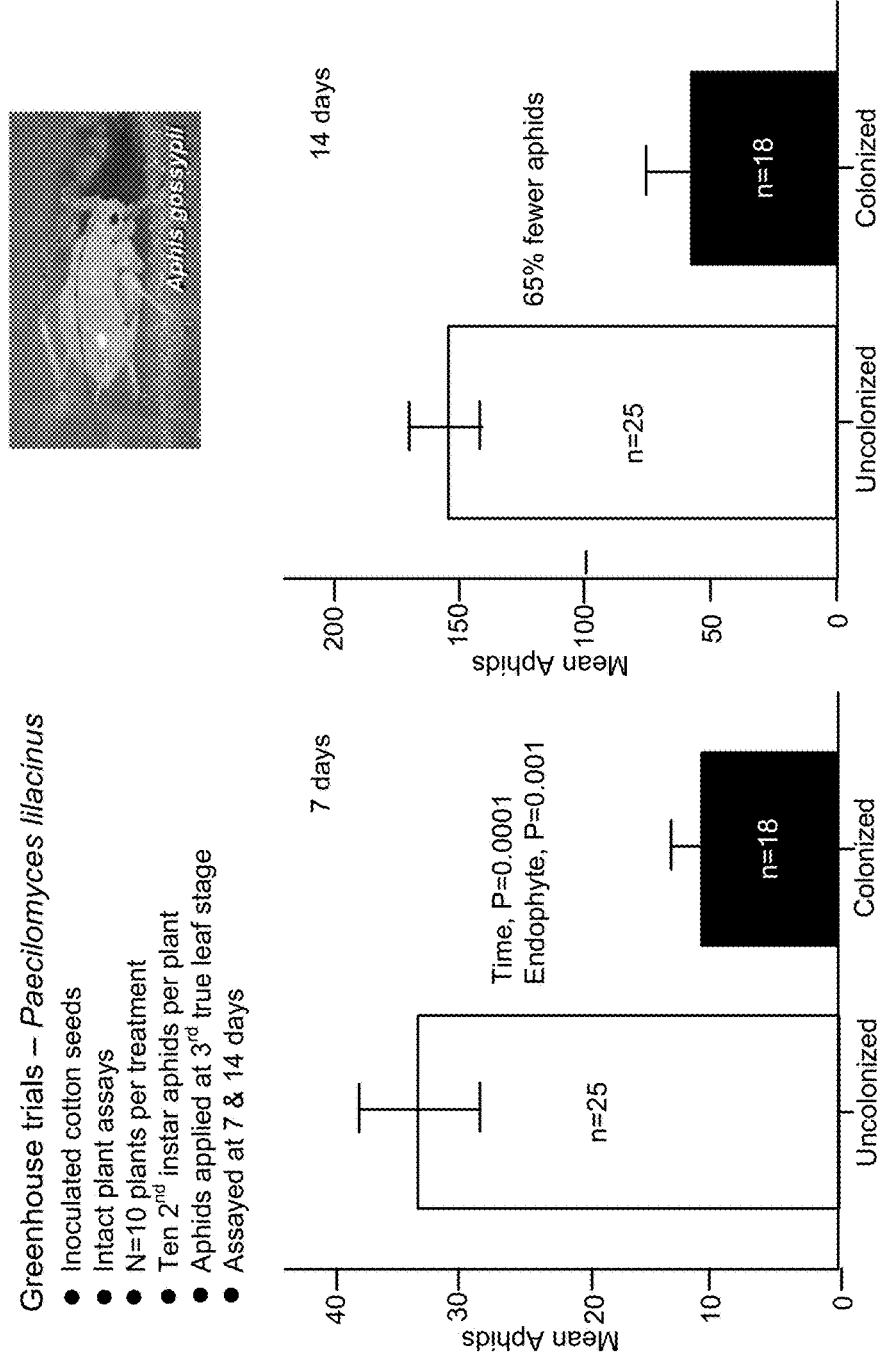

FIG. 4A and FIG. 4B: The effect of endophytic fungi on cotton aphids (*Aphis gossypii*) reproduction. FIG. 4A demonstrates that the presence of *Beauveria bassiana* in cotton negatively affects the reproduction of cotton aphids. FIG. 4B demonstrates that the presence of *Paecilomyces lilacinus* in cotton negatively affects the reproduction of cotton aphids.

Figure 5:
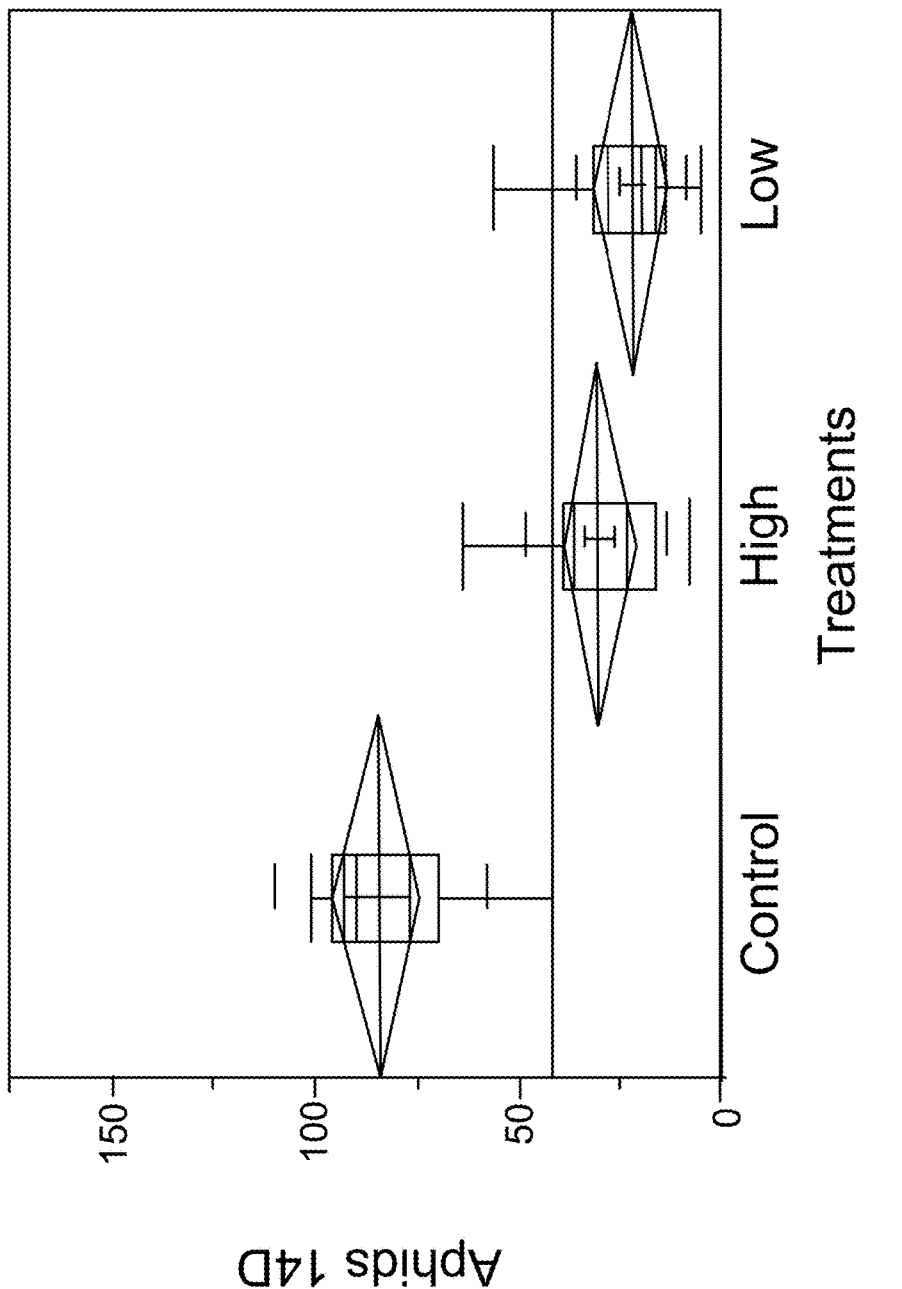

FIG. 5: Effects of *Chaetomium globosum* on cotton aphids. Endophytic *Chaetomium globosum* in cotton negatively affects cotton aphid population growth rates as evidenced by reduced reproduction after 14 days on endophyte-colonized versus control plants. Cotton plants were grown from seeds treated by soaking in spore solutions of 0 (control), $10^6$ (low) and 108 (high) spores/ml.

Figure 6A:
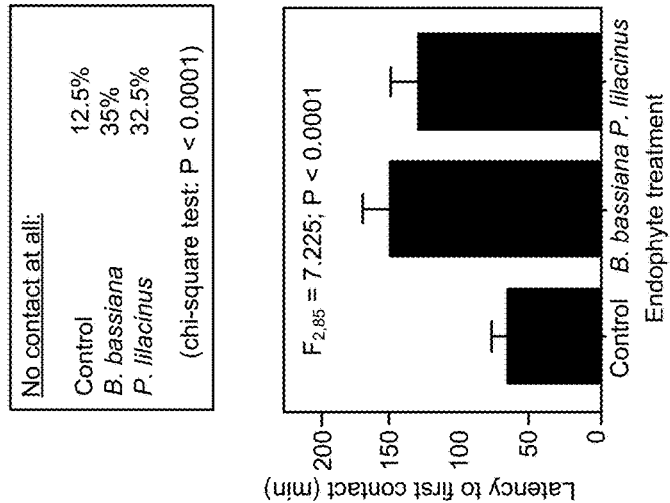
Figure 6A:
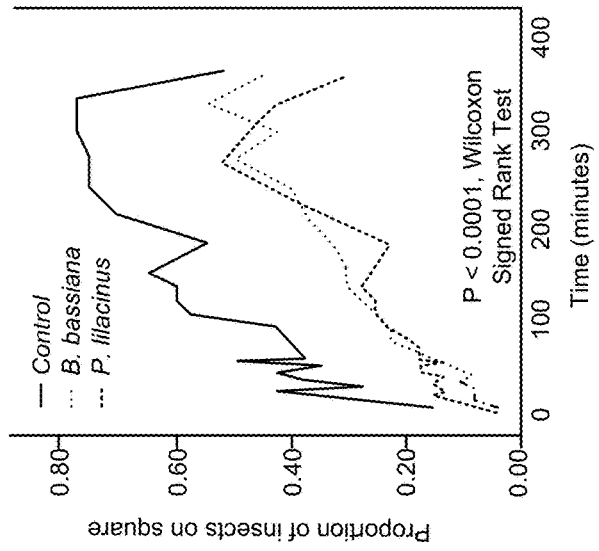
Figure 6B:
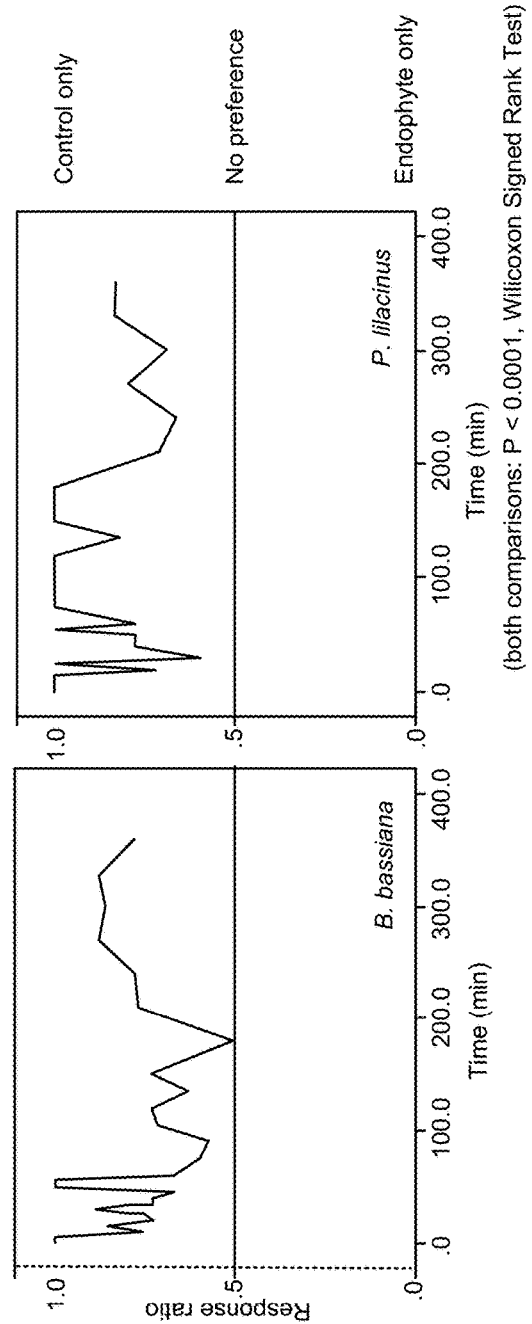

FIG. 6A and FIG. 6B: The effect of the endophytic fungi *Beauveria bassiana* and *Paecilomyces lilacinus* on western tarnished plant bugs *Lygus hesperus* (Miridae). FIG. 6A demonstrates that *Beauveria bassiana* and *Paecilomyces lilacinus* negatively affect host plant selection of western tarnished plant bugs when present as an endophyte in cotton. FIG. 6B demonstrates that *Beauveria bassiana* and *Paecilomyces lilacinus* negatively affect host plant selection behavior of western tarnished plant bugs when present as an endophyte in cotton.

Figure 7A:
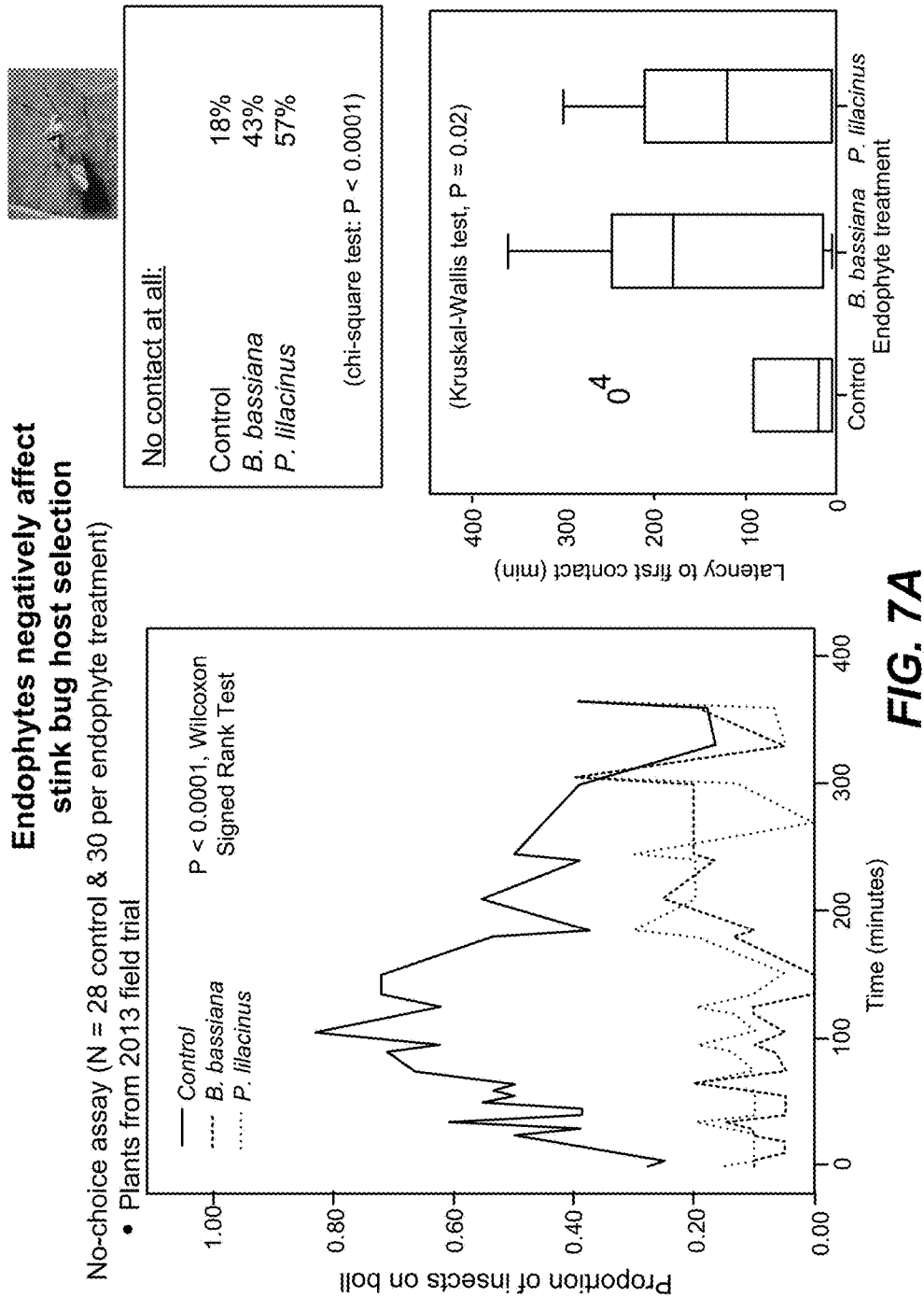
Figure 7B:
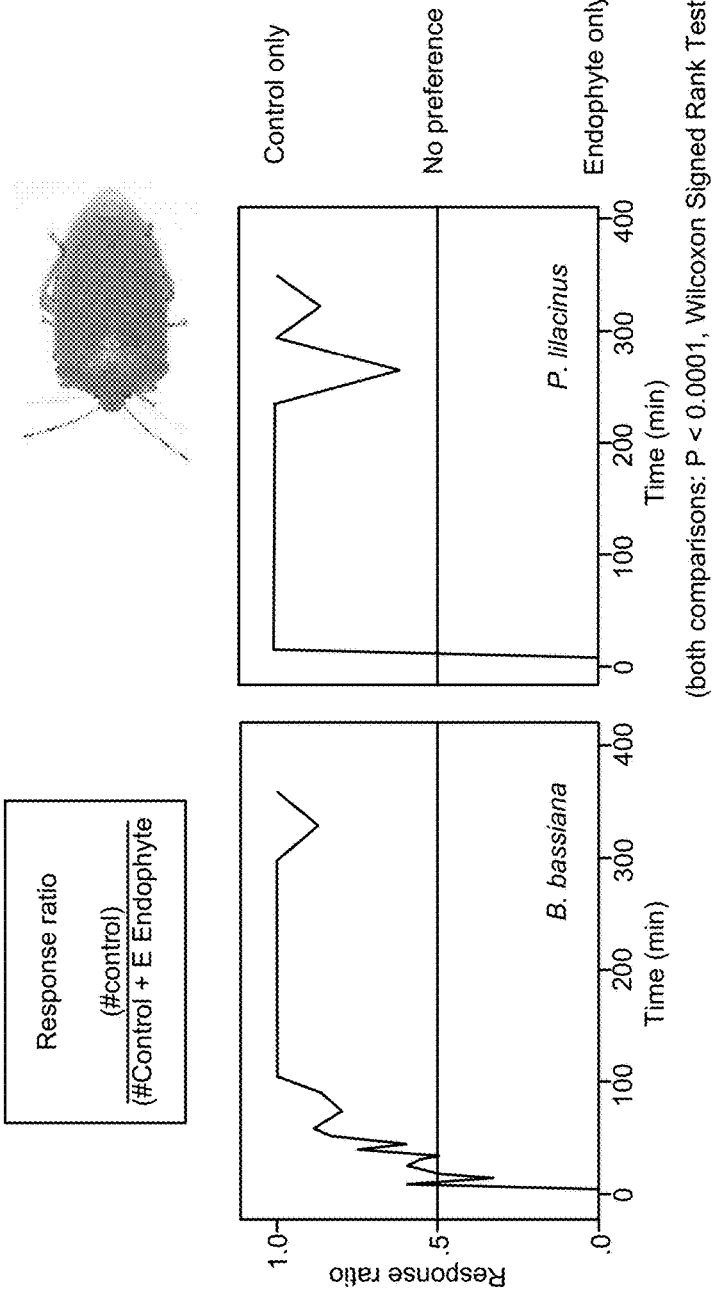

FIG. 7A and FIG. 7B: The effect of the endophytic fungi *Beauveria bassiana* and *Paecilomyces lilacinus* on southern green stink bugs (*Nezara viridula* (Pentatomidae). FIG. 7A demonstrates that *Beauveria bassiana* and *Paecilomyces lilacinus* negatively affect host plant selection of southern green stink bugs when present as an endophyte in cotton. FIG. 7B demonstrates that *Beauveria bassiana* and *Paecilomyces lilacinus* negatively affect host plant selection behavior of southern green stink bugs when present as an endophyte in cotton.

Figure 8:
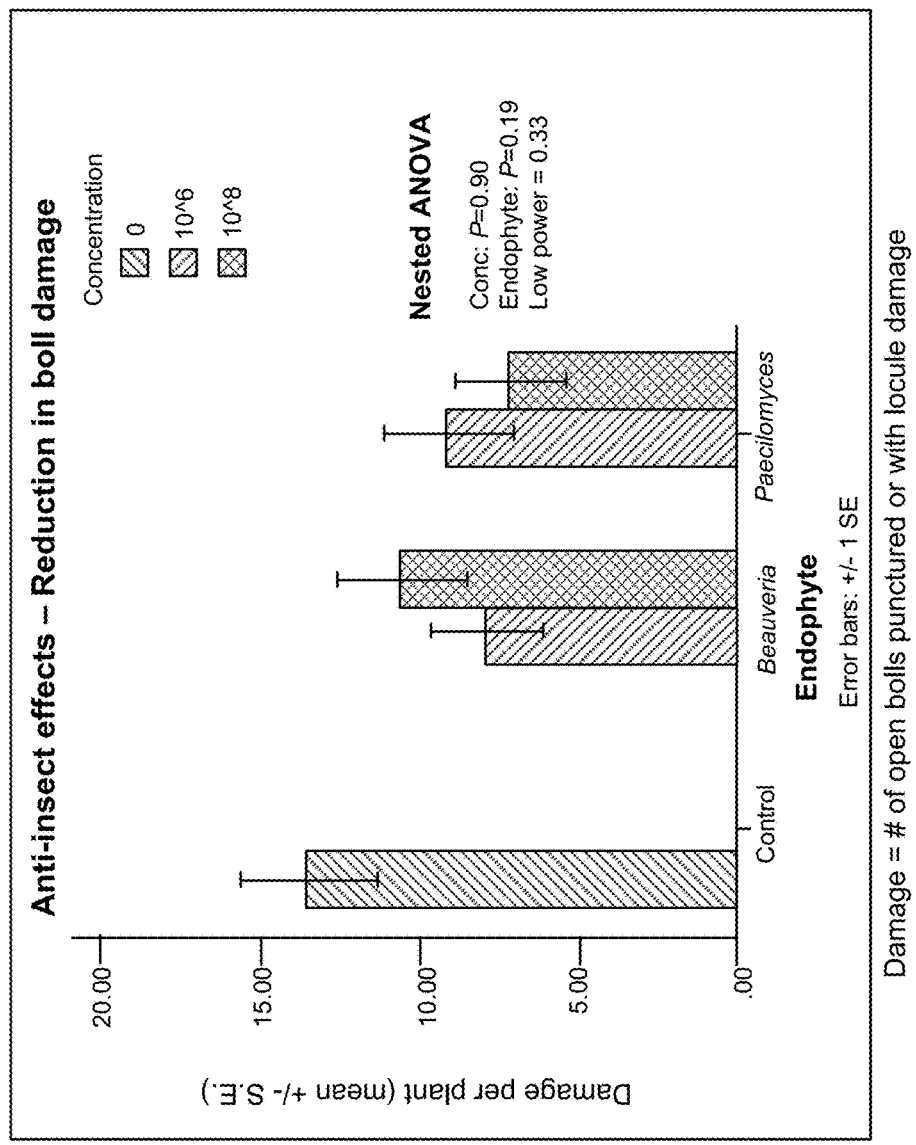

FIG. 8: A reduction in cotton boll damage was observed during field trials. Relative to control plants, levels of insect-related boll damage were lower among plants that were treated by soaking seeds in spore solutions of *Beauveria bassiana* and *Paecilomyces lilacinus* at concentrations of $10^6$ and $10^8$ spore/ml.

Figure 9:
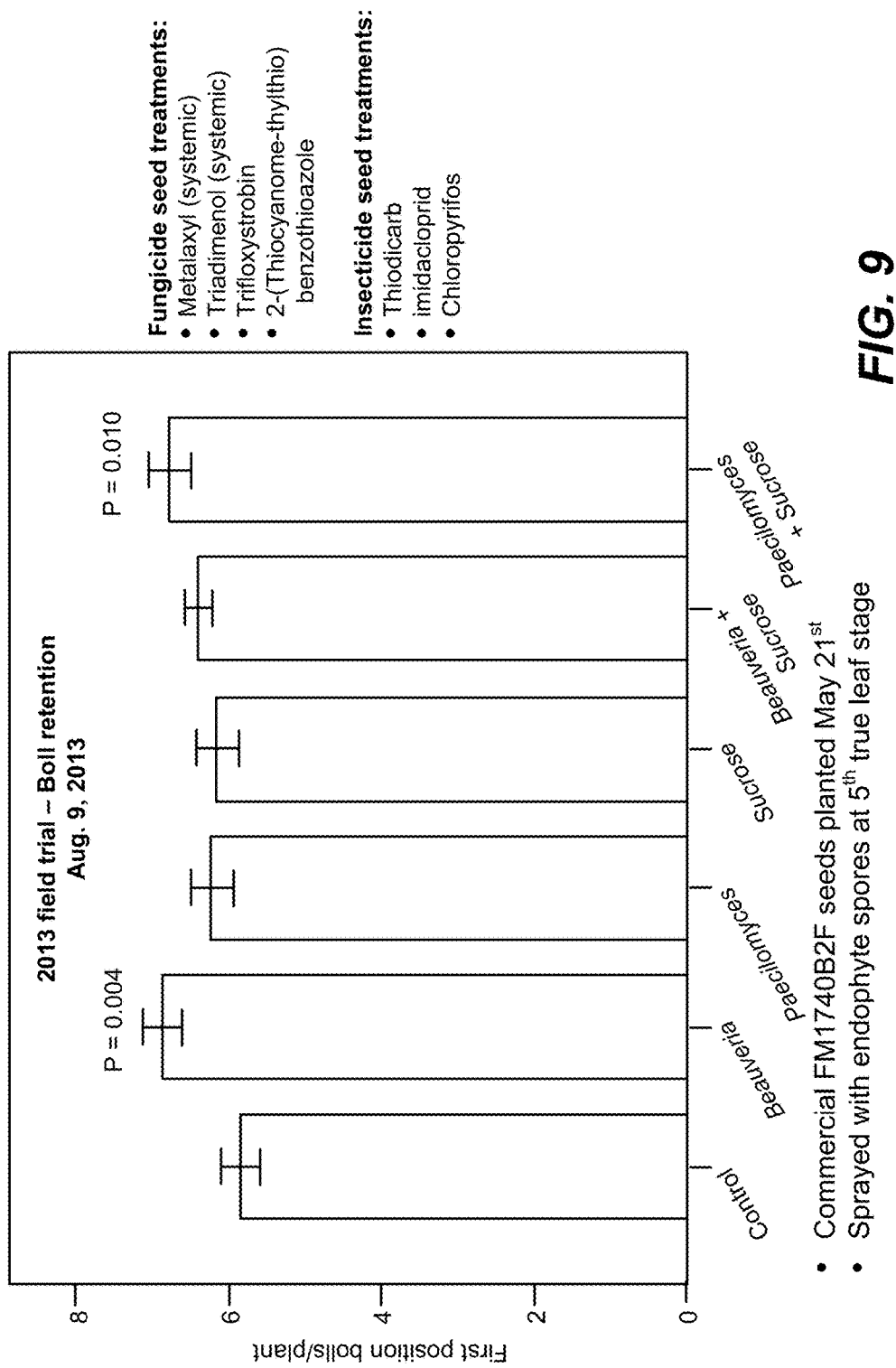

FIG. 9: Foliar application of cotton in the field with spores of endophytic entomopathogenic fungi improves plant performance. Cotton (variety FM1740B2F) seeds treated with a variety of typical fungicide (Metalaxyl, Triadimenol, Trifloxystrobin, 2-(Thiocyanome-thylthio) benzothioazole) and insecticide (Thiodicarb, Imidacloprid, Chloropyrifos) seed treatments were planted and grown under field conditions. The plants were sprayed at the 5th true leaf stage with aqueous solutions of *Beauveria bassiana* and *Paecilomyces fumosoroseus*. Sucrose was included (1% wt/vol) as an additional nutritional resource for the fungi. Significantly higher first position boll (developing fruit) retention was observed in plants sprayed with *Beauveria bassiana* without sucrose and *Paecilomyces fumosoroseus* plus sucrose.

FIG. 10A and FIG. 10B: Positive effects of fungal endophytes on cotton plant performance under field conditions. FIG. 10A demonstrates an early season trend for higher square retention in the treated versus untreated plants. FIG. 10B demonstrates that significantly more bolls were retained in the endophyte treatment groups later in the season, relative to control. This is demonstrated with both endophyte species used and with both seed treatment concentration employed (Repeated measures ANOVA: Time, $P<0.001$; Time*Endophyte, $P=0.045$, Endophyte, $P=0.003$).

Figure 11:
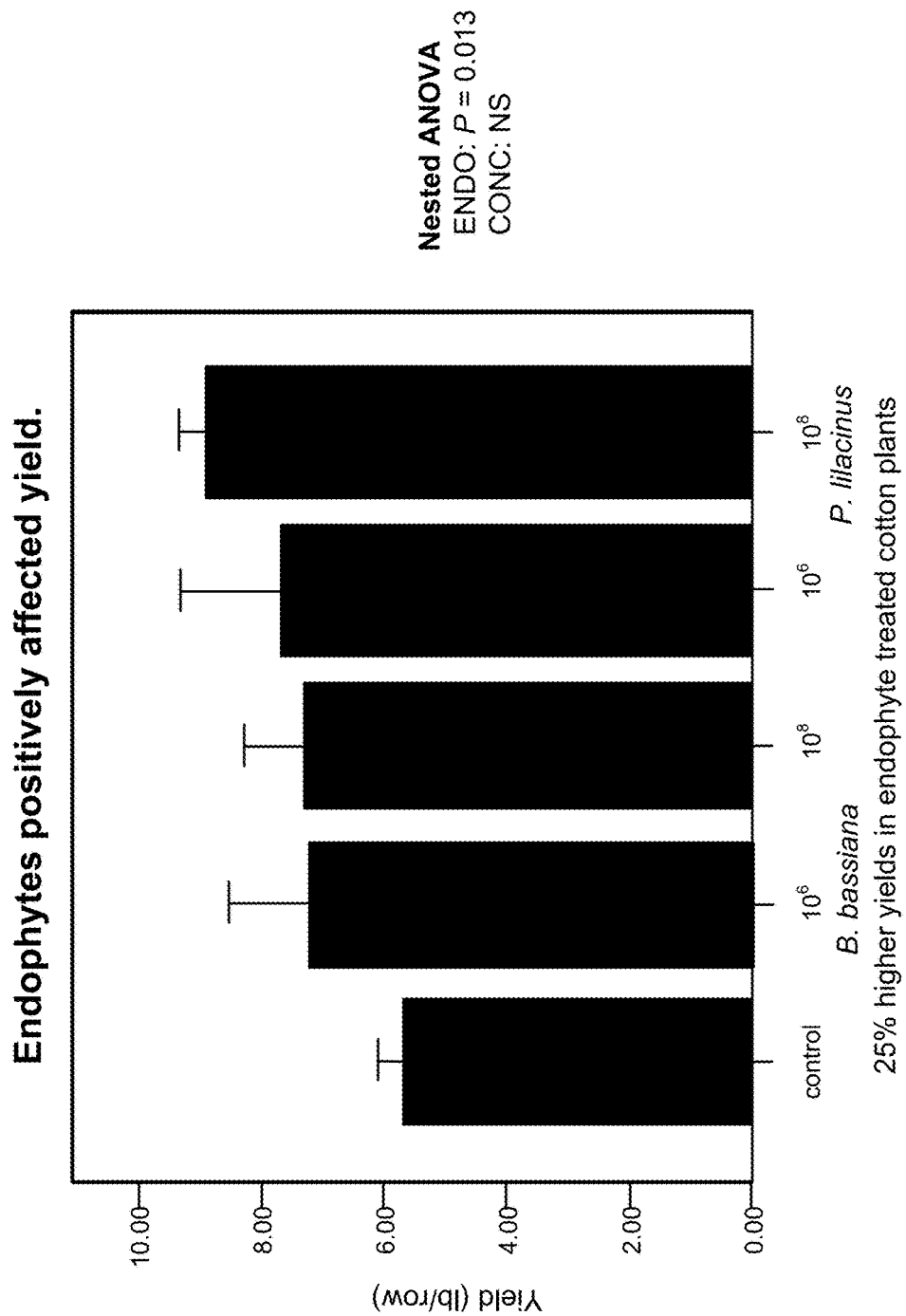

FIG. 11: Positive effects of fungal endophytes on cotton yields under field conditions. The data demonstrate that endophyte treatments achieved 25% higher yields in treated cotton plants.

Figure 12A:
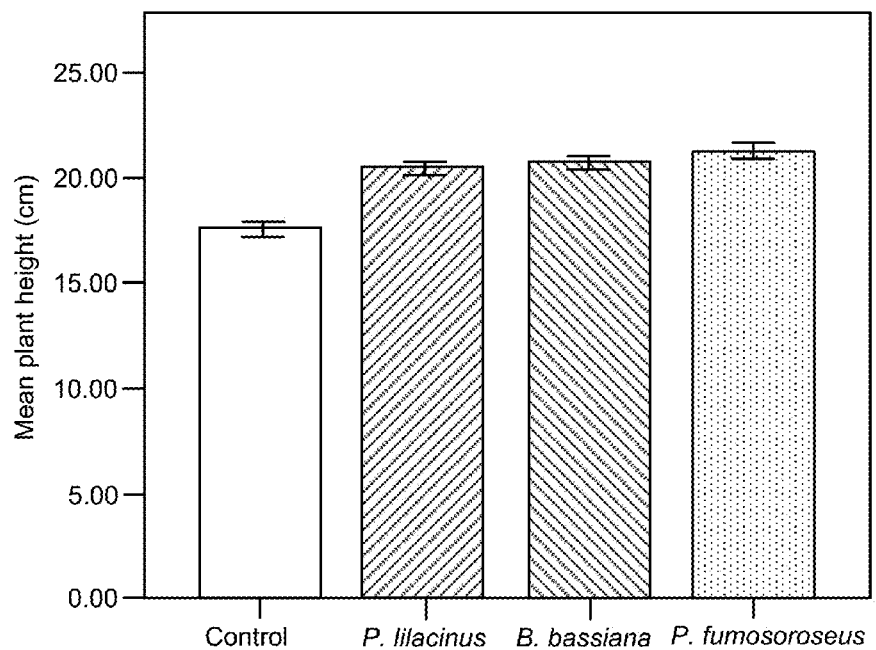
Figure 12B:
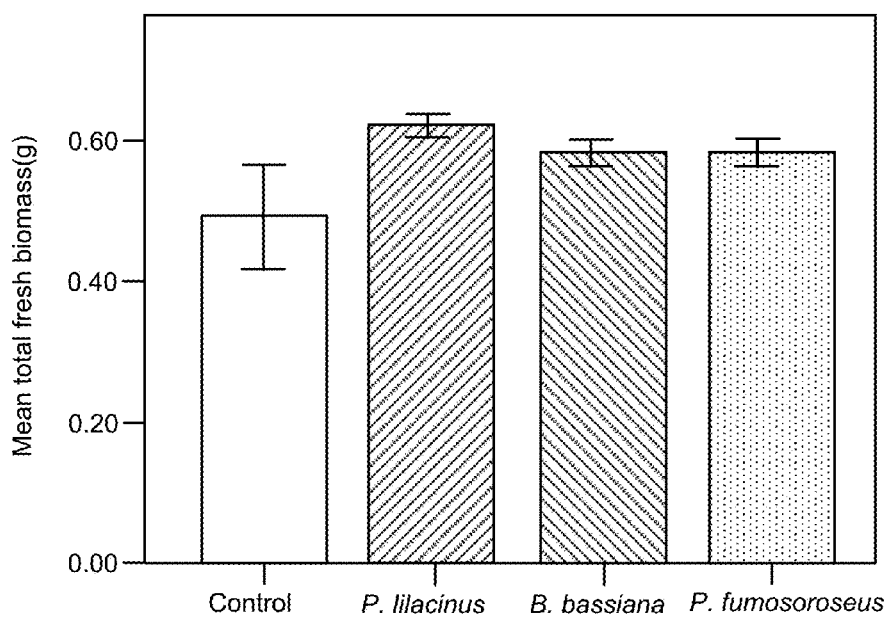

FIG. 12A and FIG. 12B: Positive effects of fungal endophytes on sorghum (FIG. 12A) plant height and (FIG. 12B) total fresh biomass under growth chamber seedling assays. Data shown is average plant height (cm) and total fresh biomass (g) of n=10 independent replicates. Error bars represent ±1 standard error. All three fungal endophytes improve both traits relative to the untreated control.

Figure 13:
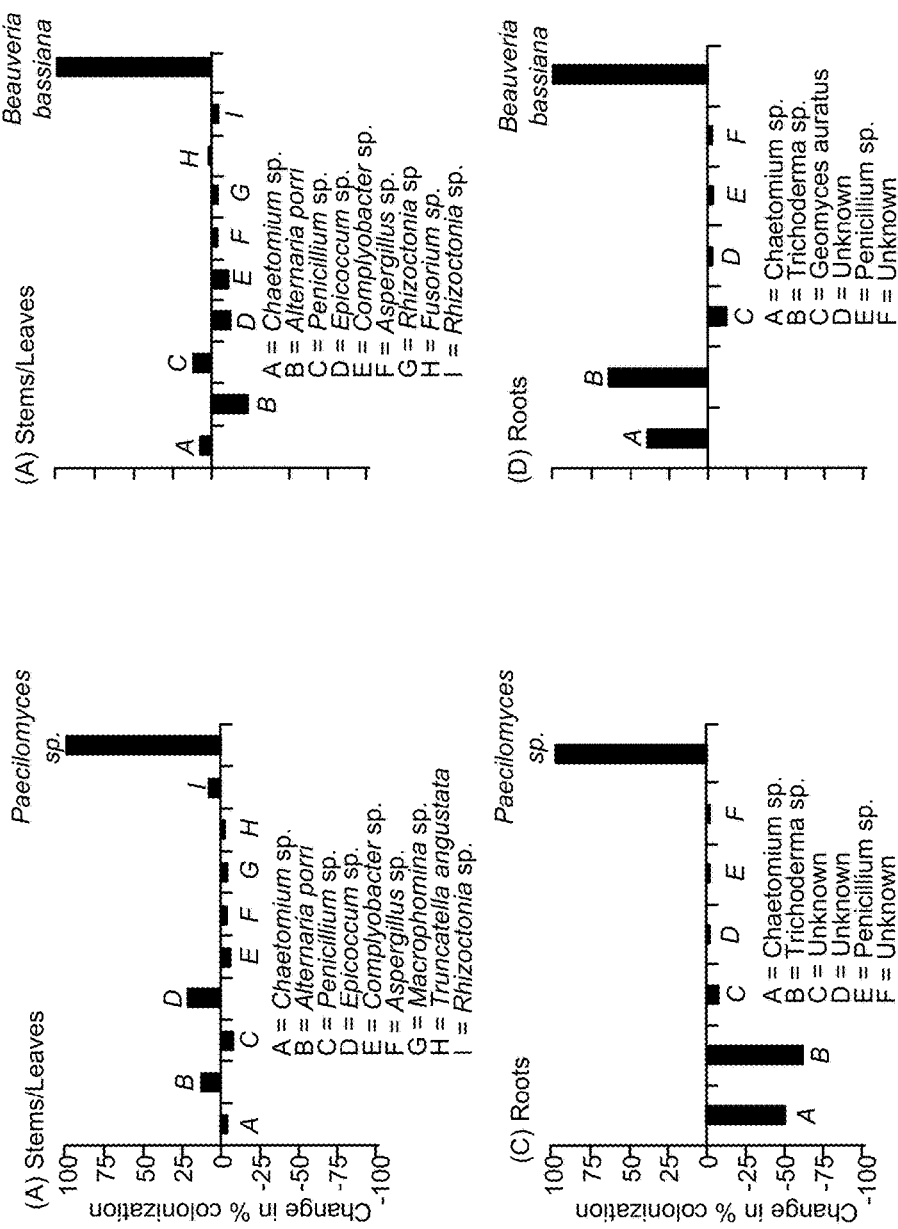

FIG. 13: The in-field modulation of the colonization of endogenous cotton endophytes in (panels A, B) stems and (panels C, D) roots when treated with fungal endophytes *Paecilomyces lilacinus* (panels A, C) and *Beauveria bassiana* (panels B, D). Data shown is a percentage change in colonization relative to the corresponding untreated control and plant tissue.

Figure 14:
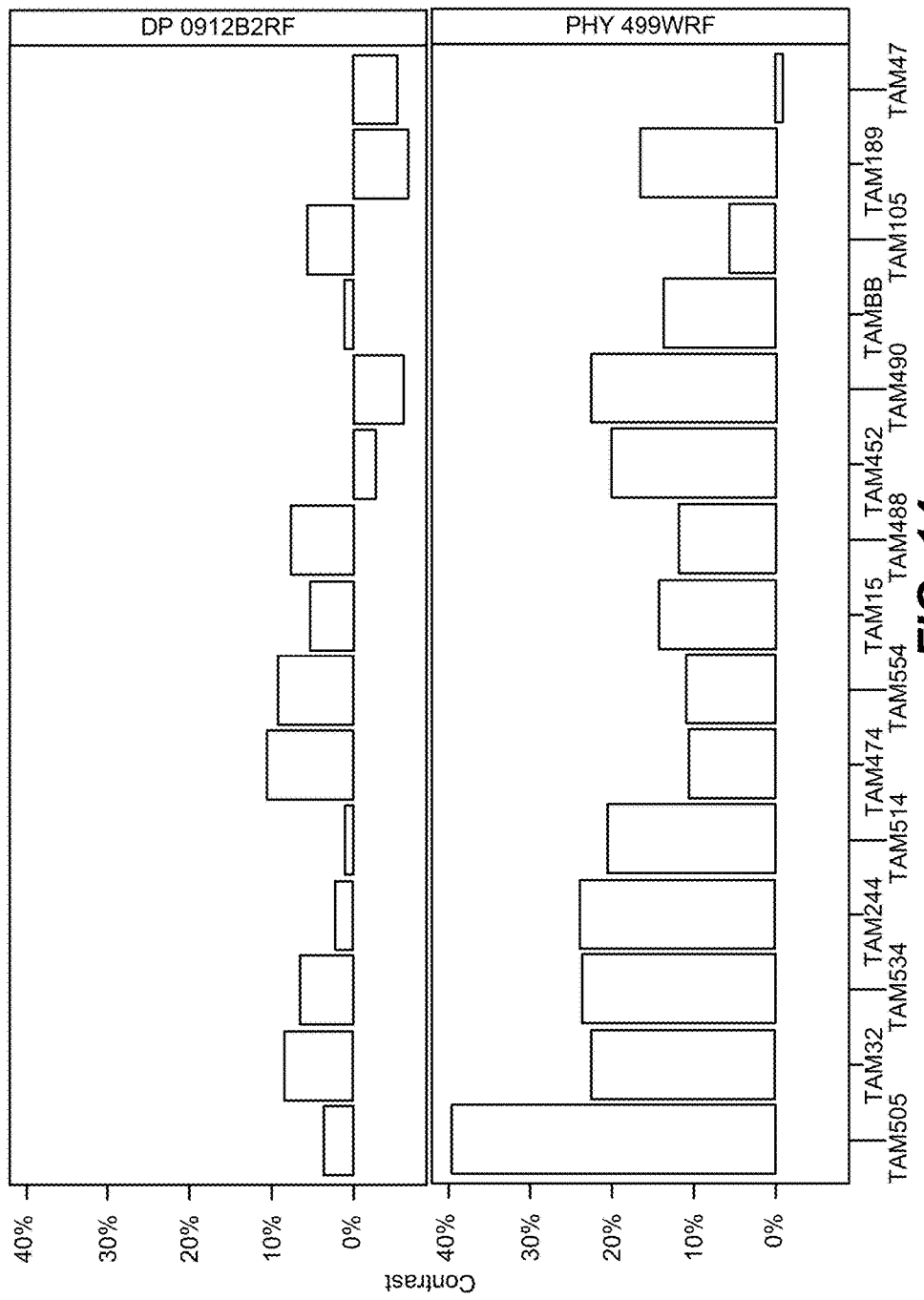

FIG. 14: Average percent difference in yield between endophyte treated and control cotton plants (n=6 replicate plots in a dryland field, College Station, Tex.) for 15 facultative fungal endophytes in the Phytogen (PHY 499WRF) cultivar.

Figure 15:
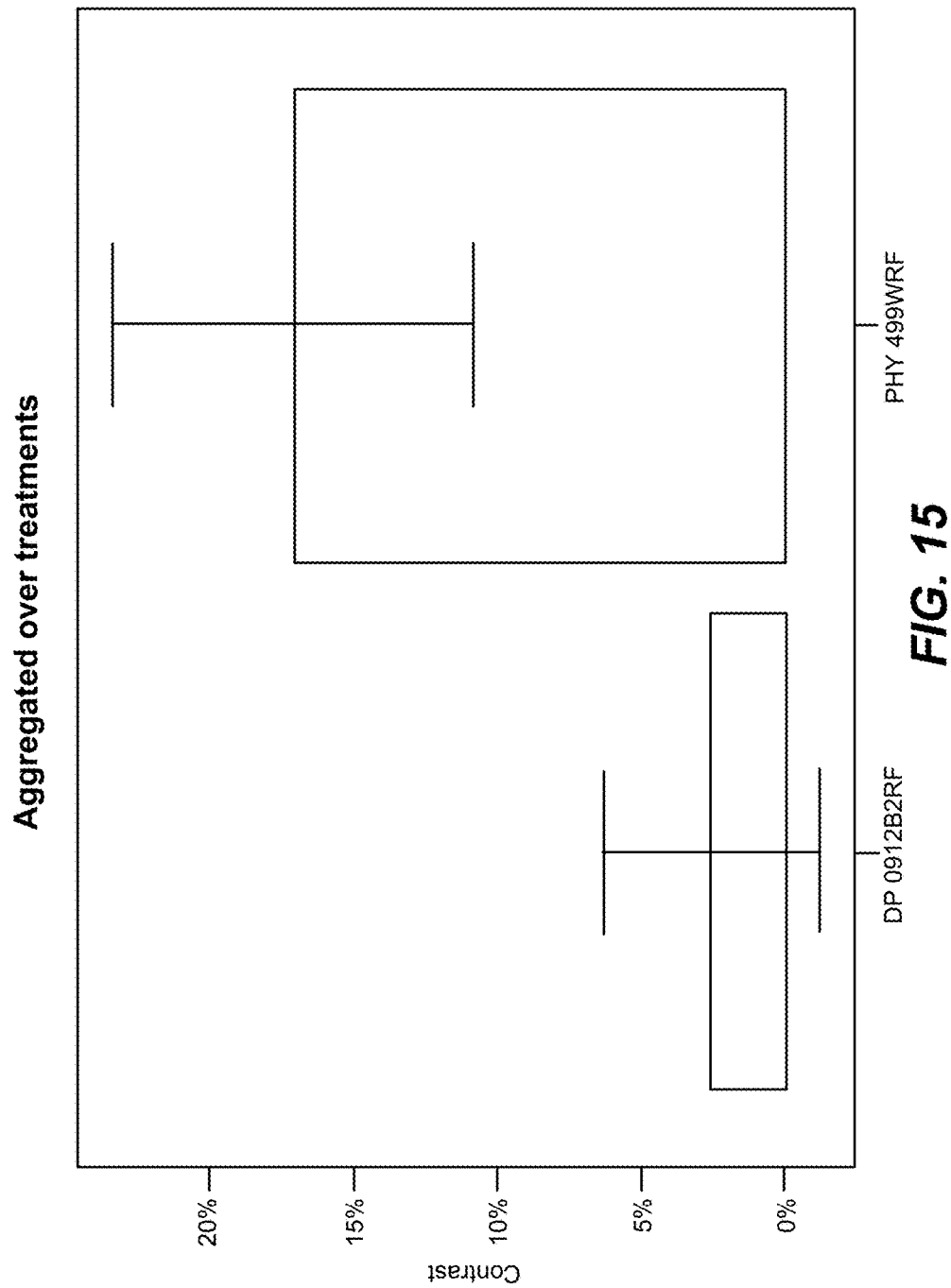

FIG. 15: Aggregated average percent difference in yield between endophyte treated and control cotton plants (n=6 replicate plots in a dryland field, College Station, Tex.) for 15 facultative fungal endophytes and two cotton cultivars; Delta Pine (DP 0912B2RF) and Phytogen (PHY 499WRF). Bars represent a 95% confidence interval around the mean.

FIG. 16A and FIG. 16B: Average percent difference in thrip damage (FIG. 16A) and fleahopper damage (FIG. 16B) between endophyte treated and control cotton plants. The thrip damage was assessed in the Delta Pine (DP 0912B2RF) cultivar (n=6 replicate plots in a dryland field, College Station, Tex.) for 15 facultative fungal endophytes. 12 out of the 15 facultative fungal endophytes tested showed a decrease in thrip damage relative to the untreated cotton plants. The fleahopper damage was assessed in cotton plants of the Phytogen (PHY 499WRF) cultivar (n=6 replicate plots in a dryland field, College Station, Tex.) for 15 facultative fungal endophytes. 6 out of the 15 facultative fungal endophytes tested showed an average decrease in fleahopper damage as compared to untreated cotton plants.

Figure 17B:
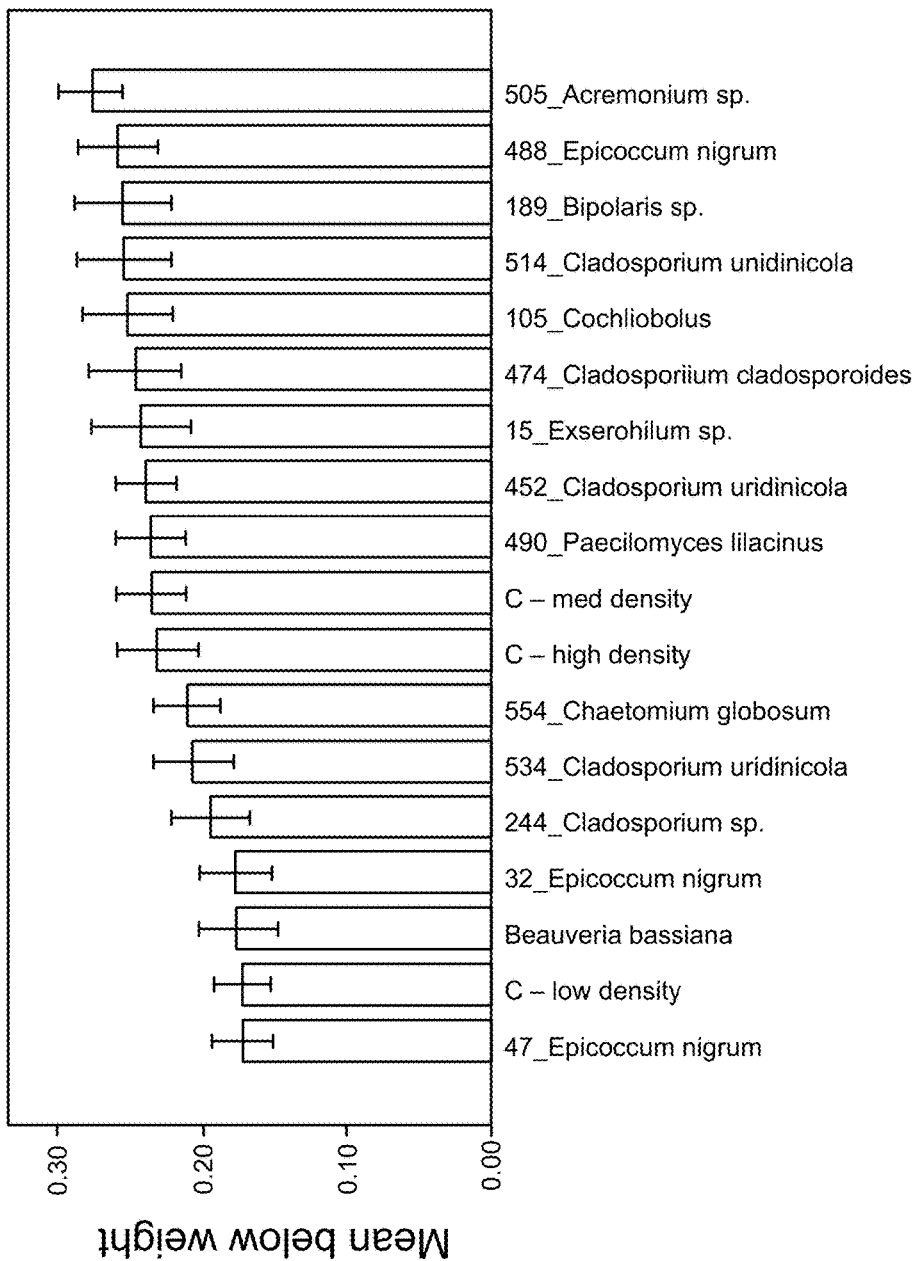

FIG. 17A and FIG. 17B: Mid-season field-trait measured in June at the dryland trial of (FIG. 17A) root length and (FIG. 17B) below ground weight. Data presented is the average of n=10 independent replicates and error bars represent ±one standard error.

Figure 18:
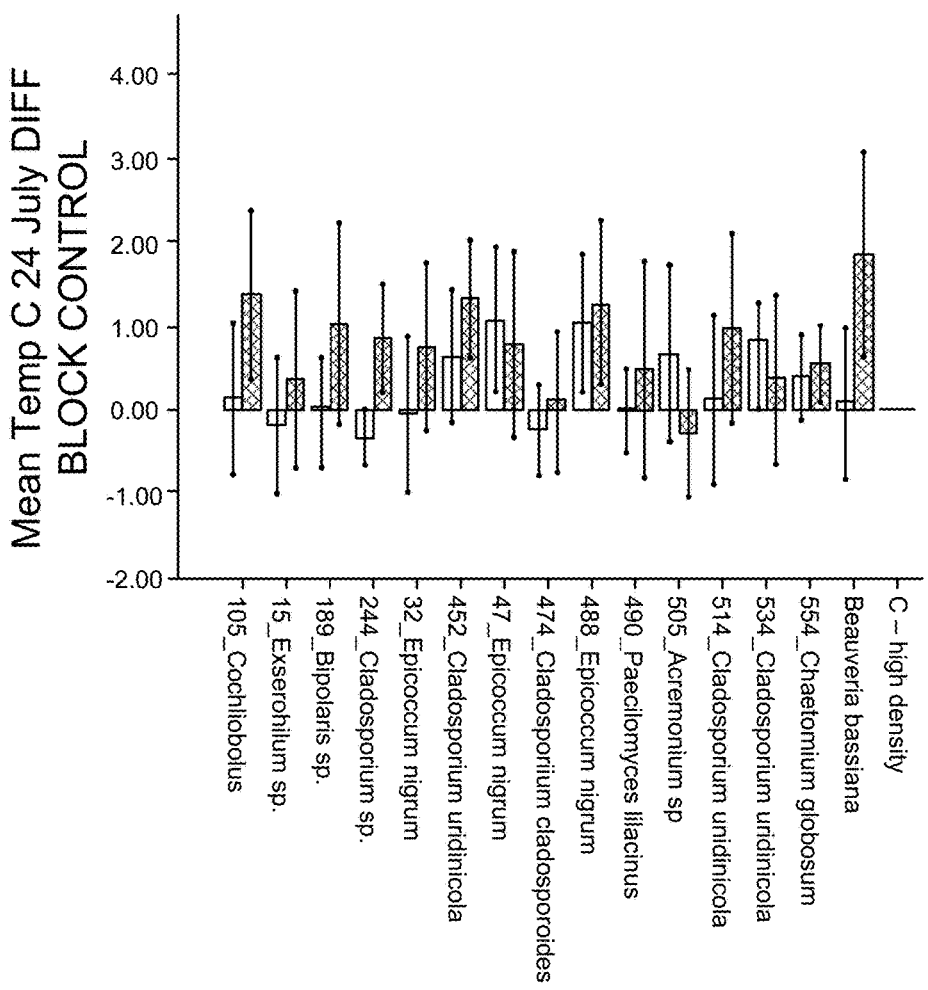

FIG. 18: Mid-season field-trait measured in July at the dryland trial of canopy temperature (Celsius) for the (open bars) Delta Pine and (hatched bars) Phyton cultivars. Data presented is the block-controlled average of n=10 independent replicates, relative to the control plot and error bars represent ±one standard error.

Figure 19:
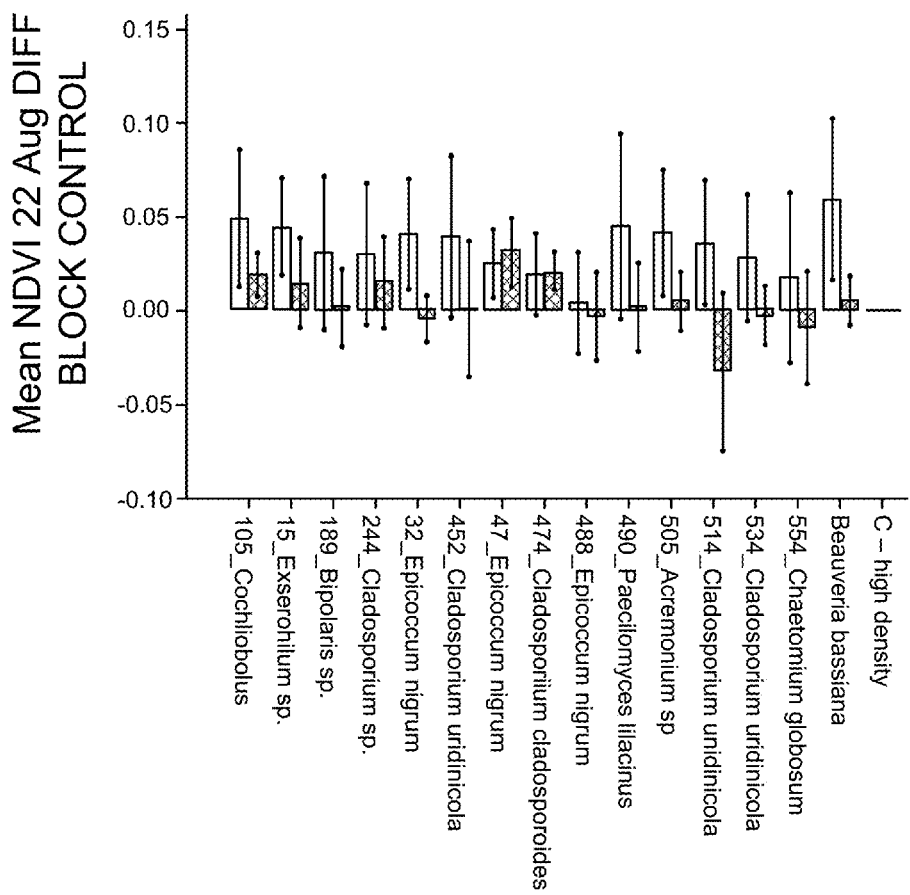

FIG. 19: Mid-season field-trait measured in August at the dryland trial of NDVI for the (open bars) Delta Pine and (hatched bars) Phyton cultivars. Data presented is the block-controlled average of n=10 independent replicates, relative to the control plot and error bars represent ±one standard error.

Figure 20:
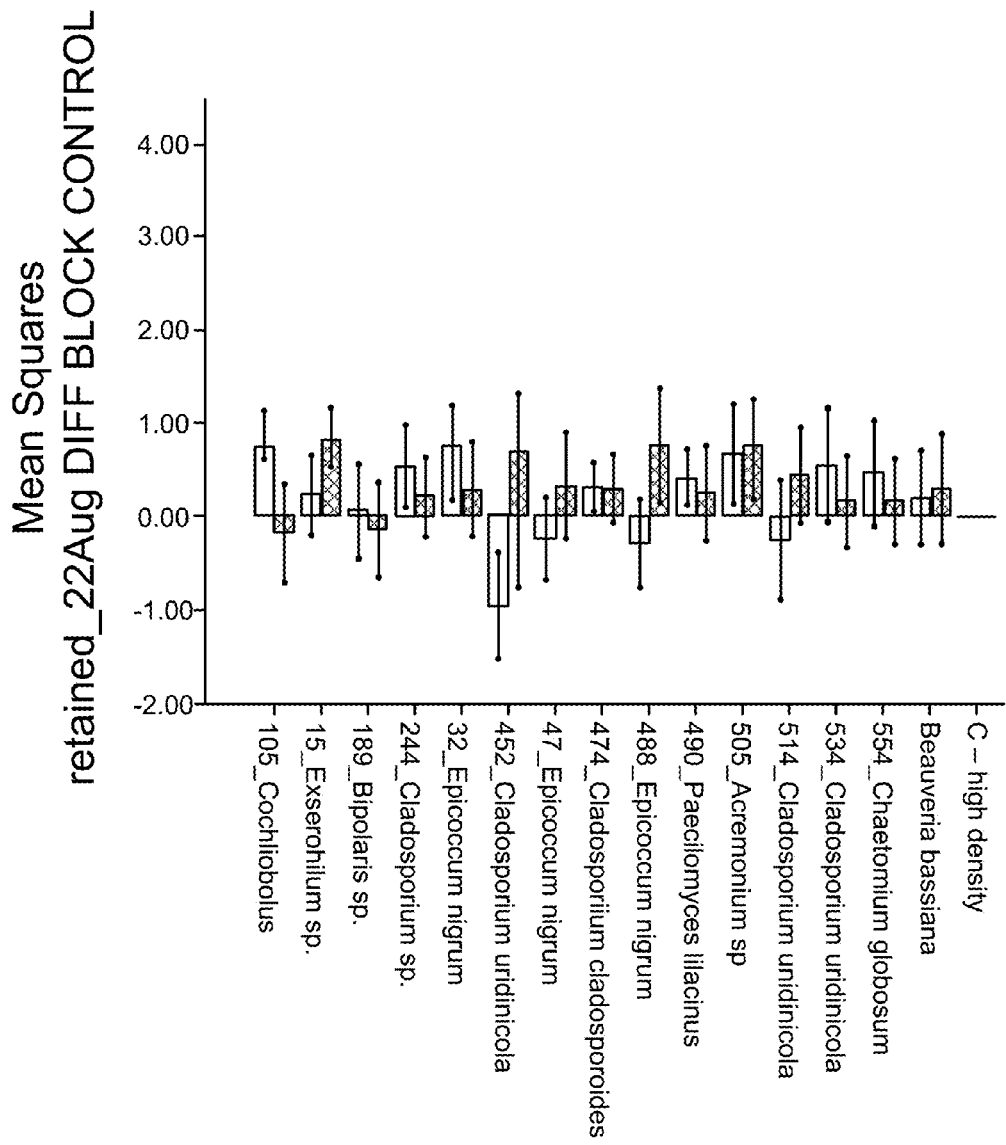

FIG. 20: Mid-season field-trait measured in August at the dryland trial of first position square retention for the (open bars) Delta Pine and (hatched bars) Phyton cultivars. Data presented is the block-controlled average of n=10 independent replicates, relative to the control plot and error bars represent ±one standard error.

Figure 21:
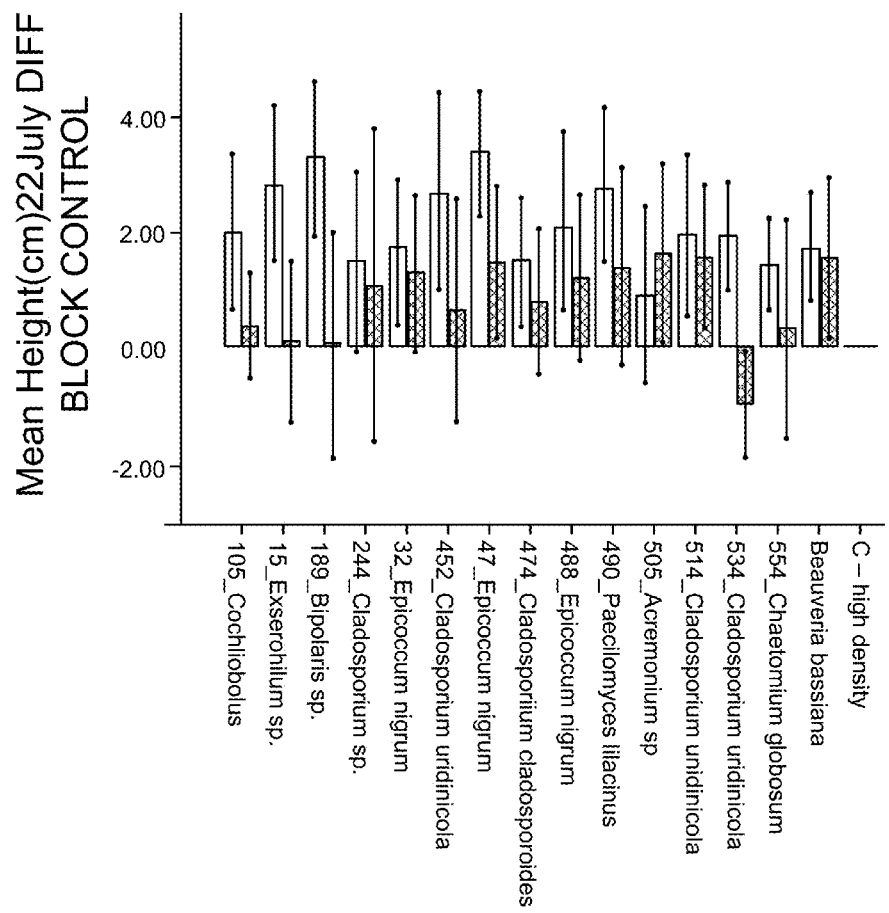

FIG. 21: Mid-season field-trait measured in August at the dryland trial of plant height (cm) for the (open bars) Delta Pine and (hatched bars) Phyton cultivars. Data presented is the block-controlled average of n=10 independent replicates, relative to the control plot and error bars represent ±one standard error.

Figure 22:
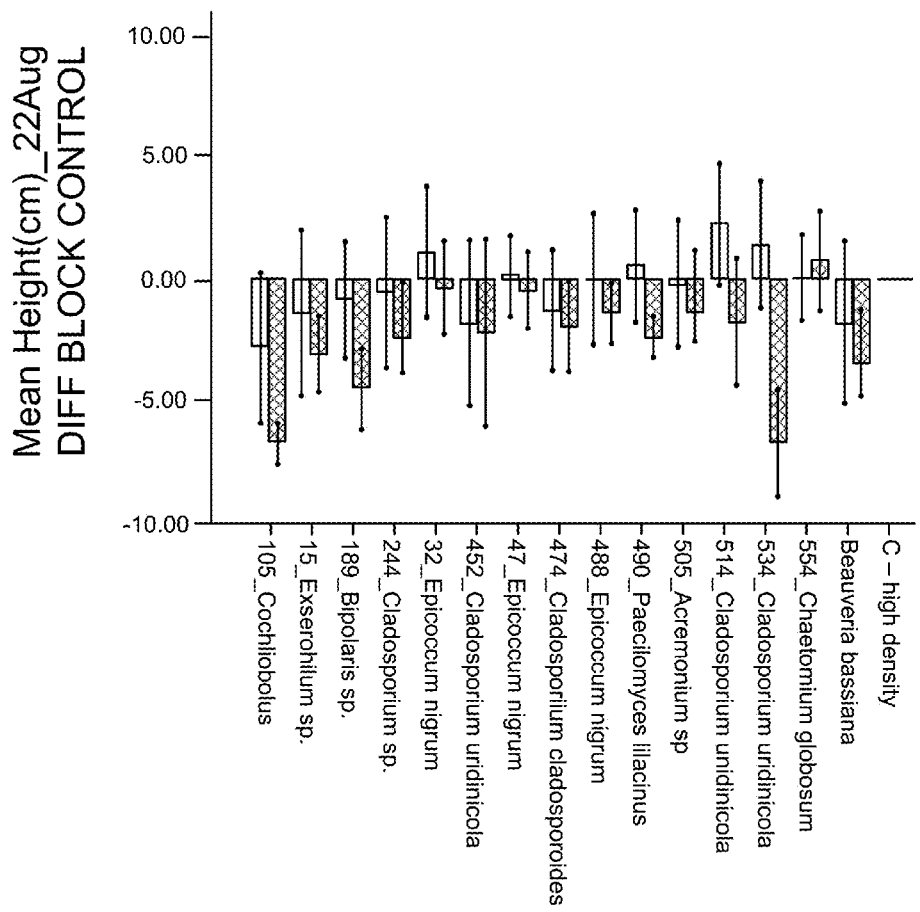

FIG. 22: Mid-season field-trait measured in July at the dryland trial of plant height (cm) for the (open bars) Delta Pine and (hatched bars) Phyton cultivars. Data presented is the block-controlled average of n=10 independent replicates, relative to the control plot and error bars represent ±one standard error.

Figure 23:

FIG. 23: Picture showing increased biomass in the plants treated with endophytes (right half of the image) compared to untreated control (left half of the image).

FIG. 24: Table showing the time to wilt following drought stress in days for plants grown from seeds treated with fungal endophytes and control.

FIG. 25: Table showing the time to death following drought stress in days for plants grown from seeds treated with fungal endophytes and control.

DETAILED DESCRIPTION OF THE INVENTION

Endophytic fungi are ubiquitous in nature, infecting virtually all plants in both natural and agronomic ecosystems. Plants commonly harbor a diversity of fungi living within their tissues as asymptomatic endophytes that can provide protection from a range of biotic and abiotic stressors. The present disclosure describes certain fungal endophytes that can be pathogens, parasites or antagonists to plant pathogens, insects, and nematode pests, thereby providing health and performance benefits to crop plants. The symbiotic endophyte-host relationships can provide several general health and fitness benefits to the host plant, such as enhancement of nutrition, increased drought tolerance and/or chemical defense from potential herbivores and often enhanced biomass production. Root-colonizing mycorrhizae survive on photosynthetic carbohydrates from the plant, and in return, aid in the solubilization and uptake of water and minerals to the host, which can lead to the promotion of seed germination and plant growth. Additionally, the association of a fungal endophyte with a host plant often provides protection from pathogens or tolerance to a variety of biotic and abiotic stresses, such as insect infestation, grazing, water or nutrient deficiency, heat stress, salt or aluminum toxicity, and freezing temperatures. Host growth and fitness promotion and protection are thought to be achieved through multiple beneficial properties of the endophyte-host association.

These fungal endophytes provided in Table 1 were originally collected as fungal endophytes of cotton. These endophytic fungi can be inoculated to live within cotton using either seed, soil or foliar applications and exhibited surprisingly beneficial effects by providing protection from pest infestation. Pests can be nematode and/or insect pests. In addition, these endophytic fungi have an unexpected beneficial effect on cotton yield.

Described is the application of beneficial fungi to establish endophytically within crop plants to improve plant performance and yield while conferring protection against insect and nematode pests. In this regard, the present invention overcomes the limitations of the prior art such as the susceptibility of the fungi to degradation by UV light, desiccation or heat after exposure to the environment following application as an inundative soil or foliar biopesticide. Inoculation and endophytic establishment of the fungi within the plant protects the fungi from UV light, desiccation, and unfavorable temperatures, while harboring the fungi in the very plant tissues they are intended to protect. Introducing fungi to live endophytically within plants requires no genetic modification of the plant or microorganisms, and the fungi themselves can be a source for natural products. In various embodiments, the fungal inoculant can be formulated and applied, for example, as treatment of seeds, in furrow applications, before or during planting, or as foliar application after plant germination, and after inoculation, the fungal endophytes provide season-long protective effects and higher crop yields (approximately 25% higher). In certain embodiments, the increase of yield is about 5%, 10%, 15%, 20%, 30%, 40%, 45%, 50%, or greater than 50% relative to a crop to which no endophyte composition has been applied. In further embodiments, the increase of yield is the result of reduction of loss that comprises reduction of loss due to insect infestation or drought and the loss is less than 50%, 40%, 30%, 20%, 10%, 5%, or 5% relative to a crop to which no endophyte composition has been applied. In certain embodiments, the crop is cotton and the reduction of loss comprises reduced boll damage.

Thus, in one aspect, the invention provides a combination (also termed a "symbiotum") of a host plant and an endophyte that allows for improved agronomic properties of host plants. The combination may be achieved by artificial inoculation, application, or other infection of a host plant or seeds thereof, such as a cotton plant or seed thereof, or host plant tissues, with a fungal endophyte strain of the present invention. Thus, a combination achieved by such an inoculation is termed a "synthetic" combination, synthetic composition, synthetic seed coating, and/or synthetic pest-resistant seed composition. The fungal endophyte may be present in intercellular spaces within plant tissue, such as the root. Its presence may also occur or may also be maintained within a plant or plant population by means of grafting or other inoculation methods such as treating seeds, plants or parts thereof with endophyte mycelia, or endophyte spores. In certain embodiments, the plant, part of the plant, roots, seed, or leaves are sterilized to remove microorganisms before applying the endophyte. In particular embodiments, seeds are sterilized to remove native endophytes before adding the endophyte compositions herein described. In certain aspects, the ability of the seed to germinate is not affected by the sterilization.

The invention also provides methods for detecting the presence of the fungal endophyte of the present invention within a host plant. This may be accomplished, for instance, by isolation of total DNA from tissues of a potential plant-endophyte combination, followed by PCR, or alternatively, Southern blotting, western blotting, or other methods known in the art, to detect the presence of specific nucleic or amino acid sequences associated with the presence of a fungal endophyte strain of the present invention. Alternatively, biochemical methods such as ELISA, HPLC, TLC, or fungal metabolite assays may be utilized to determine the presence of an endophyte strain of the present invention in a given sample of crop tissue. Additionally, methods for identification may include microscopic analysis, such as root staining, or culturing methods, such as grow out tests or other methods known in the art (Deshmukh et al. 2006). In particular embodiments, the roots of a potential grass plant-endophyte combination may be stained with fungal specific stains, such as WGA-Alexa 488, and microscopically assayed to determine fungal root associates.

In certain embodiments, the agronomic qualities may be selected from the group consisting of: increased biomass, increased tillering, increased root mass, increased flowering, increased seed yield, and enhanced resistance to biotic and/or abiotic stresses, each of these qualities being rated in comparison to otherwise identical plants grown under the same conditions, and differing only with respect to the presence or absence of a fungal endophyte. The synthetic combinations and methods of the present invention may be applied to respond to actual or anticipated stresses. Such stresses may include, for instance, drought (water deficit), cold, heat stress, nutrient deficiency, salt toxicity, aluminum toxicity, grazing by herbivores, insect infestation, nematode infection, and fungal, bacteria or viral infection, among others.

The present disclosure provides, in one embodiment, fungal endophytes selected from those in Table 1 that negatively affect the reproduction of insect herbivores feeding on leaves above ground (cotton aphids, *Aphis gossypii*) and plant parasitic nematodes attacking roots below ground (root knot nematodes, *Meloidogyne incognita*). In addition, improved plant performance and yields in colonized versus uncolonized control plants may be observed in field trials employing seed treatment with such endophytes. Plant growth enhancement and increased resistance to root knot nematodes was demonstrated in cotton, for example, employing *Chaetomium globosum* as an endophyte in greenhouse trials. In addition and as a further non-limiting illustrative example, using *Beauveria bassiana* as an endophyte in cotton, reductions in insect (cotton aphid) reproduction was demonstrated in both greenhouse and field trials. The endophytic presence of *Paecilomyces lilacinus* and *Beauveria bassiana* also had negative effects on the host selection behavior of key sucking bug pests (*Lygus hesperus* and *Nezara viridula*) that attack developing flowers and fruits in cotton. Furthermore, in field trials using *Beauveria bassiana* as an endophyte in cotton positive effects on plant performance and higher yields in endophyte colonized versus uncolonized control plants was demonstrated.

Metabolomic differences between the plants can be detected using methods known in the art. For example, a biological sample (whole tissue, exudate, phloem sap, xylem sap, root exudate, etc.) from the endophyte-associated and reference agricultural plants can be analyzed essentially as described in Fiehn et al., (2000) Nature Biotechnol., 18, 1157-1161, or Roessner et al., (2001) Plant Cell, 13, 11-29. Such metabolomic methods can be used to detect differences in levels in hormones, nutrients, secondary metabolites, root exudates, phloem sap content, xylem sap content, heavy metal content, and the like.

In another embodiment, the present invention contemplates methods of coating the seed of a plant with a plurality of endophytes, as well as seed compositions comprising a plurality of endophytes on and/or in the seed. The methods according to this embodiment can be performed in a manner similar to those described herein for single endophyte coating. In one example, multiple endophytes can be prepared in a single preparation that is coated onto the seed. The endophytes can be from a common origin (i.e., a same plant). Alternatively, the endophytes can be from different plants.

Where multiple endophytes are coated onto the seed, any or all of the endophytes may be capable of conferring a beneficial trait onto the host plant. In some cases, all of the endophytes are capable of conferring a beneficial trait onto the host plant. The trait conferred by each of the endophytes may be the same (e.g., both improve the host plant's tolerance to a particular biotic stress), or may be distinct (e.g., one improves the host plant's tolerance to drought, while another improves phosphate utilization). In other cases the conferred trait may be the result of interactions between the endophytes.

Definitions

In the description and tables herein, a number of terms are used. In order to provide a clear and consistent understanding of the specification and claims, the following definitions are provided. Unless otherwise noted, terms are to be understood according to conventional usage by those of ordinary skill in the relevant art.

When a term is provided in the singular, the inventors also contemplate aspects of the invention described by the plural of that term. The singular form "a," "an," and "the" include plural references unless the context clearly dictates otherwise. For example, the term "a cell" includes one or more cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and agriculturally acceptable carriers. "Consisting of" shall mean excluding more than trace elements of other ingredients and substantial method steps for applying the compositions of this invention. Embodiments defined by each of these transition terms are within the scope of this invention.

Biological control: the term "biological control" and its abbreviated form "biocontrol," as used herein, is defined as control of a pest, pathogen, or insect or any other undesirable organism by the use of at least one endophyte.

A "composition" is intended to mean a combination of active agent and at least another compound, carrier or composition, inert (for example, a detectable agent or label or liquid carrier) or active, such as a pesticide.

As used herein, an "agricultural seed" is a seed used to grow plants in agriculture (an "agricultural plant"). The seed may be of a monocot or dicot plant, and is planted for the production of an agricultural product, for example grain, food, fiber, etc. As used herein, an agricultural seed is a seed that is prepared for planting, for example, in farms for growing. Agricultural seeds are distinguished from commodity seeds in that the former is not used to generate products, for example commodity plant products.

As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts;

dehydrated plant tissue, frozen plant tissue, and processed plant tissue; seeds and plant parts processed for animal feed for terrestrial and/or aquatic animal consumption, oil, meal, flour, flakes, bran, fiber, and any other food for human or animal consumption; and biomasses and fuel products. Any such commodity plant product that is derived from the plants of the present invention may contain at least a detectable amount of the specific and unique DNA corresponding to the endophytes described herein. Any standard method of detection for polynucleotide molecules may be used, including methods of detection disclosed herein.

As used herein, the phrase "agronomically elite plants" refers to a genotype or cultivar with a phenotype adapted for commercial cultivation. Traits comprised by an agronomically elite plant may include biomass, carbohydrate, and/or seed yield; biotic or abiotic stress resistance, including drought resistance, insect resistance, fungus resistance, virus resistance, bacteria resistance, cold tolerance, and salt tolerance; improved standability, enhanced nutrient use efficiency, and reduced lignin content.

In certain embodiments, cotton agronomically elite plants include, for example, known cotton varieties AM 1550 B2RF, NG 1511 B2RF, NG 1511 B2RF, FM 1845LLB2, FM 1944GLB2, FM 1740B2F, PHY 499 WRF, PHY 375 WRF, PHY 367 WRF, PHY 339 WRF, PHY 575 WRF, DP 1252 B2RF, DP 1050 B2RF, DP 1137 B2RF, DP 1048 B2RF, and/or DP 1137 B2RF.

As used herein, the phrase "culture filtrate" refers to broth or media obtained from cultures inoculated with a strain of fungi and allowed to grow. The media is typically filtered to remove any suspended cells, leaving the nutrients, hormones, or other chemicals.

As used herein, the term "endophyte" refers to an organism capable of living within a plant or plant tissue. An endophyte may comprise a fungal organism that may confer an increase in yield, biomass, resistance, or fitness in its host plant. Fungal endophytes may occupy the intracellular or extracellular spaces of plant tissue, including the leaves, stems, flowers, or roots.

The phrase "pest resistance" refers to inhibiting or reducing attack from pests. Pest resistance provides at least some increase in pest resistance over that which is already possessed by the plant.

As used herein, the term "genotypes" refers to the genetic constitution of a cell or organism.

As used herein, the term "phenotype" refers to the detectable characteristics of a cell or organism, which characteristics are either the direct or indirect manifestation of gene expression.

As used herein, the phrase "host plant" refers to any plant that an endophytic fungi colonizes. In certain embodiments, the host plant comprises progeny of colonized plant.

As used herein, the phrase "increased yield" refers to an increase in biomass or seed weight, seed or fruit size, seed number per plant, seed number per unit area, bushels per acre, tons per acre, kilo per hectare, carbohydrate yield, or cotton yield. Such increased yield is relative to a plant or crop that has not been inoculated with the endophyte. In certain embodiments, the increase yield is relative to other commonly used pest treatments or other methods of addressing the biotic or abiotic stress.

As used herein, the phrase "biomass" means the total mass or weight (fresh or dry), at a given time, of a plant tissue, plant tissues, an entire plant, or population of plants, usually given as weight per unit area. The term may also refer to all the plants or species in the community (community biomass).

As used herein, "sticker" refers to compounds to enhance binding of spores to the seed surface. Non-limiting examples of such compounds are alginic acid, carrageenan, dextrin, dextran, pelgel, polyethelene glycol, polyvinyl pyrrolidone, methyl cellulose, polyvinyl alcohol, or gelatin.

As used herein, an "agriculturally acceptable" excipient or carrier is one that is suitable for use in agriculture without undue adverse side effects to the plants, the environment, or to humans or animals who consume the resulting agricultural products derived therefrom commensurate with a reasonable benefit/risk ratio.

As used herein, the term "synthetic" or the phrase "synthetic combination" refers to an artificial combination that includes mycelia and/or spores of a endophyte that is or leads to an endophytic fungal-host relationship (also termed a "symbiotum") of a host plant and an endophyte. The synthetic combination may be achieved, for example, by artificial inoculation, application, or other infection of a host plant, host plant seeds, or host plant tissues with the endophyte. In addition, the combination of host plant and an endophyte may be achieved by inoculating the soil or growth media of the plant.

The present invention contemplates the use of "isolated" microbe. As used herein, an isolated microbe is a microbe that is isolated from its native environment, and carries with it an inference that the isolation was carried out by the hand of man. An isolated microbe is one that has been separated from at least some of the components with which it was previously associated (whether in nature or in an experimental setting) or occurs at a higher concentration, viability, or other functional aspect than occurring in its native environment. Therefore, an "isolated" microbe is partially or completely separated from any other substance(s) as it is found in nature or as it is cultured, propagated, stored or subsisted in naturally or non-naturally occurring environments. Specific examples of isolated microbes include partially pure microbes, substantially pure microbes and microbes cultured in a medium that is non-naturally occurring.

As used herein, a microbe is considered to be "native" to a plant or a portion of the plant, and is said to be "natively" present in the plant or a portion of plant, if that plant or portion of the plant contains the microbe, for example, in the absence of any contacting with the microbe preparation, or contains the microbe at much lower concentrations than the contacting with the microbe preparation would provide.

Some of the methods described herein allow the colonization of plant seeds by microbes. As used herein, a microbe is said to "colonize" a plant or seed when it can exist in a symbiotic or non-detrimental relationship with the plant in the plant environment, for example on, in close proximity to or inside a plant, including the seed.

A "population" of plants, as used herein, refers to a plurality of plants that were either grown from the seeds treated with the endophytes as described herein, or are progeny of a plant or group of plants that were subjected to the inoculation methods. The plants within a population are typically of the same species, and/or typically share a common genetic derivation.

EXAMPLES

Example 1: Creating Spore Suspensions and Treatment of Seeds

Cultivation of plants and endophytic fungi strains: The cotton seed variety used in particular embodiments was variety LA122 (available from All-Tex Seed, Inc., Levelland, Tex. 79336). *Paecilomyces lilacinus* and *Chaetomium globosum* were obtained from cotton plants as described (Ek-Ramos et al. 2013, PLoS ONE 8(6): e66049. doi: 10.1371/journal.pone.0066049). Persons of ordinary skill in the art can obtain endophytes suitable for performing the various embodiments of the present invention by performing the procedures described therein. In short, plant samples were rinsed in tap water and surface sterilized by immersion in 70% ethanol for 5 min, 10% bleach solution for 3 min, and rinsed twice with autoclaved distilled water. Samples were blotted dry using autoclaved paper towels. Five individual surface sterilized leaves, squares and bolls (N=15 total samples) were randomly selected and imprinted onto fresh potato dextrose agar (PDA) and V8 media as a way to monitor surface sterilization efficiency. For endophyte isolation, leaves were cut in small fragments of approximately 1 cm². Squares and bolls were cut in six pieces. Any fiber present was removed and cut into six smaller pieces. Leaf fragments were placed upside down on PDA and V8 medium plates in triplicate. Each plate contained 3 leaf fragments for a total of 9 fragments assayed per plant. For squares collected early in the season, 3 slices per square were plated on PDA and V8 media as with the leaf fragments. Because of similarity in size and location within a plant, when collected later in the season, squares and bolls from a given plant were plated together on petri dishes containing two square slices, two boll slices and two pieces of fiber. Antibiotics Penicillin G (100 Units/mL) and Streptomycin (100 µg/mL) (Sigma, St Louis, Mo., USA) were added to the media to suppress bacterial growth. All plates were incubated in the dark at room temperature for, in average, two weeks until growth of fungal endophyte hyphae from plant tissues was detected.

An inclusive combination of morphological and molecular fungal endophyte identification was employed for identification. Once fungal hyphae were detected growing from the plant material, samples were taken to obtain pure fungal isolates. For identification by PCR, genomic DNA was extracted from mycelium of each isolated fungal strain, following a chloroform:isoamyl alcohol 24:1 protocol and fungal specific primers were used to amplify the ITS (Internal Transcribed Spacer) region of nuclear ribosomal DNA. This region is the primary barcoding marker for fungi and includes the ITS1 and ITS2 regions, separated by the 5.8S ribosomal gene. In order to avoid introducing biases during PCR (taxonomy bias and introduction of mismatches), it has been suggested to amplify the ITS1 region only, therefore the primers ITS1 (5' TCC GTA GGT GAA CCT GCG G 3') (SEQ ID NO:5) and ITS2 (5' GCT GCG TTC TTC ATC GAT GC 3') (SEQ ID NO:6) were used to amplify and sequence the ~240 bp ITS1 region of each one of the isolated fungal strains. The resulting sequences were aligned as query sequences with the publicly available databases GenBank nucleotide, UNITE and PlutoF. The last two are specifically compiled and used for fungi identification. Table 1 provides a list of endophytes identified and useful in the present invention. All of these endophytes belong to phylum Ascomycota, subphylum Pezizomycotina, except for *Phanerochaete crassa*, which belongs to phylum Basidiomycota, subphylum Agaricomycotina, and *Pseudozyma* sp, which belongs to phylum Basidiomycota, subphylum Ustilaginomycotina. Table 1 shows the species/genus, family, order, subclass, class, and the SEQ ID NO corresponding to the ~240 bp ITS1 region for each one of the isolated fungal strains, except for *Beauveria bassiana, Aspergillus parasiticus, Lecanicillium lecanii*, and *Paecilomyces lilacinus*, where the sequences shown includes the ITS1, ITS2, 5.8S, 18S, and 28S sequences and were obtained from the UNITE database for GenBank numbers JF837090, JX857815, FJ643076, and EU553283, respectively.

TABLE 1 endophytes identified and useful in the present invention

| Genus/Species | Family | Order | Subclass | Class | SEQ ID NO. |
|---|---|---|---|---|---|
| *Acremonium alternatum* | Incertaesedis | Hypocreales | Hypocreomycetidae | Sordariomycetes | 7 |
| *Alternaria alternata* | Pleosporaceae | Pleosporales | Pleosporomycetidae | Dothideomycetes | 8 |
| *Alternaria brassicae* | Pleosporaceae | Pleosporales | Pleosporomycetidae | Dothideomycetes | 9 |
| *Alternaria compacta* | Pleosporaceae | Pleosporales | Pleosporomycetidae | Dothideomycetes | 10 |
| *Alternaria dianthi* | Pleosporaceae | Pleosporales | Pleosporomycetidae | Dothideomycetes | 11 |
| *Alternaria longipes* | Pleosporaceae | Pleosporales | Pleosporomycetidae | Dothideomycetes | 12 |
| *Alternaria mali* | Pleosporaceae | Pleosporales | Pleosporomycetidae | Dothideomycetes | 13 |
| *Alternaria sesami* | Pleosporaceae | Pleosporales | Pleosporomycetidae | Dothideomycetes | 14 |
| *Alternaria solani* | Pleosporaceae | Pleosporales | Pleosporomycetidae | Dothideomycetes | 15 |
| *Alternaria* sp. | Pleosporaceae | Pleosporales | Pleosporomycetidae | Dothideomycetes | 16 |
| *Alternaria tenuissima* | Pleosporaceae | Pleosporales | Pleosporomycetidae | Dothideomycetes | 17 |
| *Bipolaris spicifera* | Pleosporaceae | Pleosporales | Pleosporomycetidae | Dothideomycetes | 18 |
| *Cercospora canescens* | Mycosphaerellaceae | Capnodiales | Dothideomycetidae | Dothideomycetes | 19 |
| *Cercospora capsici* | Mycosphaerellaceae | Capnodiales | Dothideomycetidae | Dothideomycetes | 20 |
| *Cercospora kikuchii* | Mycosphaerellaceae | Capnodiales | Dothideomycetidae | Dothideomycetes | 21 |
| *Cercospora zinnia* | Mycosphaerellaceae | Capnodiales | Dothideomycetidae | Dothideomycetes | 22 |
| *Chaetomium globosum* | Chaetomiaceae | Sordariales | Sordariomycetidae | Sordariomycetes | 23 |

TABLE 1-continued endophytes identified and useful in the present invention

| Genus/Species | Family | Order | Subclass | Class | SEQ ID NO. |
|---|---|---|---|---|---|
| *Chaetomium piluliferum* | Chaetomiaceae | Sordariales | Sordariomycetidae | Sordariomycetes | 24 |
| *Chaetomium* sp. | Chaetomiaceae | Sordariales | Sordariomycetidae | Sordariomycetes | 25 |
| *Cladosporium cladosporioides* | Cladosporiaceae | Capnodiales | Dothideomycetidae | Dothideomycetes | 26 |
| *Cladosporium* sp. | Cladosporiaceae | Capnodiales | Dothideomycetidae | Dothideomycetes | 27 |
| *Cladosporium uredinicola* | Cladosporiaceae | Capnodiales | Dothideomycetidae | Dothideomycetes | 28 |
| *Cochliobolus* sp | Pleosporaceae | Pleosporales | Pleosporomycetidae | Dothideomycetes | 29 |
| *Phanerochaete crassa* | Phanerochaetaceae | Polyporales | Incertae sedis | Agaricomycetes | 30 |
| *Phoma americana* | Incertae sedis | Pleosporales | Pleosporomycetidae | Dothideomycetes | 31 |
| *Phoma subherbarum* | Incertae sedis | Pleosporales | Pleosporomycetidae | Dothideomycetes | 32 |
| *Phomopsis liquidambari* | Diaporthaceae | Diaporthales | Sordariomycetidae | Sordariomycetes | 33 |
| *Phomopsis* sp. | Diaporthaceae | Diaporthales | Sordariomycetidae | Sordariomycetes | 34 |
| *Pleospora* sp. | Pleosporaceae | Pleosporales | Pleosporomycetidae | Dothideomycetes | 35 |
| *Pleosporaceae* sp. | Pleosporaceae | Pleosporales | Pleosporomycetidae | Dothideomycetes | 36 |
| *Preussia africana* | Sporormiaceae | Pleosporales | Pleosporomycetidae | Dothideomycetes | 37 |
| *Preussia* sp. | Sporormiaceae | Pleosporales | Pleosporomycetidae | Dothideomycetes | 38 |
| *Pseudozyma* sp. | Ustilaginaceae | Ustilaginales | Ustilaginomycetidae | Ustilaginomycetes | 39 |
| *Pyrenophora teres* | Pleosporaceae | Pleosporales | Pleosporomycetidae | Dothideomycetes | 40 |
| *Colletotrichum capsici* | Glomerellaceae | Incertae sedis | Sordariomycetidae | Sordariomycetes | 41 |
| *Coniolariella gamsii* | Incertae sedis | Xylariales | Xylariomycetidae | Sordariomycetes | 42 |
| *Coniothyrium aleuritis* | Coniothyriaceae | Pleosporales | Pleosporomycetidae | Dothideomycetes | 43 |
| *Coniothyrium* sp. | Coniothyriaceae | Pleosporales | Pleosporomycetidae | Dothideomycetes | 44 |
| *Corynespora cassiicola* | Corynesporascaceae | Pleosporales | Pleosporomycetidae | Dothideomycetes | 45 |
| *Diaporthe* sp. | Diaporthaceae | Diaporthales | Sordariomycetidae | Sordariomycetes | 46 |
| *Diatrype* sp. | Diatrypaceae | Xylariales | Xylariomycetidae | Sordariomycetes | 47 |
| *Drechslerella dactyloides* | Orbiliaceae | Orbiliales | Orbiliomycetidae | Orbiliomycetes | 48 |
| *Embellisia indefessa* | Pleosporaceae | Pleosporales | Pleosporomycetidae | Dothideomycetes | 49 |
| *Epicoccum nigrum* | Pleosporaceae | Pleosporales | Pleosporomycetidae | Dothideomycetes | 50 |
| *Epicoccum* sp. | Pleosporaceae | Pleosporales | Pleosporomycetidae | Dothideomycetes | 51 |
| *Exserohilum rostratum* | Pleosporaceae | Pleosporales | Pleosporomycetidae | Dothideomycetes | 52 |
| *Fusarium chlamydosporum* | Nectriaceae | Hypocreales | Hypocreomycetidae | Sordariomycetes | 53 |
| *Fusarium* sp. | Nectriaceae | Hypocreales | Hypocreomycetidae | Sordariomycetes | 54 |
| *Gibellulopsis nigrescens* | Plectosphaerellaceae | Incertae sedis | Hypocreomycetidae | Sordariomycetes | 55 |
| *Gnomoniopsis* sp. | Glomerellaceae | Incertae sedis | Hypocreomycetidae | Sordariomycetes | 56 |
| *Lewia infectoria* | Pleosporaceae | Pleosporales | Pleosporomycetidae | Dothideomycetes | 57 |
| *Mycosphaerella coffeicola* | Mycosphaerellaceae | Capnodiales | Dothideomycetidae | Dothideomycetes | 58 |
| *Mycosphaerellaceae* sp. | Mycosphaerellaceae | Capnodiales | Dothideomycetidae | Dothideomycetes | 59 |
| *Nigrospora oryzae* | Incertae sedis | Trichosphaeriales | Incertae sedis | Sordariomycetes | 60 |
| *Nigrospora* sp. | Incertae sedis | Trichosphaeriales | Incertae sedis | Sordariomycetes | 61 |
| *Nigrospora sphaerica* | Incertae sedis | Trichosphaeriales | Incertae sedis | Sordariomycetes | 62 |
| *Paecilomyces* sp. | Trichocomaceae | Eurotiales | Eurotiomycetidae | Eurotiomycetes | 63 |
| *Penicillium citrinum* | Trichocomaceae | Eurotiales | Eurotiomycetidae | Eurotiomycetes | 64 |
| *Retroconis* sp. | Incertae sedis | Incertae sedis | Incertae sedis | Incertae sedis | 65 |
| *Rhizopycnis* sp. | Incertae sedis | Incertae sedis | Incertae sedis | Dothideomycetes | 66 |
| *Schizothecium inaequale* | Lasiosphaeriaceae | Sordariales | Sordariomycetidae | Sordariomycetes | 67 |
| *Stagonospora* sp. | Phaeosphaeriaceae | Pleosporales | Pleosporomycetidae | Dothideomycetes | 68 |
| *Stemphylium lancipes* | Pleosporaceae | Pleosporales | Pleosporomycetidae | Dothideomycetes | 69 |
| *Thielavia hyrcaniae* | Chaetomiaceae | Sordariales | Sordariomycetidae | Sordariomycetes | 70 |

TABLE 1-continued endophytes identified and useful in the present invention

| Genus/Species | Family | Order | Subclass | Class | SEQ ID NO. |
|---|---|---|---|---|---|
| *Thielavia* sp. | Chaetomiaceae | Sordariales | Sordariomycetidae | Sordariomycetes | 71 |
| *Ulocladium chartarum* | Pleosporaceae | Pleosporales | Pleosporomycetidae | Dothideomycetes | 72 |
| *Verticillium* sp. | Plectosphaerellaceae | Incertae sedis | Hypocreomycetidae | Sordariomycetes | 73 |
| *Beauveria bassiana* | Cordycipitaceae | Hypocreales | Hypocreomycetidae | Sordariomycetes | 74 |
| *Aspergillus parasiticus* | Trichocomaceae | Eurotiales | Eurotiomycetidae | Eurotiomycetes | 75 |
| *Lecanicillium lecanii* | Cordycipitaceae | Hypocreales | Hypocreomycetidae | Sordariomycetes | 76 |
| *Paecilomyces lilacinus* | Trichocomaceae | Eurotiales | Eurotiomycetidae | Eurotiomycetes | 77 |

TABLE 1 List of endophytes:

*Acremonium alternatum, Alternaria alternata, Ahernaria brassicae, Alternaria compacta, Alternaria dianthi, Alternaria longipes, Ahernaria mali, Ahernaria sesami, Alternaria solani, Alternaria* sp., *Alternaria tenuissima, Ascomycota* sp. *Bipolaris spicifera, Cercospora canescens, Cercospora capsici, Cercospora kikuchii, Cercospora zinnia, Chaetomium globosum, Chaetomium piluliferum, Chaetomium* sp., *Cladosporium cladosporioides, Cladosporium* sp., *Cladosporium uredinicola, Cochliobolus* sp, *Phanerochaete crassa, Phoma americana, Phorna subherbarum, Phomopsis liquidambari, Phomopsis* sp., *Pleospora* sp., *Pleosporaceae* sp., *Polyporales* sp., *Preussia africana, Preussia* sp., *Pseudozyma* sp., *Pyrenophora teres, Colletotrichumcapsici, Coniolariella gamsii, Coniothyrium aleuritis, Coniothyrium* sp., *Corynespora cassiicola, Diaporthe* sp., *Diatrype* sp., *Drechslerella dactyloides, Embellisia indefessa, Epicoccum nigrum, Epicoccum* sp., *Exserohilum rostratum, Fusarium chlamydosporum, Eusarium* sp., *Gibellulopsis nigrescens, Gnomoniopsis* sp., *Lewia injectoria, Mycosphaerella cojffeicola, Mycosphaerellaceae* sp., *Nigrospora oryzae, Nigrospora* sp., *Nigrospora sphaerica, Paecilomyces* sp., *Penicillium citrinum, Reiroconis* sp., *Rhizopycnis* sp., *Schizothecium inaequale, Stagonospora* sp., *Stemphylium kancipes, Thielavia hyrcaniae, Thielavia* sp., *Ulocladium chartarum, Verticillium* sp., *Beauveria bassiana, Aspergillus parasiticus, Lecanicillium lecanii, Paecilomyces lilacinus.*

*Beauveria bassiana* was cultured from a commercially obtained strain (available from Botanigard). *Beauveria bassiana, Paecilomyces lilacinus,* and *Chaetomium globosum* were cultured on potato dextrose agar media (PDA). Stock spore concentration solutions of each fungi were made by adding 10 ml of sterile water to the fungi plates and scraping them free of the agar with a sterile scalpel. The resulting mycelia and spores obtained were then filtered into a sterile beaker utilizing a cheese cloth to filter out the mycelia, thereby creating stock solutions. A haemocytometer was used to measure and calculate spore concentrations of the stock solutions. The desired concentrations were created by dilution, and seeds were placed into spore suspensions with the desired spore concentrations. In various embodiments, the final treatment concentrations can be about $10^2$, $10^3$, $10^4$, $10^5$, $10^6$, $10^7$, $10^8$, or $10^9$ spores/ml which can be reached by serial dilutions in sterile water or in an appropriate solution or buffer.

For seed inoculation, the seeds were surface sterilized prior to soaking them in spore suspensions with the desired concentration by immersion the seeds in 70% ethanol for 3 minutes with constant shaking followed by incubation in 2% NaOCl for 3 minutes; followed by three washes in sterile water. The third sterile water wash was plated onto potato dextrose agar media (PDA) to confirm that surface sterilization was effective. Seeds were then soaked for 24 hours in beakers containing spore suspensions with two different concentrations of fungi. Control group seeds were treated with sterile water only. Spore concentrations for *Beauveria bassiana* were zero (control), $1 \times 10^6$ (treatment 1) and $1 \times 10^9$ (treatment 2) and for *Paecilomyces lilacinus* or *Chaetomium globosum* were zero (control), $1 \times 10^6$ (treatment 1) and $1 \times 10^7$ (treatment 2). These beakers were incubated for 24 hours at 32° C. in a culture chamber until next day for planting (24 hr).

Soaked seeds were planted in L22 mix soil (Borlaug Institute, Texas A&M). All plants were grown in a laboratory greenhouse at ~28° C. with a natural light photoperiod. There was no fertilization of the plants, and watering was done consistently across all treatments as needed.

Direct seed inoculation: In particular embodiments, individual seeds and the surrounding soil can be directly inoculated with the spore solution ($10^2$-$10^3$, $10^3$-$10^4$, $10^4$-$10^5$, $10^6$-$10^7$, or $10^7$-$10^8$ spores/ml) at planting before covering the seed with soil.

In various embodiments, any seed or plant treatments that are suitable for application of biological agents to seeds or plants and known to persons having ordinary skill in the art can be employed.

Example 2: Application of Endophyte Spores as a Dry Powder Composition

In addition to application of a spore solution for seed treatment, the endophytes or endophyte spores can also be applied as dry powder or using a sicker such as methyl cellulose for seed treatment. In certain embodiments, the concentration may be at least $10^5$, $10^6$, $10^7$, $10^8$, $10^9$, or higher colony forming units or spores/g dry weight.

In certain embodiments, endophytes can be grown in fungi cultivation media in a fermenter. Endophytic mycelial fragments or spores can be collected, dried and ground. A sticker such as caboxymethyl cellulose may also be added to the ground endophytic material.

In certain embodiments the weight ratio between endophytic material and sticker may be between 1:10-50, 1:50-100, 1:100-500, or 1:500-1000 to obtain the seed coating or seed inoculation material. This seed inoculation material can be applied to seeds. In various embodiments, the weight ratio between seed inoculation material and seed may be 1:10-50, 1:50-100, 1:100-500, 1:500-1000, or 1:1000-5000.

Example 3: Soil (in Furrow) Endophyte Treatments

Soil drench (in furrow) application may be performed by applying an endophyte composition to the surface of the soil and/or seed during planting. In particular embodiments, the endophyte composition may comprise an endophyte suspension or an endophyte dry powder formulation. In various embodiments the endophyte may comprise mycelia and/or spores. In particular embodiments, the soil drench application may comprise applying the endophyte composition to the surface of the soil directly above each seed. In certain embodiments, the endophyte composition may comprise 0.01-0.1, 0.1-1, or 1-10 ml endophyte suspension, which may be a endophyte spore suspension.

Soil inoculation: In certain embodiments, seeds can be planted into inoculated soil. The inoculum can be obtained by multiplying the endophyte on fungal growth media. The fungal growth media can be potato dextrose agar media (PDA). In other embodiments the fungal growth media can be as wheat grain. In a non-limiting example, 100 g of wheat grain can be washed and soaked overnight in sterile water. Excess water can be drained, seeds dried on paper towel, packed in a 500 ml conical flask and autoclaved at 15 psi for 1 h. One milliliter of the endophytic fungal spore suspension ($10^7$ spores/ml) can be inoculated to the flask, and the cultures can be incubated at 25° C. for 2 weeks. To avoid clumping, the flasks can be shaken vigorously to separate the grain and break the mycelial mat. Approximately 5 g of inoculum can be placed in soil at planting. In certain embodiments, the inoculum can be placed in the soil at the same time or within 1 month of planting the seeds. In certain embodiments, the seeds may comprise sterilized seeds.

Example 4: Foliar Endophyte Treatments

Plants were inoculated via foliar application at the third true leaf stage by spraying the surface of fully expanded leaves to run-off with a spore suspension ($10^8$ spores/ml) using a hand-held plastic sprayer (1 L). In certain embodiments, endophyte spore suspensions were made in water. In certain embodiments, the water was supplemented with a detergent. In a particular non-limiting example, the spore suspension contained 0.02% Triton X 100 as a detergent.

Foliar endophyte treatment may be performed using any suitable method known to a person having ordinary skill in the art. In particular, foliar endophyte treatment may be performed using a sprayer by directly spraying leaves with an endophyte suspension, which may be a endophyte spore suspension.

FIG. 9 demonstrates that foliar application of cotton in the field with spores of endophytic entomopathogenic fungi improved plant performance. Cotton (variety FM1740B2F) seeds were treated with a variety of typical fungicide (Metalaxyl, Triadimenol, Trifloxystrobin, 2-(Thiocyanome-thylthio) benzothioazole) and insecticide (Thiodicarb, Imidacloprid, Chloropyrifos), and seed treatments were planted and grown under field conditions. The plants were sprayed at the 5th true leaf stage with aqueous solutions of *Beauveria bassiana* and *Paecilomyces fumosoroseus*. Sucrose was included (1% wt/vol) as an additional nutritional resource for the fungi. Significantly higher first position boll (developing fruit) retention was observed in plants sprayed with *Beauveria bassiana* without sucrose and *P. fumosoroseus* plus sucrose.

Example 5: Confirmation of Plant Colonization by Endophytic Fungi

Plants were individually placed in plastic bags, which were labeled with plant number, treatment, and final aphid number, and stored in 4° C. until the next day for endophyte confirmation. Half of each plant was utilized for plating on PDA agar and the other half was freeze-dried for to conduct diagnostic PCR assays for endophyte confirmation. The surface sterilization protocol and plating of third sterile water wash on PDA to test for surface contamination was conducted as described above. For diagnostic PCR assays, plant tissue was freeze-dried and DNA was extracted utilizing the CTAB protocol (Doyle & Doyle, 1987, Phytochemistry Bulletin 19:11-15). The oligonucleotide primer sequences synthesized were based upon a NCBI BLAST search corresponding to the laboratory culture sequence results isolated (Ek-Ramos et al., 2013). Sense and antisense oligonucleotide sequences for *Beauveria bassiana* were: 5'-CGGCGGACTCGCCCCAGCCCG-3' (SEQ ID NO:1) and 5'-CCGCGTCGGGGTTCCGGTGCG-3' (SEQ ID NO:2) respectively. The oligonucleotides used to amplify Paecelomyces *lilacinus* were: 5' CTCAGTTGCCTCG-GCGGGAA 3' (SEQ ID NO:3) and 5' GTGCAACTCAGA-GAAGAAATTCCG 3' (SEQ ID NO:4).

The PCR protocol consisted of a denaturation step at 95° C. for 5 min, followed by alignment of oligonucleotides at 56° C. for 2 min and an extension step of 7 min at 72° C. with a total of 35 cycles. The PCR products were visualized in a 2% agarose gel containing 1% ethidium bromide. Electrophoresis was performed at 70 volts for 30 min.

Example 6: Endophytic Fungi can be Manipulated in the Field

A field trial using isolates of *Paecilomyces lilacinus* and *Beauveria bassiana* was conducted during the summer. A randomized block design with five replicate plots that were planted with seeds that were inoculated by soaking for 9 hr in three different aqueous spore concentrations (0, $10^6$, or $10^8$ spores/ml) of the candidate endophyte (such as *Paecilomyces lilacinus* or *Beauveria bassiana*). Each plot consisted of four 15.24 m (40 ft) rows, each separated by 101.6 cm (40 in).

Colonization efficiency: At the first true leaf stage, four plants from each plot for a total of 20 plants per treatment were randomly sampled and tested for colonization by each of the candidate endophytes. Colonization frequencies were determined by incubating surface sterilized root, stem and leaf fragments on PDA media and observing for fungal growth. Colonization frequencies are reported as the number of plants per treatment group with at least one positively colonized plant fragment.

Figure 1:
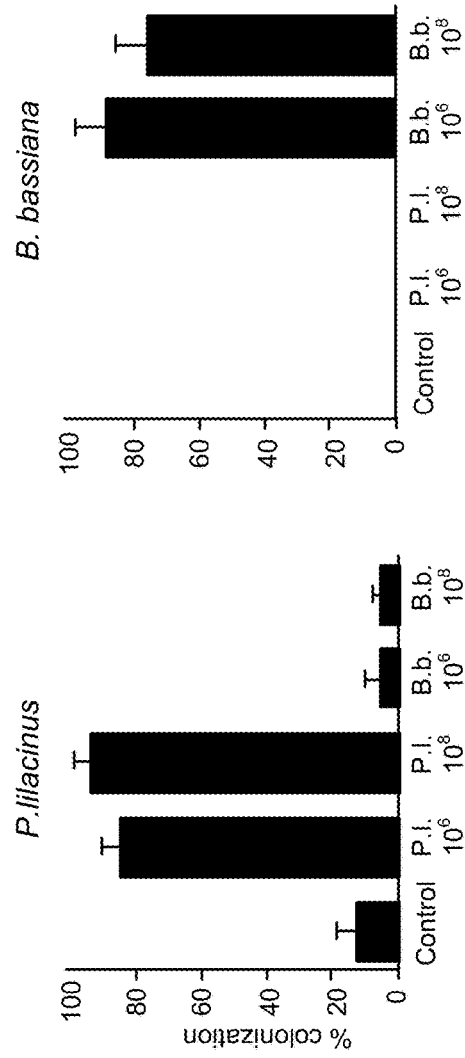
FIG. 1: The colonization efficiencies demonstrate that endophytes can be manipulated in the field. Depicted are the mean+/−SE endophytic colonization frequencies of cotton seedlings under field conditions inoculated by seed treatments with different spore concentrations of either (left) *Paecilomyces lilacinus* or (right) *Beauveria bassiana*.

The high endophytic colonization frequency of seedlings by *Paecilomyces lilacinus* or *Beauveria bassiana* demonstrates that the presence of specific endophytes can be manipulated under field planting conditions (FIG. 1).

Example 7: Cotton Aphid Reproduction Test

A colony of *A. gossypii* was reared on cotton in cages in a greenhouse kept at approximately 28° C. with natural light photoperiod. Second instar nymphs were placed directly onto endophyte-treated cotton plants and control plants. Ten plants were utilized per treatment group and ten aphids were placed per plant. After plants were inoculated with the aphids, the plants were placed in individual plastic 45×20 cm cups and sealed with no-see-um mesh (Eastex products, NJ) to avoid aphid movement from plant to plant. In one embodiment, the plants used were 13 days old, approximately in the first true leaf stage, and aphids were left to reproduce for seven days under greenhouse conditions. In another embodiment, aphids were left to reproduce for 14 days on plants initially 20 days old at the beginning of the experiment, approximately in the third true leaf stage. At the end of each embodiment, aphid numbers were counted and recorded per individual plant. The presence of *Beauveria bassiana* or *Paecilomyces lilacinus* as an endophyte in cotton significantly reduced the reproduction of cotton aphids on endophyte treated plants versus untreated control plants (FIG. 4A, 4B, and FIG. 5)

Example 8: Fungal Endophytes Reduce Nematode Reproduction

Plants were germinated from treated and untreated control seeds in an environment chamber and then transplanted to soil in pots 11 days after planting. Two replicate seedlings per treatment were sampled to examine the endophyte colonization efficiency by surface sterilization and plating on PDA agar. Nematode treatment group seedlings were treated with either 2,000 or 10,000 eggs/plant at day six after transplanting. Plants were harvested and processed 6 weeks after nematode inoculation. The numbers of galls per gram of root tissue and total egg numbers in the population for each plant were quantified to compare nematode performance between endophyte-treated and untreated (control) plants.

Figure 2:
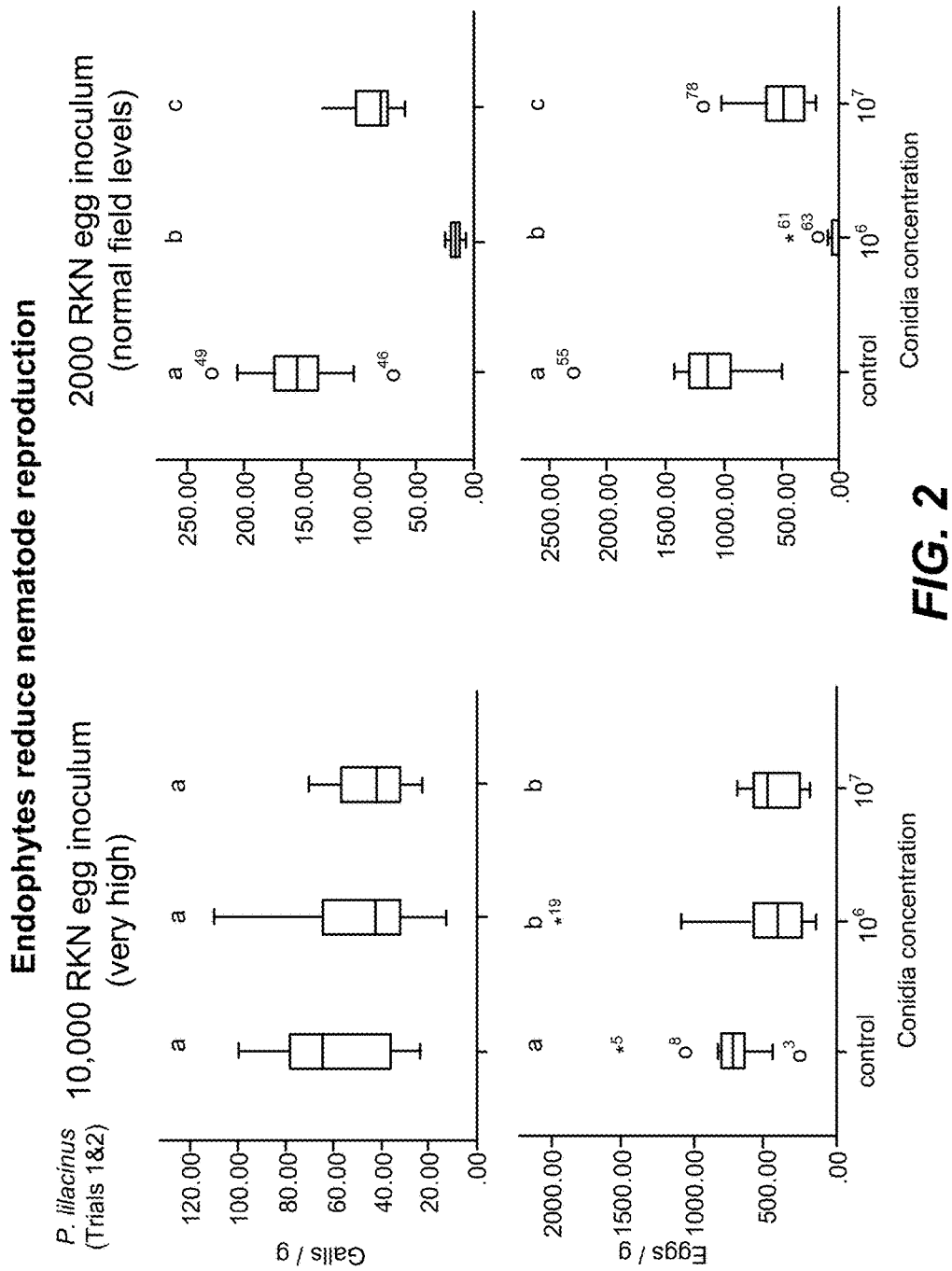
FIG. 2: The endophytic fungus *Paecilomyces lilacinus* negatively affects root knot nematode (*Meloidogyne incognita*) reproduction when present as an endophyte in cotton. At high nematode inoculum levels (10,000 eggs), the endophyte reduced egg production in plants following treatment of seeds with solutions containing either $10^6$ or $10^7$ spores/ ml when compared to untreated control seeds. At field inoculum levels (2000 eggs), the presence of the endophyte significantly reduced both galls and egg production at both seed treatment concentrations.

FIGS. 2 and 3 demonstrate that the endophytic fungi *Paecilomyces lilacinus* and *Chaetomium globosum* negatively affected root knot nematode (*Meloidogyne incognita*) reproduction when present as an endophyte in cotton. At high nematode inoculum levels (10,000 eggs), *Paecilomyces lilacinus* reduced egg production in plants following treatment of seeds with solutions containing either $10^6$ or $10^7$ spores/ml when compared to untreated control seeds. At field inoculum levels (2000 eggs), the presence of *Paecilomyces lilacinus* significantly reduced both galls and egg production at both seed treatment concentrations. Endophytic *Chaetomium globosum* negatively affects root-knot nematode reproduction. Negative effects of endophytic *Chaetomium globosum* on root-knot nematode gall formation and egg production were demonstrated following cotton seed soaking treatments in solutions of 0 (untreated controls), $10^6$ and $10^8$ spores/ml.

Example 9: Effect of Fungal Endophytes on Insects

Endophyte-treated and control plants were grown from non-transgenic cotton seeds (*Gossypium hirsutum*)(variety LA122, AllTex Seed Co.). Seeds were soaked for 24 hours in beakers containing $10^8$ spores/ml solutions of the fungi utilized plus sterile water-only as a control. The beakers were placed in a 32° C. culture chamber overnight (approx. 9 h) until planting the next day. The plants were grown under both greenhouse and field conditions. Greenhouse plants were first germinated in seedling trays and then transferred to 30 cm pots. Field grown plants were concurrently planted and grown.

Behavioral assays: No-choice and choice behavioral assays were conducted to compare the response of western tarnished plant bugs (*L. hesperus*) and green stink bugs (*N. viridula*) to squares and bolls from endophyte-treated and untreated plants. The assays were conducted at 30° C. in 10 cm diameter petri dishes with a thin layer of 2% agar on the bottom to provide moisture for the squares (*L. hesperus* assays) and bolls (*N. viridula* assays) from experimental plants offered to the insects during the observations. For no-choice assays, a single square or boll was inserted by the base into the agar in the center of the dish. A single young adult (1-7 days post molt) insect was placed in each dish and covered with the top. A total of 30 insects were observed in each trial with N=10 insects each in the *Beauveria bassiana*, *Paecilomyces lilacinus* and control treatment groups. The *L. hesperus* no-choice trials were replicated four times (N=40 per treatment) with squares from greenhouse grown plants used in all but one trial. The *N. viridula* no-choice trials were replicated three times (N=20 per treatment) with bolls from greenhouse grown plants used in one trial.

Choice tests were conducted under the similar conditions using the same arenas, but with two equal sized squares (*L. hesperus*) or bolls (*N. viridula*) placed 4 cm apart in the center of the petri dish. The two squares or bolls per arena were from an untreated control plant and either a *Beauveria bassiana* or *Paecilomyces lilacinus* treated plant. A total of 20 insects were observed in each trial, with N=10 each in the *Beauveria bassiana* vs. control and *Paecilomyces lilacinus* vs. control treatment groups. The *L. hesperus* and *N. viridula* choice trials were both replicated twice (N=20 per treatment) with squares from field-grown plants in all trials.

Insects were observed for 6 hours per trial using a point sampling procedure for both the no-choice and choice assays. Preliminary observations indicated that the insects of both species were more active at the beginning of the assay, thus staged sampling schedule was adopted with observations recorded at 5 minute intervals early in the assay (0-60 min), 15 minute intervals in the middle (61-180 min) and 30 minute intervals late (181-360 min) in the assay. At each sampling interval, the insects were recorded as either off the square/boll or feeding or roosting upon the square/boll.

Data analysis: In the no-choice assays, the proportion of insects observed either feeding or resting upon cotton squares (*L. hesperus*) or bolls (*N. viridula*) was compared between treatment groups at each observation point across the duration of the assay using the Wilcoxon Signed Ranks Test. To test for variation in responses over time, for each individual the proportion of observations either feeding or upon the plant sample was calculated for early (0-60 min), middle (61-180 min) and late (181-360 min) periods of the assay and compared across treatment groups using a repeated measures analysis of variance (ANOVA) with the endophyte treatment group as the main factor and time as the repeat effect. The observed frequency of individuals failing to make contact with squares or bolls from endophyte-treated plants was compared to the expected frequency of individuals failing to do so based on the control group using a $X^2$ test. Among the insects that did make contact with either a square or boll, the time to first contact (latency) was compared among treatment groups using a one-way ANOVA. All analyses including tests of normality and homogeneity of variances were conducted in SPSS 21 (SPSS Inc.).

Results of the *L. hesperus* no-choice assays: Over the duration of the assay, a significantly higher proportion of *L. hesperus* individuals over time was observed in contact with and feeding upon squares from untreated control plants relative to those from either of the *Beauveria bassiana* or *Paecilomyces lilacinus* endophyte treatment groups (Wilcoxon Signed Ranks test, P<0.0001 for both comparisons) (FIG. 6A). Repeated measures ANOVA indicated a significant effect of time ($F_{1,116}$=86.175; P<0.001) with a higher proportion of insects contacting the square as the assay progressed (FIG. 6B). There was also a significant effect of endophyte treatment ($F_{2,116}$=4.929; P=0.009) with no significant time X endophyte treatment interaction ($F_{2,116}$=1.015; P=0.366). Of the 40 insects in each treatment group, 12.5% of the control group failed to make contact with the square over the course of the assay, while a significantly higher 35% and 32.5% the *Beauveria bassiana* and *Paecilomyces lilacinus* treatment group insect respectively failed to make contact (X2 test, P<0.0001). Among the insects that did make contact with a square, there was significant difference in the latency to first contact among the treatment groups ($F_{2,85}$=7.225; P<0.0001) with the control group exhibiting a shorter latency to contact than either the *Beauveria bassiana* (posthoc LSD test; P=0.001) or *Paecilomyces lilacinus* endophyte treatment groups (posthoc LSD test; P=0.006 (FIG. 6A).

Results of the *L. hesperus* choice assays: In simultaneous choice tests, *L. hesperus* individuals selected squares from untreated control plants more often than those from endophyte-treated plants. Response ratios were significantly greater than 0.5 over the duration of the assays, indicating that the insects non-randomly selected bolls from control plants over bolls from plants endophytically colonized by either (A) *Beauveria bassiana* (P<0.0001; Wilcoxon Signed Ranks test) or (B) *Paecilomyces lilacinus* (P<0.0001; Wilcoxon Signed Ranks test)(FIG. 6B).

Results of the *N. viridula* no-choice assays: Over the duration of the assay, a significantly higher proportion of *N. viridula* individuals over time was observed in contact with and feeding upon bolls from untreated control plants relative to those from either of the *Beauveria bassiana* or *Paecilomyces lilacinus* endophyte treatment groups (Wilcoxon Signed Ranks test, P<0.0001 for both comparisons)(FIG. 7A). Repeated measures ANOVA indicated a significant effect of time ($F_{1,116}$=86.175; P<0.001) with a higher proportion of insects contacting the square as the assay progressed (FIG. 1), There was also a significant effect of endophyte treatment ($F_{2,116}$=4.929; P=0.009) with no significant time X endophyte treatment interaction ($F_{2,116}$=1.015; P=0.366). Of the 40 insects in each treatment group, 12.5% of the control group failed to make contact with the square over the course of the assay, while a significantly higher 35% and 32.5% the *Beauveria bassiana* and *Paecilomyces lilacinus* treatment group insect respectively failed to make contact (X2 test, P<0.0001). Among the insects that did make contact with a square, there was significant difference in the latency to first contact among the treatment groups ($F_{2,85}$=7.225; P<0.0001) with the control group exhibiting a shorter latency to contact than either the *Beauveria bassiana* (posthoc LSD test; P=0.001) or *Paecilomyces lilacinus* endophyte treatment groups (posthoc LSD test; P=0.006 (FIG. 7B).

Example 10: More Bolls are Retained after Endophyte Treatment

During the field trial, cotton phenology and development was quantified using a plant mapping and information system developed specifically for cotton to track fruit development and retention by the plant as a means of monitoring plant development and stress (COTMAN™, Cotton Inc.). One measure of cotton stress is the retention of developing flowers (squares) and fruits (bolls) in the first fruiting position on branches. First position squares and bolls were measured on 5 plants per row in two rows in each of the five replicate plots (N=10 plants per plot) for each treatment group.

FIG. 10 demonstrates that early in the growing season as flowers begin to develop, a trend for higher square retention in the endophyte-treated plants relative to controls was observed. This trend continued later in the season as evidenced by significantly higher boll retention among the endophyte treatment groups relative to the untreated control plants.

FIG. 8 demonstrates reduction in cotton boll damage during field trials. Relative to control plants, levels of insect-related boll damage were lower among plants that were treated by soaking seeds in spore solutions of *Beauveria bassiana* and *Paecilomyces lilacinus* at concentrations of $10^6$ and $10^8$ spore/ml. Positive effects of fungal endophytes on cotton plant performance under field conditions.

Example 11: Endophyte Treatment Increases Yield

At the end of the field trial employing endophyte treatment and treatment plants, plots were machine harvested with a 1-row picker. Surprisingly, the final yields at harvest were significantly higher than expected (25% higher than the untreated controls). Unexpectedly, treatment with *Paecilomyces lilacinus* or *Beauveria bassiana* resulted in higher yields than untreated control plants with regardless of the initial seed treatment concentration. (FIG. 11)

Example 12: Endophyte Treatment of *Sorghum* Increased Growth in the Greenhouse

The effect of the described microbial compositions on sorghum was tested in a seedling assay. *Sorghum bicolor* seeds were surface sterilized using ethanol and bleach as described in Example 1 for cotton. Three strains (*B. bassiana*, *P. fumosoroseus*, and *P. lilacinus*) were prepared as conidia suspensions at $10^7$ conidia/ml, and coated on the sorghum seeds as described in Example 1. Control seeds were soaked in sterile water instead of a conidia suspension. Planted seeds were held in constant growth chamber conditions for two weeks at a replication of 10. At the end of two weeks, the plants were removed from the growth chamber and the plant height and biomass were measured. FIG. 12A shows the increase in plant height when applied with the described microbial composition relative to the control (p<0.05). FIG. 12B shows the increase in plant biomass in plants grown from seed that were treated with the described microbial composition relative to the control (p<0.05).

Example 13: Treatment with Fungal Endophytes Modulates the Colonization Frequencies of Native Endophytes To determine whether endophyte seed treatments could alter the microbiome of the plant grown from the seed, cotton seeds were treated with spore suspensions of *Paecilomyces lilacinus* or *Beauveria bassiana*. Plants were grown in the field as part of a field trial planted and maintained under standard agricultural practices. Endophytic fungi were isolated on PDA media separately from surface-sterilized above-ground stem/leaf and below-ground root tissue to assess changes in the microbial community. The comparison shown in FIG. 13 is relative to the fungal endophyte communities in untreated control plants. The results show that these treatments can alter the colonization rates of native fungal endophytes.

Fungal endophyte treatments may alter the colonization frequencies of any of the fungal endophytes naturally present in plants. To determine what other native endophytes may be affected by seed treatments with fungal endophytes, the identity of cotton fungal endophytes isolated from plants of two commercial cotton varieties, CG3787B2RF and PHY499WRF, were assessed. The samples were obtained during a variety trial near Lubbock, Tex., USA identified as Lubbock-RACE. One single healthy leaf was collected from each of nine individual plants sampled per variety across multiple replicate plots arranged in a randomized block design to control for spatial variation in the field. To identify the fungal endophyte species, whole genomic DNA was extracted and the ribosomal DNA internal transcribed spacer (ITS) region was amplified as a barcode for 454 pyrosequencing using ITS1F forward and ITS2 reverse universal fusion primers. The fungal endophytes identified in this experiment, along with those shown in FIG. 13, are listed in Table 2.

TABLE 2

Native fungal endophytes that may be altered by seed treatments with other fungal endophytes

| Phylum | Class | Order | Family | Genus species |
|---|---|---|---|---|
| Ascomycota | | | | |
| | Leotiomycetes | | | |
| | Leotiomycetes | | | *Geomyces auratus* |
| | Dothideomycetes | Botryosphaeriales | Botryosphaeriaceae | *Macrophomina* sp. |
| | Dothideomycetes | Capnodiales | Davidiellaceae | |
| | Dothideomycetes | Capnodiales | Davidiellaceae | *Cladosporium* sp. |
| | Dothideomycetes | Capnodiales | Davidiellaceae | *Cladosporium cladosporioides* |
| | Dothideomycetes | Capnodiales | Davidiellaceae | *Davidiella* sp. |
| | Dothideomycetes | Capnodiales | Mycosphaerellaceae | *Cercospora* sp. |
| | Dothideomycetes | Capnodiales | Mycosphaerellaceae | *Cercospora beticola* |
| | Dothideomycetes | Pleosporales | | |
| | Dothideomycetes | Pleosporales | Pleosporaceae | |
| | Dothideomycetes | Pleosporales | Pleosporaceae | *Alternaria* sp. |
| | Dothideomycetes | Pleosporales | Pleosporaceae | *Alternaria alternata* |
| | Dothideomycetes | Pleosporales | Pleosporaceae | *Alternaria citri* |
| | Dothideomycetes | Pleosporales | Pleosporaceae | *Alternaria porri* |
| | Dothideomycetes | Pleosporales | Pleosporaceae | *Alternaria tenuissima* |
| | Dothideomycetes | Pleosporales | Pleosporaceae | *Cochliobolus* sp. |
| | Dothideomycetes | Pleosporales | Pleosporaceae | *Curvularia* sp. |
| | Dothideomycetes | Pleosporales | Pleosporaceae | *Epicoccum* sp. |
| | Dothideomycetes | Pleosporales | Pleosporaceae | *Exserohilum* sp. |
| | Dothideomycetes | Pleosporales | Pleosporaceae | *Lewia* sp. |
| | Dothideomycetes | Pleosporales | Pleosporaceae | *Lewia infectoria* |
| | Dothideomycetes | Pleosporales | Pleosporaceae | *Pyrenophora* sp. |
| | Dothideomycetes | Pleosporales | Pleosporaceae | *Pyrenophora tritici-repentis* |
| | Dothideomycetes | Pleosporales | Pleosporaceae | *Pleospora* sp. |
| | Dothideomycetes | Pleosporales | Didymellaceae | *Phoma americana* |
| | Dothideomycetes | Pleosporales | Sporormiaceae | *Preussia africana* |
| | Eurotiomycetes | Chaetothyriales | | |
| | Eurotiomycetes | Chaetothyriales | Chaetothyriaceae | |
| | Eurotiomycetes | Eurotiales | Trichocomaceae | |
| | Eurotiomycetes | Eurotiales | Trichocomaceae | *Aspergillus* sp. |
| | Eurotiomycetes | Eurotiales | Trichocomaceae | *Penicillium* sp. |
| | Eurotiomycetes | Eurotiales | Trichocomaceae | *Thermomyces* sp. |
| | Eurotiomycetes | Eurotiales | Trichocomaceae | *Thermomyces lanuginosus* |
| | Saccharomycetes | Saccharomycetales | | |
| | Saccharomycetes | Saccharomycetales | Saccharomycetaceae | |
| | Saccharomycetes | Saccharomycetales | Saccharomycetaceae | *Candida* sp. |
| | Saccharomycetes | Saccharomycetales | Saccharomycetaceae | *Candida quercitrusa* |
| | Saccharomycetes | Saccharomycetales | Saccharomycetaceae | *Candida tropicalis* |
| | Saccharomycetes | Saccharomycetales | Saccharomycetaceae | *Cyberlindnera* sp. |
| | Saccharomycetes | Saccharomycetales | Saccharomycetaceae | *Cyberlindnera jadinii* |
| | Saccharomycetes | Saccharomycetales | Saccharomycetaceae | *Kluyveromyces* sp. |
| | Saccharomycetes | Saccharomycetales | Saccharomycetaceae | *Kluyveromyces marxianus* |
| | Sordariomycetes | | | |
| | Sordariomycetes | Diaporthales | Gnomoniaceae | *Gnomoniopsis* sp. |
| | Sordariomycetes | Hypocreales | Cordycipitaceae | *Beauveria bassiana* |
| | Sordariomycetes | Hypocreales | Cordycipitaceae | *Cordyceps* sp. |
| | Sordariomycetes | Hypocreales | Cordycipitaceae | *Cordyceps bassiana* |
| | Sordariomycetes | Hypocreales | Nectriaceae | |
| | Sordariomycetes | Hypocreales | Nectriaceae | *Fusarium* sp. |
| | Sordariomycetes | Hypocreales | Hypocreaceae | |
| | Sordariomycetes | Hypocreales | Hypocreaceae | *Gibellulopsis nigrescens* |
| | Sordariomycetes | Hypocreales | Hypocreaceae | *Hypocrea* sp. |
| | Sordariomycetes | Hypocreales | Hypocreaceae | *Hypocrea lixii* |
| | Sordariomycetes | Hypocreales | Hypocreaceae | *Hypocrea virens* |
| | Sordariomycetes | Hypocreales | Hypocreaceae | *Trichoderma* sp. |
| | Sordariomycetes | Hypocreales | Hypocreaceae | *Trichoderma tomentosum* |
| | Sordariomycetes | Hypocreales | Plectosphaerellaceae | *Verticillium* sp. |
| | Sordariomycetes | Ophiostomatales | Ophiostomataceae | |
| | Sordariomycetes | Ophiostomatales | Ophiostomataceae | *Ophiostoma* sp. |
| | Sordariomycetes | Ophiostomatales | Ophiostomataceae | *Ophiostoma dendifundum* |
| | Sordariomycetes | Sordariales | Chaetomiaceae | *Chaetomium* sp. |
| | Sordariomycetes | Sordariales | Chaetomiaceae | *Chaetomium globosum* |
| | Sordariomycetes | Sordariales | Chaetomiaceae | *Thielavia hyrcaniae* |
| | Sordariomycetes | Sordariales | Chaetomiaceae | *Taifanglania* sp. |

TABLE 2-continued

Native fungal endophytes that may be altered by
seed treatments with other fungal endophytes

| Phylum | Class | Order | Family | Genus species |
|---|---|---|---|---|
| | Sordariomycetes | Sordariales | Chaetomiaceae | *Taifanglania inflata* |
| | Sordariomycetes | Sordariales | Lasiosphaeriaceae | *Schizothecium inaequale* |
| | Sordariomycetes | Trichosphaeriales | Trichosphaeriaceae | *Nigrospora* sp. |
| | Sordariomycetes | Xylariales | Amphisphaeriaceae | *Truncatella angustata* |
| Basidiomycota | Agaricomycetes | Cantharellales | Ceratobasidiaceae | *Rhizoctonia* sp. |
| | Agaricomycetes | Corticiales | Corticiaceae | |
| | Agaricomycetes | Corticiales | Corticiaceae | *Phanerochaete* sp |
| | Agaricomycetes | Polyporales | Coriolaceae | |
| | Agaricomycetes | Polyporales | Coriolaceae | *Trametes* sp. |
| | Agaricomycetes | Polyporales | Coriolaceae | *Trametes hirsuta* |
| | Agaricomycetes | Polyporales | Coriolaceae | *Trametes villosa* |
| | Agaricomycetes | Russulales | Peniophoraceae | |
| | Microbotryomycetes | Sporidiobolales | | |
| | Microbotryomycetes | Sporidiobolales | Sporidiobolaceae | *Rhodotorula* sp. |
| | Microbotryomycetes | Sporidiobolales | Sporidiobolaceae | *Rhodotorula mucilaginosa* |
| | Tremellomycetes | | | |
| | Tremellomycetes | Tremellales | | |
| | Tremellomycetes | Tremellales | Tremellaceae | *Cryptococcus* sp |
| | Tremellomycetes | Tremellales | Tremellaceae | *Cryptococcus skinneri* |
| | Tremellomycetes | Tremellales | Tremellaceae | *Tremella* sp. |

Example 14: Fungal Endophyte Seed Treatment Leads to Modulation of Phytohormone Levels in Plants Grown from the Seed To determine whether fungal endophyte seed treatment affects phytohormone levels in plants grown from the seed, tissue was harvested from the root or third true leaf of cotton plants inoculated with either endophytic *Beauveria bassiana* or *Paecilomyces lilacinus*. The experiment was done with three endophyte treatments (uncolonized control, *B. bassiana* or *P. lilacinus*) and, for *Beauveria bassiana*, two herbivory treatments (no aphids, or aphid herbivory for either 1, 4, 8, 24 or 48 hours). Phytohormone levels for abscisic acid (ABA), tuberonic acid (12-OH-JA, an oxidation product of JA-Ile) (TA), ascorbic acid (AA), 12-Oxophytodienoic acid (a JA precursor) (OPDA), JA isoleucine (JA-Ile), and salicylic acid (SA) were assessed by LC-MS in leaf and root tissues separately. All phytohormone level comparisons were made versus plants in the uncolonized control group with significance at $P<0.05$. Phytohormone levels in plants grown from seed treated with *Beauveria bassiana* are shown in Table 3, and phytohormone levels in plants grown from seed treated with *Paecilomyces lilacinus* are shown in Table 4.

TABLE 3

Phytohormone levels in plants grown from seed treated with *Beauveria bassiana*

| Herbivory | Phytohormone | Tissue | Upregulated/downregulated | Tissue | Upregulated/downregulated |
|---|---|---|---|---|---|
| Yes | ABA | Leaves | Down at 8 hours of feeding | Roots | Upregulated at 48 hrs of feeding |
| No | | | Not significant | | Upregulated |
| Yes | TA | Leaves | Not significant | Roots | Upreguated at 48 hrs of feeding |
| No | | | Not significant | | Not significant |
| Yes | AA | Leaves | Down at 4 hrs up at 24 hrs | Roots | Up at 8 hrs down at 48 hrs |
| No | | | Not significant | | Upregulated |
| Yes | OPDA | Leaves | Not significant | Roots | Up at 4 hrs and 8 hrs |
| No | | | Not significant | | Upregulated |
| Yes | JA-Ile | Leaves | Up at 48 hrs | Roots | Up at 48 hrs |
| No | | | Not significant | | Upregulated |
| Yes | SA | Leaves | Up at 1 hr, 8 hr, 24 and 48 hr | Roots | Down at 4 hr the rest n.s |
| No | | | Not significant | | Not significant |

TABLE 4

Phytohormone levels in plants grown from seed treated with Paecilomyces lilacinus

| | | | | | |
|---|---|---|---|---|---|
| Yes | ABA | Leaves | Down at 48 hrs | Roots | Up at 1 hr and 8 hrs |
| Yes | TA | Leaves | down at 4 and 8 hrs | Roots | up at 4 hrs |
| Yes | AA | Leaves | down at 4 and 8 hrs | Roots | up at 4 hrs |
| Yes | OPDA | Leaves | down at 4 and 8 hrs | Roots | Up at 4 and 48 hrs, down at 24 hrs |
| Yes | JA-Ile | Leaves | Down at 8 and 48 hrs | Roots | Up at 4 and 24 hrs |
| Yes | SA | Leaves | Up at 1 and 4 hr, down at 8 hrs | Roots | Up at 1, down at 8 hrs |

Example 15: Fungal Endophyte Seed Treatments Alter Traits in Certain Cotton Cultivars in Field Trials The 2014 field trials were executed in a similar fashion as described in Example 6. A field trial using isolates of listed below was conducted during the summer. Each plot consisted of four 15.24 m (40 ft) rows, each separated by 101.6 cm (40 in), and there were 6 replicate plots per treatment. Yield from plots treated with the described microbial compositions was compared relative to the untreated control plots. For thrips, this damage assessment was on a scale of 0-5; 0=no damage, 1=noticeable feeding scars, but no stunting, 2=noticeable feeding and 25% stunting, 3=feeding with blackened leaf terminals and 50% stunting, 4=severe feeding and 75% stunting, and 5=severe feeding and 90% stunting. For fleahoppers, the number of insects per plant were quantified and reported as an average for each plot. FIG. 14 shows the yield improvement of crops when treated with the described microbial compositions, for Delta Pine and Phytogen cultivars, respectively. FIG. 15 shows the aggregated yield improvement of the microbes across the two cultivars. Bars represent 95% confidence intervals. FIG. 16A shows the beneficial effect of 12 out of 15 microbial compositions tested on thrip damage in the Delta Pine cultivar. In the Phytogen cultivar, only 2 out of the 15 microbial compositions tested showed a benefit by reducing thrip damage. FIG. 16B shows the beneficial effect of reducing fleahopper damage in the Phytogen cultivar, where 6 out of the 15 facultative fungal endophytes tested showed an average decrease in fleahopper damage as compared to untreated cotton plants. In the Delta Pine cultivar, only one microbial composition showed a beneficial effect on fleahopper damage.

A number of other mid-season plant traits were also assessed in the field to determine the effect of the described fungal endophyte compositions. FIG. 17A shows the beneficial increase of the described microbial compositions on mid-season mean root length. FIG. 17B shows the beneficial increase of the described fungal endophyte compositions on mid-season below ground weight. FIG. 18 shows the beneficial increase of the described fungal endophyte compositions on mid-season canopy temperature for both Delta Pine and Phyton cultivars. FIG. 19 shows the beneficial increase of the described fungal endophyte compositions on mid-season NDVI (Normalized Difference Vegetation Index) for both Delta Pine and Phytogen cultivars. NDVI is a measure of chlorophyll content. FIG. 20 shows the beneficial increase of the described fungal endophyte compositions on mid-season first-position square retention for both Delta Pine and Phytogen cultivars. FIG. 21 and FIG. 22 show the modulation (up in July and down in August) of mid-season plant height when treated with the described fungal endophyte compositions for both Delta Pine and Phytogen cultivars. FIG. 23 shows increased biomass in the plants treated with endophytes (right half of the image) compared to untreated control (left half of the image).

In FIGS. 15 through 22, TAM505 is *Acremonium* sp., TAM32 is *Epicoccum nigrum*, TAM534 is *Cladosporium urdinicola*, TAM244 is *Cladosporium* sp., TAM514 is *Cladosporium urdinicola*, TAM474 is *Cladosporium cladosporoides*, TAM554 is *Chaetomium globosum*, TAM15 is *Exserohilum* sp., TAM488 is *Epicoccum nigrum*, TAM452 is *Cladosporium urdinicola*, TAM490 is *Paecilomyces lilacinus*, TAMBB is *Beauveria bassiana*, TAM105 is *Cochliobolus* sp., TAM189 is *Bipolaris* sp., and TAM47 is *Epicoccum nigrum*.

Example 16: Fungal Endophyte Seed Treatments Provide Drought Tolerance in Cotton Cultivars in Greenhouse Trials Cotton plants were germinated from endophyte-treated and untreated control seeds in the greenhouse. All seeds watered for 7 days or until cotyledon stage using predetermined soil saturation volume of water per plant. At 7 DAP, water was withheld from water stressed plants while controls continued to be watered. Time to wilt and time to death were measured at a max of 21 DAP. The data in FIG. 24 shows the mean time to wilt, and the data in FIG. 25 shows the mean time to death. Endophyte treatment increased the survival of plants subjected to drought stress in both the Delta Pine (DTP) and the Phytogen (PHY) cultivars. In FIGS. 24 and 25, endophyte number 194 is *Epicoccum nigrum*, 249 is *Cladosporium cladosporioides*, 355 is *Chaetomium globusum*, 46 is *Epicoccum* sp., 463 is *Cladosporium* sp., 534 is *Cladosporium uredinicola*, 554 is *Chaetomium globosum*, 58 is *Epicoccum nigrum*, and control is no endophyte treatment.

Example 17: Identification of Fungal Endophytes with at Least 97% Identity to Those in Table 1

All known fungal endophytes with 97% identity to SEQ ID NO:7 through SEQ ID NO:77 were identified and are listed here by accession number: FJ425672, AY526296, JQ760047, UDB014465, KC662098, HQ649874, JQ764783, EU881906, KF251285, JQ862870, AB019364, AB594796, JF773666, JN034678, KC343142, EU707899, AB627855, GU138704, JN695549, DQ279491, HM776417, AB361643, DQ782839, AF222826, EU682199, DQ782833, EU054429, FJ025275, AY354239, AF222828, GU721921, GU721920, DQ093715, AJ309335, FR774125, JQ747741, EF042603, KC968942, HE584924, AY740158, FJ645268, HQ692590, GQ203786, AY233867, HE579398, AB777497, KF435523, DQ420778, JQ649365, AJ271430, GQ996183, EF070423, FJ172277, AF483612, JX675127, EF070420, EF070421, AB741597, JN225408, DQ019364, KF251279, EF194151, EU977196, JX981477, EU686115, JX021531, FJ527863, AJ302451, AJ302455, JN975370, EU754952, AF284388, KF296855, AF502785, JX317207, AF502781, DQ278915, EU686867, KC179120, HM991270, AF284384, DQ632670, JQ759806, JQ747685, EU885302, GU721781, EF434047, EF505854, JQ666587, JQ619887, GQ919270, KF531831, AB627854, DQ914679, DQ914681, HQ599592, DQ279490, DQ660336, JX069862, AB607957, HE820869, FJ859345, JX966567, GU910230, AB627850, JX144030, DQ914723, HM595556, KC771473, DQ849310, EU179868, KF312152, JN890447, JX042854, EU554174, JN198518, HM992813, JQ845947, KF251310, JQ758707, AM930536, KF296912, JN865204, JN943512, GQ921743, EU245000, EU977304, EU144787, HE579322, HE579402, GU910171, HE792919, KC960885, DQ485941, JN604449, HQ607913, AF502620, DQ468027, JX944132, JN207338, JQ922240, JN207336, JX559559, JN207330, JN207333, HE820882, JX969625, HQ339994, JF744950, HE584937, JN120351, JX298885, DQ872671, AJ877102, JQ081564, DQ019391, AF071342, EF104180, JQ759755, GU827492, JN418769, GU324757, JX984750, JX256420, KF436271, JX205162, JN712450, KF435911, GU367905, JX416919, KC315933, JQ736648, AY904051, AF404126, FJ466722, HE584965, JN890282, HE584966, HQ166312, KC305124, HE977536, KC305128, AY907040, JF710504, AF483609, AJ302460, AJ302461, AJ302462, AY969615, EU685981, U75615, AJ302468, FJ210503, GU237860, JX960591, JX143632, HM044649, EU164404, HE584824, HQ116406, DQ156342, JX416911, U75617, GU721359, KC427041, EU254839, JX262800, KC179307, HQ107993, KF361474, GU721420, HM053659, EF619702, EU686156, HE820839, HQ634617, GU721810, AB277211, AJ302417, KC315945, JQ002571, AM237457, AF009805, JX489795, EU680554, KC507199, FJ236723, HQ692618, JN846717, JX944160, JQ585672, KF435573, EU520590, HM581946, DQ250382, JX243908, KC343184, KC485454, GQ479695, GU237760, KF147147, EF619849, GU237767, GU237766, AB818997, AF502847, EU683672, KF225801, KC965743, AJ488254, DQ825983, JN031007, DQ825985, KF028765, AB818999, HQ238268, EU685984, KC966180, HE998711, HQ533007, AM113729, KF251637, FN394692, KF435172, JN207307, JQ814305, HM770988, KC145175, AB511813, EU552102, AJ309344, EU645686, JQ936328, JN038492, DQ875349, EU977228 JQ814357, KF040480, JX317350, DQ401548, DQ318195, DQ318194, GU721776, KF193449, AF178544, AM262354, AB540567, AY627787, HE792907, HE579333, EU445372, AF362069, GU973687, HM053663, AB374284, DQ062977, GU237797, JQ760783, EF029240, HM751829, FM200445, AY953383, AY233922, JF742784, HM626650, FN610871, JX155902 JX006065, AB566289, AF163078, AY344976, AB566287, AF282099, AY251441, AF395693, JQ761899, AJ315835, HQ187633, KC287233, AJ315831, HE820745, JN418779, M13906, JQ761896, AJ315838, AY536373, HQ328035, JX838793, JQ758986, HQ166357, JN163855, KC965595, JN545789, JN545788, GU944558, HE579247, KF296900, EF377335, KC965954, GU269703, AB095511, EF419913, DQ993641, AB325678, HQ223035, AY513945, FJ197013, FR799277, HM071900, JN207293, FJ025268, JQ758966, GU138733, GU138730, DQ267595, GQ919269, JF770450, GU138734, DQ279488, DQ279486, DQ242472, EU164804, EF104177, GU366726, KF212243, DQ923534, GU079598, JX987761, JX984765, AY585343, JQ769260, GU721919, DQ923538, EU686756, EU040222, U75626, GU004264, EU686753, JQ765651, JX270629, JN943408, EF042604, AJ271588, HE579386, GQ479556, JQ759962, JX317413, EU516867, DQ780361, JQ905644, HQ649792, JQ247355, FN386296, AY004778, DQ102374, KF251383, GU237835, DQ383642, FN868479, GU237814, KC343032, JN943394, HQ450001, KC800573, AB217793, GQ851883, EU330630, JF309198, AY489281, GU325687, JX399008, AB164703, EF159407, AJ302429, UDB008141, UDB008140, FM200496, AJ302426, AJ302422, AJ302423, JQ683725, KF193481, JQ683727, HE792931, AB220252, FJ013057, DQ286207, JQ759811, JF414842, JX088707, JN415754, AY787715, JX559577, KC776206, GU166440, KC460867, FJ515595, KF056850, DQ118964, KC806227, KC631802, EU823315, AY528970, HQ116401, JX317516, KF251313, KC800565, AF502705, AF502810, M747697, AY527407, EU680518, AJ621773, AB374285, HQ832827, GU174316, DQ974750, JN198507, JF749806, JQ782739, HQ023202, AY616234, KC965315, AB743781, EU554161, KC507201, HM036624, EF464164, JX391942, AB743995, FJ415474, AY647237, KC965503, AB540553, HQ377280, JX898571, JN969419, DQ166962, HM123519, GU237881, AB683953, AY681487, EU498738, EU687037, AB540550, EF394866, AY853245, EU680532, HQ450006, AM292674, KF435452, AF502638, JN890354, JX256427, JF773646, KC916704, FJ347031, JN572154, AF443850, AY273300, JQ247392, JQ247393, HQ316569, GU324760, AB120858, JF440978, HQ115719, JF440976, DQ124120, HQ022342, AF333138, AB255293, GQ999456, DQ286209, HE820785, AF451751, JN038479, JQ044421, JQ044422, KC968911, KC492447, FM172902, AF437754, HM030631, HM595545, AY510424, JX414184, HQ184179, AB588822, JQ813816, JQ813817, FJ025255, AY745019, EU668292, HM216214, AF427105, EU479799, JQ769257, HM484866, EU301059, EU564808, AY265329, HQ701737, KC677889, AY907030, GU721349, AY304513, GU062277, AY907037, HM484859, AB576865, JX090109, UDB004179, JN692542, JQ327868, AY756490, JN890185, JX042994, FJ613832, AF009815, HQ332534, AF009816, EU686781, DQ520639, KC247154, HE820841, HE820847, JN717228, JX944174, GU721348, AB444657, KF435560, JQ585546, JQ775577, UDB004443, JF744968, KF192823, JN102440, AM504058, JX164074, GU907781, HQ889707, FJ612980, KF251355, AF502854, AF350291, HQ649989, GU966521, FJ481149, AY916491, AB444663, FR799197, KC691458, HE820786, JN802324, AF149926, AY372686, AY233908, HQ631033, UDB004677, KF251596, EU479757, GU079602, KC691456, DQ420883, DQ914680, DQ914683, KC305134, JN207313, AB512307, JN807326, GQ395365, JN207256, FJ425678, AB000932, JN207252, KF293814, GU138728, AY160210, UDB015006, KC565735, FJ524302, AF404127, EU272486, JF796251, JF439458, AY304511, KC592278, JX143583, JF440977, EU686925, JX982370, EU687082, JX966607, GU222370, JN687988, JN006771, JX436806, JQ936201, KF481950, AF178551, KC181937, JX144778, DQ790541, JF796076, JX898576, JX418352, AF097902, FJ411320, AF309617, FR863589, HM469970, AF163069, KF582795, AB566293, HE820790, GQ267191, JX130356, JN049828, HM060596, KF436001, GQ919283, HQ832834, JN049822, EU041786, AB594789, HE579259, HE584944, GU004268, GU237770, GQ921765, HE579253, KC305158, AF043599, GQ267190, AY344968, JN601031, JN969420, GU328624, AB540507, AM691002, JN102384, EU480019, JN545815, DQ993651, JX130360, JX398990, AY969704, KF251559, AF395695, HQ449993, U94714, KF435968, JX966550, AB859762, JF749808, U94713, GU981750, AF177152, FJ430599, JQ647433, GU981756, GU981757, EF104164, JN802311, GQ266146, HQ445083, JX155909, KF436256, DQ318204, GU078649, JN890115, DQ386141, GQ999487, EU686744, FJ426983, UDB013022, FN435799, EF600976, HM596012, JF825143, AM711381, EU816668, AJ972833, JQ905735, AF004686, EU266103, EU266107, HQ166334, EF679384, UDB004580, AM691001, JX399012, KC460880, JX982437, AB482221, AM292048, KF251253, AF350308, JF502446, JQ905803, KC179320, KF251393, GU053815, DQ323686, DQ323681, KC343119, HE820747, KF251529, DQ676536, U17215, DQ278919, EU489950, FR668016, GU903287, AJ302439, AJ302438, AJ302435, AJ302434, JN807325, AB741584, KC790941, DQ394387, FJ403513, GQ461566, KF193491, KC305164, AF502895, GU237707, EU977520, AB247177, AB482220, AY929321, GU004278, AB247171, GU461294, GU461295, JX123570, AY684241, EU686968, JX944143, JN871718, JQ796813, HQ829122, KF435590, KC806231, JX414183, GU944858, AF502733, JN662314, HQ022970, AY510418, KC623569, KC216145, KF129059, DQ279515, KF251526, JN192379, JN192376, HM140630, DQ006928, AF011289, EU089663, FJ825373, DQ307292, JN890424, KF155521, AB670714, GQ927271, AB670717, AB670711, AB670713, KF435279, GU053814, KF435375, JX414188, AF033422, GU225946, EU520610, JF773645, KC595884, KC965570, DQ812921, EU885299, DQ078757, FJ612618, KF018920, JX077035, EU686911, JX270567, HE579352, EU885297, FJ418185, DQ914724, HQ608112, HQ450016, GU174399, JN890327, HM999913, GU079580, HE584936, JQ765675, GU726947, JQ765670, HM588120, AY969986, JN120335, JQ247384, HQ891112 JQ769297, JN207242, EU002888, EU479803, AY365468, AF163083, DQ534482, KC146356, KF436052, AF416460, JX537970, JX156018, AY907035, GQ241278, AF409972, JQ388941, FR668022, EU687151, DQ468026, AY251418, AB508842, AB508840, DQ233665, GU721949, AJ302444, JF927155, AJ302442, GU721976, AJ302440, KC790931, UDB004433, GU328539, EU479791, HQ649905, KC797566, JQ753968, GU721449, HQ701742, AY613410, GU062246, AY907045, HM991267, DQ979608, JQ781840, GU721442, EU426553, DQ980024, HQ634638, AF222836, GU222372, AY969338, EF104158, AY431101, JQ081415, FJ649318, AY152583, JN943058, EU885294, HQ231255, FJ179477, EU304350, KC005785, FR799224, EF070422, HQ533789, AJ289870, KF025952, HQ611347, DQ485934, KC989106, JQ081921, HE820871, AF404125, JN603182, KF436170, HQ832964, DQ185074, KC216108, JN102460, GU553324, DQ318207, HQ589260, AB819001, AY699669, EU812501, AB819004, HQ436065, KC013976, KF251204, KF435307, AF249905, EF029217, EF029216, FJ708614, EF029198, JQ517314, GU199416, HM180398, EU479748, GU721599, DQ185081, EF104175, JX021528, KF251430, AY611071, AY329221, JN207241, HM235963, JN890375, JF506092, KF193461, KF453551, HM123501, HM051074, AB255269, HQ904082, KF193500, FN562038, GU721911, EF417805, KF193504, KF028766, HE579312, EF433991, KF144910, KF144911, FM200450, AF163090, AB444665, AB444664, HQ649964, AB444666, AB444661, AY528998, DQ525492, KC870889, EF543844, GU073125, AY684240, JN163853, EU680538, AF395694, KC179102, KC778197, JN102425, DQ520638, EU244997, GU994552, DQ279527, KC179418, EF495164, AY999117, JX860441, JQ793663, DQ836775, EU479964, AY772736, AJ875343, KC013972, AJ875346, AY208785, HE614864, HF570009, KF435344, KC148376, EF641857, JX625368, AB512308, KC305146, AY266384, KC662096, HE579269, GU004277, GU004276, EF504668, EU687114, GU004272, GU004271, EU516731, KC213751, JN102394, HQ654776, JQ862729, EU687052, JX868653, FJ172294, JX130355, HE584891, FJ427063, GQ996174, FN252438, AJ633598, JX398987, EU245009, HM069466, FJ859344, JN942165, FJ785433, EF504592, HQ449989, HQ449988, JN120346, JX868648, EF600969, HQ529711, JN383815, KF003112, JN890192, GU981748, EU715654, EF535663, GU328634, UDB004320, GQ999475, FR731421, GU322457, EF550969, GU322450, FJ477838, KC305130, AJ247519, JQ026214, AJ972825, KC305135, EU520614, EU338415, JQ747670, EU040241, HE584979, KF477240, HM162095, AB746179, KC963934, AY906949, JN975339, EU520120, HM071902, JX399005, EU828350, JX399006, EF070418, FJ025231, EF070415, JN859327, JQ517292, JX399009, KF297004, JN618372, AY233888, EU784271, AM292673, EU514295, GQ921804, GU595027, HM008727, GU174426, JN673038, AF442801, EU686126, JF440982, EU754960, GQ154505, GU055711, FJ175159, KC354573, DQ993639, JQ621881, JN102454, AY177233, FJ013071, AY566992, GQ120971, EF408555, JX317505, AF524905, FJ887922, AF264905, AF264906, HM997113, EF619857, KC537805, KC537804, FJ887928, AB255303, HQ671302, FJ210537, FN386267, HQ649813, GU083033, KF251334, GU721297, KC181926, DQ832329, JQ781696, KF251233, KF251234, GQ505688, AJ437294, AJ437295, EF679363, HE820831, FN868450, GU174305, AY428866, AY956759, JQ759940, DQ489291, AJ271418, AY157952, EU784408, FJ427055, EF419900, FN813731, FJ427059, KF435462, JQ860113, KF209290, JF439437, KC565714, FJ228189, AF377282, JQ814364, HM991266, EF458676, AY762046, JN048884, HQ896484, HE579345, AB444659, EU076958, HQ402674, AF540504, AM922204, EU479758, JN943840, JN943841, FJ427025, KC584194, AF502754, FJ418192, KC343004, AB524806, AJ877224, DQ394377, FJ427028, AF282090, GQ927270, EU178738, DQ059579, EF535699, KF040479, AF163085, JX256429, AY999125, KF477238, KC513506, GQ999534, GU237837, EU002898, HM164732, AF443193, AJ315828, AJ315829, AY586560, JX868722, EU686847, DQ875350, DQ421277, AM176740, JX280875, AM691003, KF302463, GQ921786, KC965801, AM691004, EF452446, EU040235, KC662103, KC662102, AY251073, DQ993637, AY489282, FJ151434, JQ936199, EF505495, JN163856, JN659510, EF452449, EF504607.1, GQ516009.1, GQ508761.1, KC8008470.1, JX187590.1, GQ508832.1, KC800841.1, KC800840.1, EF504876.1, HQ540685.1, EF505180.1, AY842353.1, GU014821.1, FJ761203.1, GQ510033.1, EF504642.1, GU014822.1, AY998786.1, AB581046.1, EF452470.1, FJ907534.1, EF504721.1, Y08744.2, FJ757587.1, GU014820.1, AF400896.1, KC800831.1, EF505804.1, EF505121.1, JX187587.1, KC800858.1, GQ866210.1, GQ522120.1, Y10748.1, EF504853.1, EF452471.1, KJ834329.1, AB581446.1, JX187588.1, AF163061.1, AB632670.1, Y08746.1, EF505082.1, JX187589.1, EF504723.1, AF400889.1, KC800835.1, and EF505282.1.

Example 18: Endophytes and Combination Thereof

The protocols as described in Examples 1-16 are used in connection with the endophytes of Table 1 to confirm beneficial properties on plant health, such as yield and/or past resistance, for example. In particular, endophytes from Table 1 are employed in a synthetic combination with a plant as described herein with crop plants, such as cotton. Any single or combination of endophytes listed in Table 1 can also be used in this manner, employing for example seed coatings or foliar, soil, or rhizosphere applications. A seed composition may comprise seeds and any combination of endophytes listed in Table 1. Endophytes listed in Table 1 or combinations thereof are thus employed in methods for preventing pest infestation, increased yield, treating a pest infestation, manufacturing pest-resistant seeds; or increasing a yield or reducing loss of a crop according to the methods of Examples 1-15.

What is claimed is:

1. A method for improving drought resistance in a cotton plant, the method comprising:
contacting a cotton seed with a fluid seed coating comprising purified filamentous, spore-forming, facultative fungal endophytes of at least one *Chaetomium* species wherein the contacted seed contains at least 10 CFU up to 10,000 CFU of the facultative fungal endophyte coated onto the surface of the seed, wherein the facultative fungal endophytes are present in the fluid seed coating in an amount effective to improve drought resistance of a cotton plant grown from the contacted seed compared to a reference cotton plant grown from a reference seed.

2. The method of claim 1, wherein the fluid seed coating contains at least 100 (10^2) spores/ml or 100,000 (10^4) spores/g dry weight of the facultative fungal endophytes.

3. The method of claim 1, wherein the facultative fungal endophytes are present in the fluid seed coating in an amount effective to increase biomass.

4. The method of claim 1, wherein the facultative fungal endophytes are species *Chaetomium globosum*.

5. The method of claim 4, wherein the cotton plant is variety LA122.

6. The method of claim 1, wherein the cotton plant is variety LA122.

7. The method of claim 1, wherein the facultative fungal endophytes are present in the fluid seed coating in an amount effective to reduce yield loss.

8. The method of claim 7, wherein yield loss is reduced by at least 5%.

9. The method of claim 7, wherein the reduction in yield loss results in a yield increase of at least 5%.

10. The method of claim 1, wherein enhanced resistance to drought stress is assessed by withholding water from 7-day old seedlings of the cotton plant grown in the greenhouse, wherein the seedlings have increased time to wilt as compared to a seedling grown from a reference seed.

11. The method of claim 1, wherein the seed is surface sterilized before contacting the seed with the fluid seed coating.

12. The method of claim 1, wherein the contacted seed contains at least 100 CFU, at least 300 CFU, at least 1,000 CFU, at least 3,000 CFU, or at least 10,000 CFU of the facultative fungal endophytes coated onto the surface of the seed.

* * * * *